(12) United States Patent
Gopalakrishnan et al.

(10) Patent No.: US 9,186,407 B2
(45) Date of Patent: Nov. 17, 2015

(54) PHARMACEUTICAL COMPOSITIONS AND THEIR METHODS OF USE

(75) Inventors: Murali Gopalakrishnan, Libertyville, IL (US); Marie P. Honore, Evanston, IL (US); Chih-Hung Lee, Vernon Hills, IL (US); John Malysz, Round Lake, IL (US); Jianguo Ji, Libertyville, IL (US); Tao Li, Grayslake, IL (US); Michael R. Schrimpf, Grayslake, IL (US); Kevin B. Sippy, Antioch, IL (US); David J. Anderson, Lake Bluff, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 13/080,071

(22) Filed: Apr. 5, 2011

(65) Prior Publication Data

US 2011/0190314 A1 Aug. 4, 2011

Related U.S. Application Data

(62) Division of application No. 11/953,625, filed on Dec. 10, 2007, now abandoned.

(60) Provisional application No. 60/999,761, filed on Apr. 12, 2007, provisional application No. 60/874,609, filed on Dec. 12, 2006.

(51) Int. Cl.
| | | |
|---|---|---|
| *A01N 43/82* | (2006.01) | |
| *A61K 31/41* | (2006.01) | |
| *A01N 43/40* | (2006.01) | |
| *A61K 31/44* | (2006.01) | |
| *C07D 413/00* | (2006.01) | |
| *C07D 413/04* | (2006.01) | |
| *C07D 413/14* | (2006.01) | |
| *A61K 31/4245* | (2006.01) | |
| *A61K 31/443* | (2006.01) | |
| *A61K 31/444* | (2006.01) | |
| *A61K 45/06* | (2006.01) | |

(52) U.S. Cl.
CPC ............. *A61K 45/06* (2013.01); *A61K 31/4245* (2013.01); *A61K 31/443* (2013.01); *A61K 31/444* (2013.01)

(58) Field of Classification Search
CPC .. C07D 271/06; C07D 401/12; A61K 31/397; A61K 31/4402; A61K 31/4245; A61K 31/444; A61K 31/443
USPC .......... 514/364, 338, 340; 544/138; 546/269.4
See application file for complete search history.

(56) References Cited

U.S. PATENT DOCUMENTS

| | | | |
|---|---|---|---|
| 3,964,896 A | 6/1976 | Brouwer et al. | |
| 4,022,901 A | 5/1977 | Narayanan et al. | |
| 4,122,257 A | 10/1978 | Prossel et al. | |
| 5,594,023 A | 1/1997 | Wagnon et al. | |
| 5,914,328 A | 6/1999 | Lin et al. | |
| 5,948,793 A | 9/1999 | Abreo et al. | |
| 5,977,144 A | 11/1999 | Meyer et al. | |
| 6,090,818 A | 7/2000 | Foulon et al. | |
| 6,130,217 A | 10/2000 | Arnold et al. | |
| 6,207,863 B1 | 3/2001 | Berrier et al. | |
| 6,538,003 B1 | 3/2003 | Galli et al. | |
| 6,579,880 B2 | 6/2003 | Weidner-Wells et al. | |
| 6,596,732 B2 | 7/2003 | Serradeil-Le-Gal et al. | |
| 6,605,610 B1 | 8/2003 | Coe et al. | |
| 6,624,164 B2 | 9/2003 | Schoentjes et al. | |
| 6,809,105 B2 | 10/2004 | Schrimpf et al. | |
| 6,833,370 B1 | 12/2004 | Schrimpf et al. | |
| 6,864,277 B2 | 3/2005 | Roux et al. | |
| 6,919,359 B2 | 7/2005 | Piotrowski et al. | |
| 7,041,685 B2 | 5/2006 | Cai et al. | |
| 7,119,086 B2 | 10/2006 | Di Malta et al. | |
| 7,902,379 B2 | 3/2011 | Lubisch et al. | |
| 8,017,631 B2 | 9/2011 | Dahl et al. | |
| 8,129,389 B2 | 3/2012 | Lubisch et al. | |
| 8,350,055 B2 | 1/2013 | Oost et al. | |
| 8,546,401 B2 | 10/2013 | Braje et al. | |
| 8,703,774 B2 | 4/2014 | Netz et al. | |
| 8,703,775 B2 | 4/2014 | Oost et al. | |
| 8,815,858 B2 | 8/2014 | Bjornson et al. | |
| 8,815,868 B2 | 8/2014 | Netz et al. | |
| 8,859,557 B2 | 10/2014 | Netz et al. | |
| 2003/0109545 A1 | 6/2003 | Serradeil-Le-Gal et al. | |
| 2003/0114683 A1 | 6/2003 | Roux et al. | |
| 2003/0139413 A1 | 7/2003 | Schoentjes et al. | |
| 2003/0162767 A1 | 8/2003 | Roux et al. | |
| 2004/0063601 A1 | 4/2004 | Denome et al. | |
| 2004/0152724 A1 | 8/2004 | Dart et al. | |

(Continued)

FOREIGN PATENT DOCUMENTS

| | | |
|---|---|---|
| CA | 2107348 A1 | 7/1993 |
| CA | 2593044 A1 | 7/2006 |

(Continued)

OTHER PUBLICATIONS

Cochrane Database Syst. Rev., Jul. 2005, vol. 20, Iss. 3, pp. 1-23.*
Lynch III et al. European Journal of Pharmacology, 2003, vol. 509, pp. 43-48.*
Testa, Bernard, Biochemical Pharmacology, Prodrug Research: futile or fertile? 68 (2004), pp. 2097-2106.
Ettmayer, P., Medicinal Chemistry, Lessons Learned from Marketed and Investigational Prodrugs, 47(10) (2004), pp. 2394-2404.
Prescott, David M., Methods in Cell Biology, Academic Press, New York, NY (1976).
Wilens, Timothy E. et al., Biol. Psychiatry, vol. 59, pp. 1065-1070 (2006).

(Continued)

*Primary Examiner* — Samira Jean-Louis
(74) *Attorney, Agent, or Firm* — Lisa V. Mueller; Michael Best & Friedrich LLP

(57) ABSTRACT

The invention relates to a composition comprising a neuronal nicotinic receptor ligand and an α4β2 positive allosteric modulator, a method of using the same, and a related article of manufacture.

5 Claims, 17 Drawing Sheets

(56) References Cited

U.S. PATENT DOCUMENTS

| | | |
|---|---|---|
| 2004/0180878 A1 | 9/2004 | Di Malta et al. |
| 2004/0186107 A1 | 9/2004 | Schrimpf et al. |
| 2004/0204461 A1 | 10/2004 | Karp et al. |
| 2005/0070718 A1 | 3/2005 | Lubisch et al. |
| 2006/0019976 A1 | 1/2006 | Karp et al. |
| 2007/0021465 A1 | 1/2007 | Al-Abed et al. |
| 2007/0021607 A1 | 1/2007 | Lubisch et al. |
| 2007/0185126 A1 | 8/2007 | Lubisch et al. |
| 2008/0255203 A1 | 10/2008 | Lee et al. |
| 2008/0269236 A1 | 10/2008 | Ji et al. |
| 2008/0318923 A1 | 12/2008 | Sekiguchi et al. |
| 2009/0005397 A1 | 1/2009 | Lubisch et al. |
| 2009/0163492 A1 | 6/2009 | Oost et al. |
| 2009/0215790 A1 | 8/2009 | Lubisch et al. |
| 2010/0305086 A1 | 12/2010 | Gopalakrishnan et al. |
| 2011/0077241 A1 | 3/2011 | Lubisch et al. |
| 2011/0092516 A1 | 4/2011 | Braje et al. |
| 2011/0124658 A1 | 5/2011 | Netz et al. |
| 2011/0190314 A1 | 8/2011 | Gopalakrishnan et al. |
| 2014/0187543 A1 | 7/2014 | Lubisch et al. |
| 2014/0194440 A1 | 7/2014 | Braje et al. |
| 2014/0275110 A1 | 9/2014 | Oost et al. |
| 2014/0315914 A1 | 10/2014 | Netz et al. |

FOREIGN PATENT DOCUMENTS

| | | |
|---|---|---|
| EP | 0979814 B1 | 2/2000 |
| EP | 2226074 A2 | 9/2010 |
| EP | 2101763 B1 | 7/2012 |
| EP | 2114921 B1 | 12/2012 |
| EP | 2546250 A1 | 1/2013 |
| EP | 2546251 A1 | 1/2013 |
| EP | 2546252 A1 | 1/2013 |
| WO | 9313083 A1 | 7/1993 |
| WO | 9315051 A1 | 8/1993 |
| WO | 9518105 A1 | 7/1995 |
| WO | 96/40682 | 12/1996 |
| WO | 9825901 A1 | 6/1998 |
| WO | 99/10338 | 3/1999 |
| WO | 99/32480 | 7/1999 |
| WO | 99/65876 | 12/1999 |
| WO | 0007600 A1 | 2/2000 |
| WO | 0045799 A2 | 8/2000 |
| WO | 00/71534 | 11/2000 |
| WO | 00/75110 | 12/2000 |
| WO | 01/62736 | 8/2001 |
| WO | 0155130 A2 | 8/2001 |
| WO | 0155134 A2 | 8/2001 |
| WO | 0164668 A2 | 9/2001 |
| WO | 01/81347 | 11/2001 |
| WO | 0181334 | 11/2001 |
| WO | 0187295 A1 | 11/2001 |
| WO | 0198295 A1 | 12/2001 |
| WO | 02068417 | 9/2002 |
| WO | 02/100826 | 12/2002 |
| WO | 03008407 A2 | 1/2003 |
| WO | 2004018607 | 3/2004 |
| WO | 2005030755 A1 | 4/2005 |
| WO | 2006005609 A2 | 1/2006 |
| WO | 2006047392 A2 | 5/2006 |
| WO | 2006071184 A1 | 7/2006 |
| WO | 2006072458 A2 | 7/2006 |
| WO | 2006086088 A1 | 8/2006 |
| WO | 2006/096358 | 9/2006 |
| WO | 2006100080 A1 | 9/2006 |
| WO | 2006100081 A2 | 9/2006 |
| WO | 2006100082 A2 | 9/2006 |
| WO | 2006114400 | 11/2006 |
| WO | 2007149395 | 12/2007 |
| WO | 2008028903 A2 | 3/2008 |
| WO | 2008073942 | 6/2008 |
| WO | 2008080970 A1 | 7/2008 |
| WO | 2008080971 A1 | 7/2008 |
| WO | 2008080972 A1 | 7/2008 |
| WO | 2008080973 A1 | 7/2008 |
| WO | 2009071687 A1 | 6/2009 |
| WO | 2009071689 A2 | 6/2009 |
| WO | 2009071690 A2 | 6/2009 |
| WO | 2009148452 A1 | 12/2009 |
| WO | 2010009775 A1 | 1/2010 |
| WO | 2010148598 | 6/2010 |
| WO | 2010138600 A2 | 12/2010 |
| WO | 2010148598 A1 | 12/2010 |

OTHER PUBLICATIONS

The PCT International Search Report, PCT/US2007/087091, Date of mailing May 5, 2008.
Dunbar, et al., J. Psychopharm., vol. 21, No. 2, pp. 171-178 (2007).
Skoubis et al. Neuroscience, Mar. 2006, vol. 137, pp. 583-591.
Kirrane et al. Biological Psychiatry, vol. 39, No. 7, Apr. 1996, abstract only.
Bonte, J.P., et al., "Acyl-6 benzoxazolinoines," Eur. J. Med. Chem., 1974, 9, pp. 491-496.
Humphrey et al., "A Novel Synthesis of 3-Bromo-1,2,4-oxadiazoles", J. Heterocyclic Chem, 1989, 26, pp. 23-24.
Lin Yang i, et al., "New Synthesis of 1,2,4-Triazoles and 1,2,4-Oxadiazoles", J. Org. Chem, 1979, 44(23), pp. 4160-4164.
McClelland Robert A., "Kinetics and Mechanism of Amide Acetal Hydrolysis", Journal of the American Chemical Society, 1978, 100 (6), pp. 1844-1849.
Gopalakrishnan, M. et al., "Ion channels—Ligand gated. Comprehensive Medicinal Chemistry II, Edited by Triggle D.J. et al..," Major Reference Works, 2006, Unit 2.22, pp. 877-918, Elsevier.
Higuchi T., et al., "Pro-drugs as Novel Delivery Systems," Bioreversible Carriers in Drug Design, 1987, 14, American Pharmaceutical Association and Pergamon Press.
International Search Report for application No. PCT/US2007/087090, Mailed on Oct. 20, 2008, 6 pages.
International Search Report for PCT/US08/066002 mailed on Jan. 20, 2009, 3 Pages Total.
IUPAC Commission on Nomenclature of Organic Chemistry: Rules for the Nomenclature of Organic Chemistry Section E: Stereochemistry, Pure Appl Chem, 1976,45, pp. 11-30.
Bitner et al., Brain Res. 871: pp. 66-74 (2000).
Bundgaard, E., ed., Design of Prodrugs, Elsevier Science Publishers, Amsterdam (1986) Table of Contents.
Chaplan et al., J. Neurosci. Methods, 53, pp. 55-63 (1994).
Cucchiaro et al., J. Pharmacol. Exp. Ther. 313, pp. 389-394 (2005).
Curtis et al., Pharmacology 61, pp. 127-135 (2002).
Decker et al., Curro Top. Med. Chern. 4, pp. 369-384 (2004).
Decker et al., Expert Opinion on Investigational Drugs 10, pp. 1819-1830 (2001).
Ferreira et al., J. Pharm. Exp. Ther. 294, pp. 230-238 (2000).
Furniss et al., Vogel's Textbook of Practical Organic Chemistry, 5th Edition (1989), Table of Contents.
Greene, et al., Protective Groups in Organic Synthesis, 3rd Edition, John Wiley & Sons, New York (1999) Table of Contents.
Isobe et al., J. Organ. Chern. 64, pp. 6989-6992 (1999).
Khan et al., J. Neurocytol. 33, pp. 543-556 (2004).
Kim et al., Pain, 50, p. 355 (1992).
Lauretti, G.T., Expert Reviews in Neurotherapeutics, 6, pp. 613-622 (2006).
March Advanced Organic Chemistry, 3rd Ed., John Wiley &Sons, New York page, 1157 (1985).
Mark et al., Encyclopedia of Chemical Technology, John Wiley & Sons, New York (1980) Table of Contents.
Marubio et al., Nature, 398, pp. 805-810 (1999).
Narahashi et al., Biol. Pharm. Bull. 27: pp. 1701-1706 (2004).
Pasternack, G.W., Clin. Neuropharmcol. 16:1 (1993).
Rashid, et al., Pain 125, pp. 125-135 (2006).
Rueter et al., CNS Drug Rev. 10(2): pp. 167-182 (2004).
Sobol et al., J. Med. Chem. 47: pp. 4316-4326 (2004).
Wang et al., Tetrahedron Lett. 47: pp. 105-108 (2006).
Banfi L., et al., "Ugi Multicomponent Reaction Followed by an Intermolecular Nucleophilic Substitution: Convergent

(56) References Cited

OTHER PUBLICATIONS

Multicomponent Synthesis of 1-sulfonyl 1,4-diazepan-5-ones and of their Benzo-Fuzed Derivatives," Journal of Organic Chemistry, 2007, vol. 72 (6), pp. 2151-2160.
Chattopadhyay S.K., et al., "Formation of Medium-Ring Heterocycles by Diene and Enyne Metathesis," Tetrahedron, 2007, vol. 63, pp. 3919-3952.
Diaz G.J., et al., "The [3H]dofetilide Binding Assay is a Predictive Screening Tool for hERG Blockade and Proarrhythmia: Comparison of Intact Cell and Membrane Preparations and Effects of Altering [K+]o," Journal of Pharmacological and Toxicological Methods, 2004, vol. 50 (3), pp. 187-199.
Dorwold F.Z., "Side Reactions in Organic Synthesis," Wiley-VCH, 2005, Preface.
Final Office Action mailed May 10, 2012 for U.S. Appl. No. 12/746,715, filed Dec. 7, 2010.
Final Office Action mailed Feb. 13, 2012 for U.S. Appl. No. 12/746,688, filed Nov. 29, 2010.
Final Office Action mailed Feb. 24, 2012 for U.S. Appl. No. 12/746,700, filed Nov. 29, 2010.
Final Office Action mailed Mar. 26, 2013 for U.S. Appl. No. 12/746,688, filed Nov. 29, 2010.
Final Office Action mailed Feb. 27, 2012 for U.S. Appl. No. 12/746,707, filed Dec. 7, 2010.
Freshney R.I., et al., Culture of Animal Cells, A Manual of Basic Technique, 1983, Wiley & Sons, Inc., pp. 7-9.
International Search Report for Application No. PCT/EP2008/066931, mailed on May 12, 2009, 6 pages.
International Search Report for Application No. PCT/EP2008/066934, mailed on Jun. 4, 2009, 6 pages.
International Search Report for Application No. PCT/EP2008/066935 (WO2009/071690), mailed on Jun. 4, 2009, 6 pages.
Nakamura I., et al., "Transition-Metal-Catalyzed Reactions in Heterocyclic Synthesis," Chemical Reviews, 2004, vol. 104 (5), pp. 2127-2198.
Non-Final Office Action mailed Oct. 1, 2012 for U.S. Appl. No. 12/746,700, filed Nov. 29, 2010.
Non-Final Office Action mailed Oct. 1, 2012 for U.S. Appl. No. 12/746,707, filed Dec. 7, 2010.
Non-Final Office Action mailed Oct. 12, 2012 for U.S. Appl. No. 12/746,688, filed Nov. 29, 2010.
Non-Final Office Action mailed Aug. 19, 2011 for U.S. Appl. No. 12/746,700, filed Nov. 29, 2010.
Non-Final Office Action mailed Jul. 22, 2011 for U.S. Appl. No. 12/746,688, filed Nov. 29, 2010.
Non-Final Office Action mailed Jul. 22, 2011 for U.S. Appl. No. 12/746,707, filed Dec. 7, 2010.
Non-Final Office Action mailed Aug. 30, 2011 for U.S. Appl. No. 12/746,715, filed Dec. 7, 2010.
Smalley S.L., "Genetic Influences in Childhood-Onset Psychiatric Disorders: Autism and Attention-Deficit/hyperactivity Disorder," American Journal of Human Genetics, 1997, vol. 60 (6), pp. 1276-1282.
Wakefield B., Fluorinated Pharmaceuticals, Innovations in Pharmaceutical Technology, 2000, pp. 74-78.
Final Office Action mailed Apr. 19, 2013 for U.S. Appl. No. 12/746,707, filed Dec. 7, 2010.
Notice of Allowance mailed Jun. 11, 2013 for U.S. Appl. No. 12/839,595, filed Jul. 20, 2010.
Notice of Allowance mailed Apr. 15, 2013 for U.S. Appl. No. 12/746,688, filed Nov. 29, 2010.
Notice of Allowance mailed Apr. 15, 2013 for U.S. Appl. No. 12/746,700, filed Nov. 29, 2010.
Notice of Allowance mailed Jun. 25, 2013 for U.S. Appl. No. 12/521,713, filed Sep. 7, 2010.
Notice of Allowance mailed May 28, 2013 for U.S. Appl. No. 12/746,715, filed Dec. 7, 2010.
Banker G.S. et al, "Modern Pharmaceutices, 3ed.," 1996, pp. 451 and 596, Marcel Dekker, New York.

Barberis C., et al., "Structural Bases of Vasopressin/oxytocin Receptor Function," Journal of Endocrinology, 1998, vol. 156 (2), pp. 223-239.
Bundgaard H., ed., in: Design of Prodrugs, Elsevier Science, 1985, Table of Contents.
Cheung B.S., et al., "Etiologic Significance of Arginine Vasopressin in Motion Sickness," Journal of Clinical Pharmacology, 1994, vol. 34 (6), pp. 664-670.
Co-pending U.S. Appl. No. 61/058,735, filed Jun. 4, 2008.
De Francesco R., et al., "Approaching a new era for Hepatitis C virus Therapy: Inhibitors of the NS3-4A Serine Protease and the NS5B RNA-Dependent RNA Polymerase," Antiviral Research, 2003, vol. 58 (1), pp. 1-16.
De Francesco R., et al., "Challenges and Successes in Developing New Therapies for Hepatitis C," Nature, 2005, vol. 436 (7053), pp. 953-960.
Emsley R.A., et al., "Vasopressin Secretion and Memory Impairment in Alcoholic Korsakoff's Syndrome," Alcohol and Alcoholism, 1995, vol. 30 (2), pp. 223-229.
Ersek K., et al., "The Cognitive Effects of Opioids," Pain Management Nursing, 2004, vol. 5 (2), pp. 75-93.
European Search Report for Application No. EP10163998, mailed on Jan. 28, 2011, 5 pages.
European Search Report for Application No. EP12177640, mailed on Dec. 12, 2012, 2 pages.
European Search Report for Application No. EP12177642, mailed on Dec. 12, 2012, 2 pages.
European Search Report for Application No. EP12177644, mailed on Dec. 12, 2012, 1 page.
Everts H.G., et al., "Differential Modulation of Lateral Septal Vasopressin Receptor Blockade in Spatial Learning, Social Recognition, and Anxiety-Related Behaviors in Rats," Behavioural Brain Research, 1999, vol. 99 (1), pp. 7-16.
Ex Parte Quayle Action mailed Sep. 11, 2008 for U.S. Appl. No. 10/574,211, filed Jan. 22, 2007.
Ex Parte Quayle Action mailed Aug. 21, 2012 for U.S. Appl. No. 12/839,612, filed Jul. 20, 2010.
Ex Parte Quayle Action mailed Aug. 22, 2012 for U.S. Appl. No. 12/134,678, filed Jun. 6, 2008.
Final Office Action mailed Apr. 27, 2012 for U.S. Appl. No. 12/521,713, filed Sep. 7, 2010.
Final Office Action mailed Sep. 29, 2011 for U.S. Appl. No. 12/787,937, filed May 26, 2010.
Franklin S. R., et al., "Positive Allosteric Modulation of Alpha $ Beta 2 Nicotinic Receptors Potrntiates Some CNS Effects of the Alpha 4 Beta 2 Agonist, ABT-594," Biochemical Pharmacology, 2009, vol. 78 (7), pp. 921.
Grant P.J., et al., "Effects of Physiological Concentrations of Vasopressin on Haemostatic Function in Man," Clinical Science, 1985, vol. 69 (4), pp. 471-476.
Greene T.W., et al., "Protection for the Amino group," Protective Groups in Organic Synthesis, 1999, Third Edition, pp. 494-653.
Griebel G., et al., "Anxiolytic- and Antidepressant-Like Effects of the Non-Peptide Vasopressin V1b Receptor Antagonist, SSR149415, Suggest an Innovative Approach for the Treatment of Stress-Related Disorders," Proceedings of the National Academy of Sciences, 2002, vol. 99 (9), pp. 6370-6375.
Hays R.M., et al., "Vasopressin Antagonists—Progress and Promise," The New England Journal of Medicine, 2006, vol. 355 (20), pp. 2146-2148.
Higuchi T., et al., eds., Pro-drugs as Novels Delivery Systems, vol. 14, ACS Symposium Series, 1975, Table of Contents.
Hulme C., et al., "Quaternary Substituted PDE4 Inhibitors I: the Synthesis and in Vitro Evaluation of a Novel Series of Oxindoles," Bioorganic & Medicinal Chemistry Letters, 1998, vol. 8 (2), pp. 175-178.
International Preliminary Report on Patentability and Written Opinion for Application No. PCT/US08/066002, mailed on Dec. 6, 2010, 8 pages.
International Preliminary Report on Patentability and Written Opinion for Application No. PCT/US2007/087090, mailed on Jun. 16, 2009, 11 pages.

(56) References Cited

OTHER PUBLICATIONS

International Preliminary Report on Patentability and Written Opinion for Application No. PCT/US2010/036213, mailed on Nov. 29, 2011, 14 pages.
International Search Report for Application No. PCT/US2010/036213, mailed on Nov. 24, 2010, 8 pages.
Itoh S., et al., "Attenuated Stress-induced Catecholamine Release in Mice Lacking the Vasopressin V1b Receptor," American Journal of Physiology. Endocrinology and Metabolism, 2006, vol. 291 (1), pp. E147-E151.
Japundzic-Zigon N., et al., "Effects of Nonpeptide and Selective V1 and V2 Antagonists on Blood Pressure Short-Term Variability in Spontaneously Hypertensive Rats," Journal of Pharmacological Sciences, 2004, vol. 95 (1), pp. 47-55.
Jonat S., et al., "Effect of DDAVP on Nocturnal Enuresis in a Patient with Nephrogenic Diabetes Insipidus," Archives of Disease in Childhood, 1999, vol. 81 (1), pp. 57-59.
Kocevar M., et al., "Ring Transformations of Some 4-Aminopteridine 3-Oxides and Derivatives," Tetrahedron, 1982, vol. 39 (5), pp. 823-829.
Koch Uwe et al., "2-(2-thienyl)-5,6-dihydroxy-4-carboxypyrimidines as inhibitors of the hepatitis C virus NS5B polymerase: Discovery, SAR, modeling, and mutagenesis," Journal of Medicinal Chemistry, vol. 49(5), pp. 1693-1705, 2006.
Kocsis J., et al., "Effect of a Vasopressin Antagonist d(CH2)5Tyr(Met)AVP on the Development of Renal Vasospasm Induced by Estrin Plus Vasopressin Administration in Rats," Investigative Radiology, 1987, vol. 22 (12), pp. 973-977.
Kocsis J., et al., "Histochemical and Ultrastructural Study of Renal Cortical Necrosis in Rats Treated with Oestrone + Vasopressin, and its Prevention with a Vasopressin Antagonist," British Journal of Experimental Pathology, 1987, vol. 68 (1), pp. 35-43.
Lee C.R., et al., "Vasopressin: a New Target for the Treatment of Heart Failure," American Heart Journal, 2003, vol. 146 (1), pp. 9-18.
March J., "Advanced Organic Chemistry: Reactions, Mechanisms, and Structure" 3rd Edition, John Wilsey & Sons, 1985, Table of Contents.
Mark N.F., et al., "Kirk-Othmer Encyclopedia of Chemical Technology" Second Completely Revised Edition, John Wiley & Sons Inc., 1972, Table of Contents.
Maturi M.F., et al., "Coronary Vasoconstriction Induced by Vasopressin. Production of Myocardial Ischemia in Dogs by Constriction of Nondiseased Small Vessels," Circulation, 1991, vol. 83 (6), pp. 2111-2121.
Non-Final Office Action mailed Mar. 2, 2012 for U.S. Appl. No. 12/134,678, filed Jun. 6, 2008.
Non-Final Office Action mailed Aug. 4, 2009 for U.S. Appl. No. 11/440,569, filed May 25, 2006.
Non-Final Office Action mailed Jun. 5, 2009 for U.S. Appl. No. 10/574,211, filed Jan. 22, 2007.
Non-Final Office Action mailed Dec. 9, 2008 for U.S. Appl. No. 11/440,569, filed May 25, 2006.
Non-Final Office Action mailed Dec. 9, 2010 for U.S. Appl. No. 11/953,625, filed Dec. 10, 2007.
Non-Final Office Action mailed Jan. 10, 2012 for U.S. Appl. No. 12/839,612, filed Jul. 20, 2010.
Non-Final Office Action mailed Feb. 11, 2013 for U.S. Appl. No. 13/590,261, filed Aug. 21, 2012.
Non-Final Office Action mailed Apr. 15, 2011 for U.S. Appl. No. 12/134,678, filed Jun. 6, 2008.
Non-Final Office Action mailed Apr. 18, 2011 for U.S. Appl. No. 12/787,937, filed May 26, 2010.
Non-Final Office Action mailed Aug. 19, 2011 for U.S. Appl. No. 12/521,713, filed Sep. 7, 2010.
Non-Final Office Action mailed Jan. 22, 2009 for U.S. Appl. No. 10/574,211, filed Jan. 22, 2007.
Non-Final Office Action mailed Feb. 24, 2012 for U.S. Appl. No. 12/839,595, filed Jul. 20, 2010.
Non-Final Office Action mailed Nov. 30, 2010 for U.S. Appl. No. 10/574,211, filed Jan. 22, 2007.
Non-Final Office Action mailed Sep. 30, 2011 for U.S. Appl. No. 12/134,678, filed Jun. 6, 2008.
Notice of Allowance mailed Oct. 1, 2010 for U.S. Appl. No. 11/440,569, filed May 25, 2006.
Notice of Allowance mailed Dec. 2, 2009 for U.S. Appl. No. 10/574,211, filed Jan. 22, 2007.
Notice of Allowance mailed Sep. 4, 2012 for U.S. Appl. No. 12/839,612, filed Jul. 20, 2010.
Notice of Allowance mailed May 5, 2010 for U.S. Appl. No. 10/574,211, filed Jan. 22, 2007.
Notice of Allowance mailed Dec. 10, 2012 for U.S. Appl. No. 12/134,678, filed Jun. 6, 2008.
Notice of Allowance mailed Jan. 10, 2011 for U.S. Appl. No. 10/574,211, filed Jan. 22, 2007.
Notice of Allowance mailed Jul. 10, 2012 for U.S. Appl. No. 12/521,713, filed Sep. 7, 2010.
Notice of Allowance mailed Mar. 12, 2010 for U.S. Appl. No. 11/440,569, filed May 25, 2006.
Notice of Allowance mailed Nov. 13, 2012 for U.S. Appl. No. 12/521,713, filed Sep. 7, 2010.
Notice of Allowance mailed Jun. 24, 2010 for U.S. Appl. No. 11/440,569, filed May 25, 2006.
Notice of Allowance mailed Jun. 26, 2012 for U.S. Appl. No. 12/839,595, filed Jul. 20, 2010.
Office action mailed Dec. 1, 2011 for European Application No. 08770247.8 filed Jun. 6, 2008.
Office action mailed Sep. 10, 2012 for European Application No. 10720520.5 filed May 26, 2010.
Office action mailed Nov. 17, 2011 for European Application No. 10163998.7 filed Dec. 12, 2007.
Office action mailed Jun. 18, 2012 for European Application No. 10163998.7 filed Dec. 12, 2007.
Office action mailed Mar. 29, 2012 for European Application No. 08770247.8 filed Jun. 6, 2008.
Oshikawa S., et al., "Vasopressin Stimulates Insulin Release from Islet Cells through V1b Receptors: a Combined Pharmacological/knockout Approach," Molecular Pharmacology, 2004, vol. 65 (3), pp. 623-629.
Pavo I., et al., "Vasopressin Deficiency Decreases the Frequency of Gastroduodenal Ulceration in Humans," Journal of Physiology, 2000, vol. 94 (1), pp. 63-66.
Poulain R.F., et al., "Parallel Synthesis of 1,2,4-oxadiazoles from carboxylic Acids Using an Improved, Uronium-based Activation," Tetrahedron Letters, 2001, vol. 42 (8), pp. 1495-1498.
Ring R.H., et al., "The Central Vasopressinergic System: Examining the Opportunities for Psychiatric Drug Development," Current Pharmaceutical Design, 2005, vol. 11 (2), pp. 205-225.
Roche E.B., ed., Bioreversible Carries in Drug Design Theory and Application, Pergamon Press, 1987, Table of Contents.
Ryckmans T., et al., "Modulation of the Vasopressin System for the Treatment of CNS Diseases," Current opinion in drug discovery & development, 2010, vol. 13 (5), pp. 538-547.
Scheurer M.A., et al., "Vasopressin to Attenuate Pulmonary Hypertension and Improve Systemic Blood Pressure Pressure after Correction of Obstructed Total Anomalous Pulmonary Venous Return," The Journal of Thoracic and Cardiovascular Surgery, 2005, vol. 129 (2), pp. 464-466.
Serradeil-Le Gal C., et al., "Characterization of (2S,4R)-1-[5-chloro-1-[(2,4-dimethoxyphenyl)sulfonyl]-3-(2-methoxy-phenyl)-2-oxo-2,3-dihydro-1H-indol-3-yl]-4-hydroxy-N,N-dimethyl-2-pyrrolidine carboxamide (SSR149415), a Selective and Orally Active Vasopressin V1b Receptor Antagonist," Journal of Pharmacology and Experimental Therapeutics, 2002, vol. 300 (3), pp. 1122-1130.
Street L.J., et al., "Synthesis and Serotonergic Activity of 5-(Oxadiazolyl)tryptamines: Patent Agonists for 5-HT1D Receptors," Journal of Medicinal Chemistry, 1993, vol. 36 (11), pp. 1529-1538.
Supplementary Partial European Search Report for Application No. 08770247, mailed on Mar. 16, 2012, 4 pages.
Thibonnier M., "Development and Therapeutic Indications of Orally-active Non-peptide Vasopressin Receptor Antagonists," Expert Opinion on Investigational Drugs, 1998, vol. 7 (5), pp. 729-740.

(56) References Cited

OTHER PUBLICATIONS

Thibonnier M., et al., "Vasopressin Receptor Antagonists in Heart Failure," Current Opinion in Pharmacology, 2003, vol. 3 (6), pp. 683-687.
Venkatesh S., et al., "Role of the Development Scientist in Compound Lead Selection and Optimization," Journal of Pharmaceutical Sciences, 2000, vol. 89 (2), pp. 145-154.
Webster M., "Ninth New Collegiate Dictionary" Definition of Prevention, Springfield, Massachusetts, 2000, pp. 933.
Wersinger S.R., et al., "Vasopressin V1b Receptor Knockout Reduces Aggressive Behavior in Male Mice," Molecular Psychiatry, 2002, vol. 7 (9), pp. 975-984.
Wolff, Mandred E.., "Burger's Medicinal Chemistry and Drug Discovery," Principles and Practice, 1995, 975-977, 5th Ed,vol. 1, John Wiley & Sons.
Yatagai T., et al., "Close Association of Severe Hyponatremia with Exaggerated Release of Arginine Vasopressin in Elderly Subjects with Secondary Adrenal Insufficiency," European Journal of Endocrinology, 2003, vol. 148 (2), pp. 221-226.
Final Office Action mailed Dec. 3, 2012 for U.S. Appl. No. 13/361,488, filed Jan. 30, 2012.
Final Rejection mailed Oct. 10, 2013 for U.S. Appl. No. 13/590,261, filed Aug. 21, 2012.
Griebel G., et al., "The Vasopressin V1b Receptor as a Therapeutic Target in Stress-Related Disorders," Current Drug Targets. CNS and Neurological Disorders, 2003, vol. 2 (3), pp. 191-200.
Non-Final Office Action mailed Aug. 1, 2013 for U.S. Appl. No. 12/521,713, filed Sep. 7, 2010.
Non-Final Office Action mailed Aug. 2, 2013 for U.S. Appl. No. 12/746,700, filed Nov. 29, 2010.
Non-Final Office Action mailed Jul. 20, 2012 for U.S. Appl. No. 13/361,488, filed Jan. 30, 2012.
Notice of Allowance mailed Aug. 20, 2013 for U.S. Appl. No. 12/746,700, filed Nov. 29, 2010.
Office action mailed Aug. 1, 2013 for European Application No. 10163998.7 filed Dec. 12, 2007.
Final Office Action mailed Nov. 22, 2013 for U.S. Appl. No. 12/746,707, filed Dec. 7, 2010.
Notice of Allowance mailed Dec. 6, 2013 for U.S. Appl. No. 12/521,713, filed Sep. 7, 2010.
Notice of Allowance mailed Nov. 25, 2013 for U.S. Appl. No. 12/746,688, filed Nov. 29, 2010.
Notice of Allowance mailed Nov. 27, 2013 for U.S. Appl. No. 12/746,700, filed Nov. 29, 2010.
Notice of Allowance mailed Apr. 11, 2014 for U.S. Appl. No. 12/521,713, filed Sep. 7, 2010.
Non-Final Office Action mailed Jun. 19, 2014 for U.S. Appl. No. 12/746,707, filed Dec. 7, 2010.
Non-Final Office Action mailed May 22, 2014 for U.S. Appl. No. 12/787,937, filed May 26, 2010.
Notice of Allowance and Examiner Initiated Interview Summary mailed Jun. 6, 2014 for U.S. Appl. No. 13/590,261, filed Aug. 21, 2012.
[Qian, Xuhong. Syntheses and Insecticidal Activities of Novel 2,5-Disubstituted-1,3,4-Oxadiazoles. J. Chem. Tech. Biotechnol. 1996 (67) 124-1 30.1.

[Reynaud, Pierre. A new synthetic route to 1,3,4-oxadiazoles. Pharmacological study of some new derivatives. J. Het. Chem. 199229 (4)991-993.
Khan, Mahmud. Structure-activity relationships of tyrosinase inhibitory combinatorial library of 2,5-disubstituted-1,3,4-oxadizole analogues. Bioorganic and Medicinal Chemistry. 13 (2005), pp. 3385-3395.
Brain, Christopher, Novel procedure for the synthesis of 1,3,4-oxadiazoles from 1,2-diacylhydrazines using polymer-supported Burgess reagent under microwave conditions. Tetrahedron Letters, 40 (1999), pp. 3275-3278.
Stella, Valentino J, Expert Opinion of Therapeutic Patents, Prodrugs as therapeutics, 2004, 14(3), pp. 277-280.
Wolff et al. (Burger's Medicinal Chemistry, 5th Ed., vol. 1, pp. 975-977, 1994).
Non-Final Office Action mailed Dec. 3, 2014 for U.S. Appl. No. 14/252,425, filed Apr. 14, 2014.
Notice of Allowance and Examiner Initiated Interview Summary mailed Jan. 5, 2015 for U.S. Appl. No. 12/787,937, filed May 26, 2010.
Notice of Allowance mailed Dec. 24, 2014 for U.S. Appl. No. 12/746,707, filed Dec. 7, 2010.
Lemmens-Gruber R., et al., "Vasopressin Antagonists," Cellular and Molecular Life Sciences, 2006, vol. 63 (15), pp. 1766-1779.
Non-Final Office Action mailed Nov. 10, 2014 for U.S. Appl. No. 14/037,026, filed Sep. 25, 2013.
Non-Final Office Action mailed Sep. 12, 2014 for U.S. Appl. No. 14/251,384, filed Apr. 11, 2014.
Non-Final Office Action mailed Sep. 25, 2014 for U.S. Appl. No. 14/040,412, filed Sep. 27, 2013.
Gruber R. L., et al., "Drugs of the Future: Review Vasopressin Antagonists," Cellular and Molecular Life Sciences, 2006, vol. 63, pp. 1769-1773.
Koob G. F., et al., "A Role for Brain Stress Systems in Addiction," Neuron, 2008, vol. 59 (1), pp. 11-34.
Non Final Rejection mailed Jan. 16, 2015 for U.S Appl. No. 14/481,847, filed Sep. 9, 2014.
Office Action mailed Apr. 13, 2015 for U.S Appl. No. 14/554,734, filed Nov. 26, 2014.
Office Action mailed Apr. 15, 2015 for U.S Appl. No. 14/040,412, filed Sep. 27, 2013.
Office Action mailed Apr. 21, 2015 for U.S Appl. No. 14/252,425, filed Apr. 14, 2014.
Office Action mailed Apr. 24, 2015 for U.S Appl. No. 14/251,384, filed Apr. 11, 2014.
Office Action mailed Mar. 30, 2015 for U.S Appl. No. 14/037,026, filed Sep. 25, 2013.
Zhou Y., et al., "Involvement of Arginine Vasopressin and V1b Receptor in Heroin withdrawal and Heroin Seeking Precipitated by Stress and by Heroin," Neuropsychopharmacology, 2008, vol. 33 (2), pp. 226-236.
Non-Final Office Action mailed Aug. 26, 2015 for U.S. Appl. No. 14/251,384, filed Apr. 11, 2014.
Non-Final Office Action mailed Aug. 27, 2015 for U.S. Appl. No. 14/252,425 (6 pages).

* cited by examiner

PHARMACEUTICAL COMPOSITIONS AND THEIR METHODS OF USE

CROSS-REFERENCE TO RELATED APPLICATIONS

This is a divisional of U.S. patent application Ser. No. 11/953,625, filed on Dec. 10, 2007, which claims priority to U.S. Provisional Patent Application No. 60/999,761, filed on Apr. 12, 2007 and U.S. Provisional Patent Application No. 60/874,609, filed on Dec. 12, 2006, the contents of all of which are hereby incorporated by reference.

BACKGROUND OF THE INVENTION

1. Technical Field

The invention relates to a composition comprising a neuronal nicotinic receptor ligand and an α4β2 allosteric modulator, a method of using the same, and a related article of manufacture.

2. Description of Related Technology

Neuronal nicotinic receptors, especially α4β2 neuronal nicotinic acetylcholine receptors (nAChRs) have been targeted for pain and various central nervous system diseases. Antisense knockdown of the α4 subunit was found to decrease the analgesic effect of agonists (Bitner R S, Nikkel A L, Curzon P, Donnelly-Roberts D L, Puttfarcken P S, Namovic M, Jacobs I C, Meyer M D, and Decker M W (2000) *Brain Res.* 871:66-74). Reduced antinociceptive responses to nicotine also is seen in α4 gene knockout animals (Marubio L M, Arroyo-Jimenez M D, Cordero-Erausquin M, Lena C, Le Novere N, d'Exaerde A D, Huchet M, Damaj M I, and Changeux J P (1999) *Nature* 398:805-810). Both α4 and β2 nAChRs are responsible for mediating nicotinic analgesia at supraspinal responses and spinal sites (Decker, M W, Rueter, L E and Bitner, R S (2004) Nicotinic acetylcholine receptor agonists: a potential new class of analgesics, Curr Top Med Chem., 4: 369-384). Antinociceptive effects through α4β2 nAChRs are generally attributed to stimulation of brainstem monoaminergic transmission, particularly in the raphe (Cucchiaro G, Chaijale N, and Commons K G (2005) *J Pharmacol Exp Ther.* 313:389-394). However, α4β2 stimulation of GABAergic and glycinergic inhibitory transmission in the spinal cord also may contribute (Rashid M H, Furue H, Yoshimura M, and Ueda H (2006) *Pain* 125:125-135).

Central α3* nAChRs may contribute to nicotinic analgesia (Khan I M, Wennerholm M, Singletary E, Polston K, Zhang L, Deerinck T, Yaksh T L, and Taylor P (2004) *J Neurocytol.* 33:543-556), but α3β4 ligands are of little interest because of likely autonomic side effects. Indeed, the goal has been to avoid α3* neuronal nicotinic receptor (NNR), as the dose-limiting emetic liability of nonselective compounds has been attributed to activation of α3 containing nAChRs. α3* nAChRs are expressed in the enteric nervous system as well as in other components of the peripheral and central nervous systems. Area postrema and nucleus tractus solitarius are brainstem nuclei thought to be involved in nausea and emesis. α3* nAChRs in the dorsal motor nucleus of the vagus and in nucleus tractus solitarius have been implicated in gastric and blood pressure responses to nicotine injected locally (Ferreira M, Singh A, Dretchen K L, Kellar K J, and Gillis R A (2000) *J. Pharmacol. Exp. Ther.* 294:230-238).

Compounds with varying degrees of selectivity for α4β2 nAChRs over other nicotinic subtypes (α3, α7, α1-containing) have been discovered over the years. For example, ABT-594 (referred to as Compound A in this application) was efficacious across a number of rodent models of nociception including acute thermal, chemogenic, neuropathic, and visceral pain (Decker M W, Meyer M D, and Sullivan J P (2001) Expert Opinion on Investigational Drugs 10:1819-1830). Available data suggest that ligands with selectivity for the α4β2 nAChRs over α3β4 efficacy is preferred for low adverse event profiles. In theory, the therapeutic index could be expanded by (a) reducing α3β4 activity or (b) increasing α4β2 efficacy without increasing α3β4 activity. The latter may be achieved by an α4β2 selective positive allosteric modulator (PAM) either alone or in combination with exogenous α4β2 agonist. Positive allosteric modulators can potentiate effects by enhancing the efficacy and or potency of agonists. Accordingly, an α4β2 selective positive allosteric modulator can selectively enhance effects at the preferred α4β2 nAChRs over other nAChR subtypes.

Initially known positive allosteric modulators of the α4β2 nAChRs have been nonselective and not very potent. For example, nefiracetam has been reported to potentiate α4β2 nAChR responses (Narahashi T, Moriguchi S, Zhao X, Marszalec W, and Yeh J Z (2004) *Biol. Pharm. Bull.* 27:1701-1706). More recently, subtype selective PAMs have been disclosed. Compounds like 3-(3-pyridin-3-yl-1,2,4-oxadiazol-5-yl)benzonitrile and others have been described with robust α4β2 PAM effects with little modulatory activity at other subtypes such as α3β4 (e.g., see WO 2006/114400, published Nov. 2, 2006).

Pain is an unmet medical need and the methods and possibilities for treatments of such indications are insufficient. Although continued efforts are being made to treat pain using nAChR agonists, robust efficacy in pain may be limited by the range of side effects associated with their use, albeit to differing degrees. In light of the significance of chronic pain and the limitations in their treatment, it would be beneficial to identify new methods of treating such disorders, particularly in a manner that reduces adverse ganglionic effects such as at the gastrointestinal systems (e.g. emesis). It would be particularly beneficial to identify compounds and compositions that offer an opportunity to wide the therapeutic window of nicotinic (nAChR) agonists in pain. Enhanced efficacy with nAChR ligands for the treatment of other central nervous system diseases such as cognitive and attention deficits is also desirable.

SUMMARY OF THE INVENTION

This invention provides compositions that are useful for treatment of diseases or disorders related to the nicotinic acetylcholine receptor (nAChR) with enhanced efficacy and less side effects than nicotinic agents alone. In part, the invention relates to a composition wherein the efficacy of a nicotinic (nAChR) agent is enhanced by co-dosing a nicotinic ligand with a positive allosteric modulator (PAM) of nAChR subtype α4β2. The invention relates to compositions for treatment of individuals with nAChR-mediated diseases or disorders, and particularly for pain or CNS disorders, which involves a combination of a nicotinic ligand with an α4β2 positive allosteric modulator. The invention provides a synergistic combination of a nicotinic agonist or partial agonist with a α4β2 positive allosteric modulator. The invention further provides for the treatment or prevention of nAChR-mediated diseases and disorders, particularly pain and central nervous system disorders, in mammals, and particularly in humans. Such combination enhances the efficacy of α4β2 ligand and can provide a beneficial alternative to current treatments.

In one embodiment, the invention relates to a composition comprising (i) a nicotinic acetylcholine receptor ligand; and (ii) a nicotinic acetylcholine receptor subtype α4β2 selective positive allosteric modulator, in admixture with at least one pharmaceutically acceptable excipient. The preferred nicotinic acetylcholine receptor ligand is a nicotinic acetylcholine receptor subtype α4β2 ligand. The invention is most beneficial wherein the amounts of (i) and (ii) together are effective in treating nAChR-mediated disease states, for example pain. Other CNS diseases where α4β2 nAChRs are involved, such as cognition and attention disorders, may also benefit.

In another embodiment, the invention relates to method for use in treating or preventing pain, including neuropathic pain, and cognitive disorders in a patient, comprising: (i) administering an amount of a nicotinic acetylcholine receptor ligand to the patient; and (ii) administering an amount of a nicotinic acetylcholine receptor subtype α4β2 allosteric modulator to the patient; wherein the amounts of (i) and (ii) together are more effective in treating pain or cognitive disorders. The preferred nicotinic acetylcholine receptor ligand is a neuronal nicotinic receptor subtype α4β2 ligand. The invention also relates to use of a nicotinic acetylcholine receptor subtype α4β2 allosteric modulator in combination of a pharmaceutical active agent that improves cholinergic function to treat attention or cognitive dysfunction. Use of a nicotinic acetylcholine receptor subtype α4β2 allosteric modulator in combination with a pharmaceutical active agent used to treat neuropsychological dysfunction also is described.

Yet another embodiment of the invention relates to an article of manufacture, comprising: (i) a first pharmaceutical dosage form comprising at least one nicotinic acetylcholine receptor ligand; (ii) a second pharmaceutical dosage form comprising at least one nicotinic acetylcholine receptor subtype α4β2 positive allosteric modulator, wherein the article contains first and second pharmaceutical dosage forms.

Radiolabelled compounds useful for evaluating the binding affinity of nicotinic acetylcholine receptor subtype α4β2 positive allosteric modulators also are described herein. Radiolabelled α4β2 positive allosteric modulators also are disclosed.

The embodiments of the invention, how to prepare them, and how to use them are further described herein.

DETAILED DESCRIPTION OF THE INVENTION

Figure 1A:
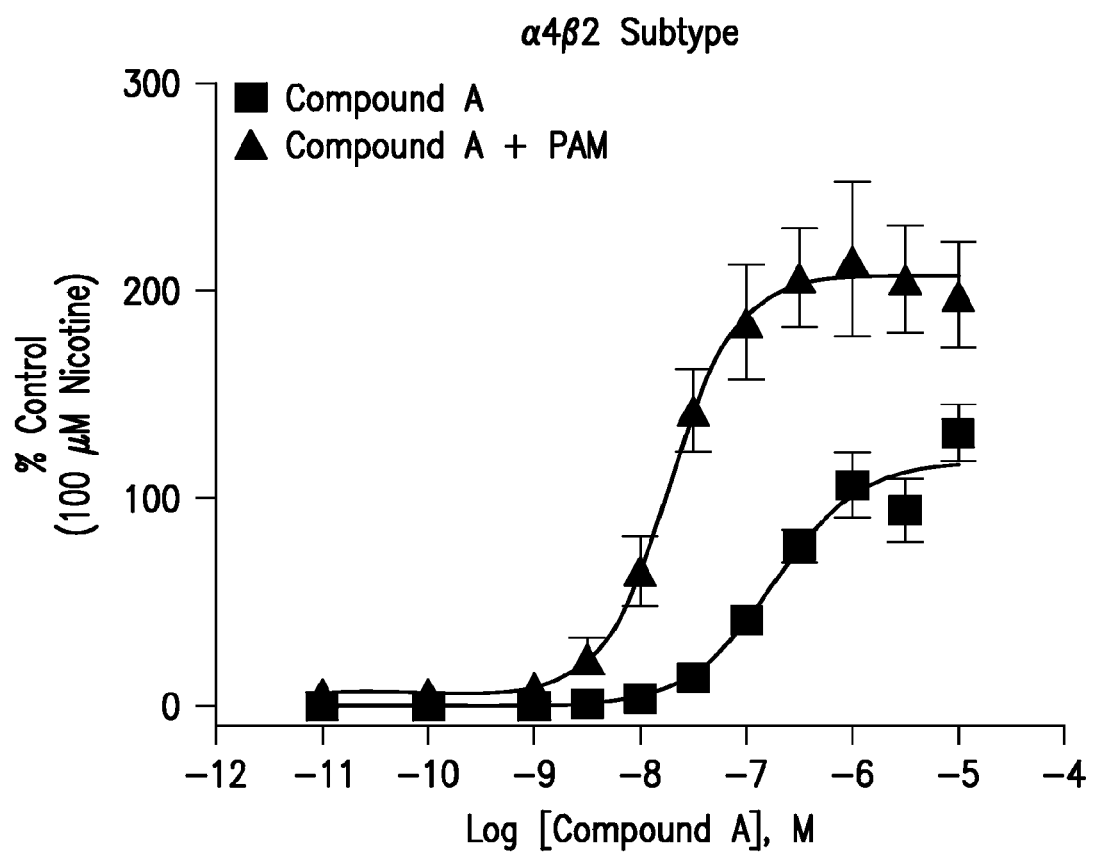
FIGS. 1A and 1B depict responses of a representative nicotinic acetylcholine receptor ligand, 5-[(2R)-azetidin-2-ylmethoxy]-2-chloropyridine (Compound A) in the absence and presence of a nicotinic acetylcholine receptor subtype α4β2 positive allosteric modulator, 3-(3-(pyridin-3-yl)-1,2,4-oxadiazol-5-yl)benzonitrile (PAM, Compound 1), at human α4β2 or α3β4 nicotinic acetylcholine receptor subtypes expressed in HEK-293 cells. The data demonstrate a leftward shift in potency ($EC_{50}$ value) at α4β2, but not α3β4, nAChRs.

Compounds suitable for the composition, method, and article of manufacture for the invention are any chemical compounds for which α4β2 nicotinic receptor activity can be identified.

Although typically it may be recognized that an asterisk is used to indicate that the exact subunit composition of a receptor is uncertain, for example α4β2* indicates a receptor that contains the α4 and β2 subunits proteins in combination with other subunits.

It has been found that the efficacy of nicotinic receptor ligands surprisingly can be improved by combining a nicotinic acetylcholine receptor ligand, particularly an α4β2 receptor ligand (agonist, partial agonist), with a nicotinic acetylcholine receptor α4β2 subtype selective positive allosteric modulator (PAM). Such combinations are highly efficient for improving the efficacy of α4β2 ligand for treatment of pain and other disease indications such as cognitive deficits when compared to administration of an α4β2 receptor ligand alone.

Nicotinic Acetylcholine Subtype α4β2 Receptor Ligand

Nicotinic acetylcholine subtype α4β2 receptor ligands modulate the function by altering the activity of the receptor. Suitable compounds also can be partial agonists that partially block or partially activate the α4β2 receptor or agonists that activate the receptor. Nicotinic acetylcholine receptor α4β2 receptor ligands suitable for the invention can include full agonists or partial agonists. Compounds modulating activity of nicotinic acetylcholine receptor α4β2 subtype are suitable for the invention regardless of the manner in which they interact with the receptor.

One manner for characterizing α4β2 receptor ligands is by a binding assay. [$^3$H]-Cytisine binding values ("$K_i$ Cyt") of compounds of the invention ranged from about 0.001 nanomolar to greater than 100 micromolar. Preferred compounds for the composition demonstrate binding values of from about 0.001 nanomolar to 10 micromolar. The [$^3$H]-cytisine binding assays have been well reported; however, further details for carrying out the assays can be obtained in International Publication No. WO 99/32480; U.S. Pat. Nos. 5,948,793 and 5,914,328; WO 2004/018607; U.S. Pat. No. 6,809,105; WO 00/71534; and U.S. Pat. No. 6,833,370.

Accordingly, α4β2 receptor ligands suitable for the invention can be compounds of various chemical classes. Particularly, some examples of α4β2 receptor ligands suitable for the invention include, but are not limited to heterocyclic ether derivatives, for example as described in International Publication No. WO 99/32480, published Jul. 1, 1999 and further described and claimed in U.S. Pat. No. 5,948,793, issued Sep. 7, 1999, and U.S. Pat. No. 5,914,328, issued Jun. 22, 1999; N-substituted diazabicyclic derivatives, for example as described in International Publication No. WO 2004/0186107, published Sep. 23, 2004, and further described and claimed in U.S. Pat. No. 6,809,105, issued Oct. 26, 2004; heterocyclic substituted amino azacycles, for example as described in International Publication No. WO 00/71534, published Nov. 30, 2000, and further described and claimed in U.S. Pat. No. 6,833,370, issued Dec. 21, 2004; all of which are hereby incorporated by reference in their entirety. Further description and methods for preparing the compounds have been reported in the patents, patent publications, and international patent publications cited.

Additional examples of α4β2 receptor ligands suitable for the invention include, but are not limited to, aryl-fused azapolycyclic compounds, for example as described in International Publication No. WO 2001062736, published Aug. 30, 2001; aryl-substituted olefinic amine compounds, for example as described in International Publication Nos. WO 9965876, published Dec. 23, 1999, and WO 00/75110, published Dec. 14, 2000; pyridopyranoazepine derivatives, for example as described in U.S. Pat. No. 6,538,003, published Mar. 25, 2003; benzylidene- and cinnamylidene-anabaseines, for examples as described in International Publication No. WO 99/10338, published Mar. 4, 1999; and 3-pyridoxylalkyl heterocyclic ether compounds, for example as described in International Publication No. WO 96/040682, published Dec. 19, 1996; all of which are hereby incorporated by reference in their entirety. Further description and methods for preparing the compounds have been reported in the patents and international patent publications cited.

Other compounds reported as demonstrating α4β2 ligands include, but are not limited to, TC-1734 (ispronicline), GTS-21, 4-hydroxy-GTS-21, TC-5619, TC-2696, dianicline and varenicline, which are all described in the publicly available literature.

Specific examples of compounds contemplated for the α4β2 receptor ligands include, but are not limited to,
5-[(2R)-azetidin-2-ylmethoxy]-2-chloropyridine;
(3R)-1-pyridin-3-ylpyrrolidin-3-amine;
2-methyl-3-(2-(S)-pyrrolidinylmethoxy)pyridine;
3-(5,6-dichloro-pyridin-3-yl)-1S,5S-3,6-diazabicyclo[3.2.0]heptane;
(R,R)-1-(pyridin-3-yl)octahydro-pyrrolo[3,4-b]pyrrole;
6,10-methano-6H-pyrazino[2,3-h][3]benzazepine;
7,8,9,10-tetrahydro-(2S,4E)-N-methyl-5-(5-isopropoxy-3-pyridyl)-4-penten-2-amine;
(2S,4E)-N-methyl-5-(5-methoxy-3-pyridyl)-4-penten-2-amine;
(2S,4E)-N-methyl-5-(5-ethoxy-3-pyridyl)-4-penten-2-amine;
(2S,4E)-N-methyl-3-pyrimidine-4-penten-2-amine;
(5aS,8S,10aR)-5a,6,9,10-tetrahydro-7H,11H-8,10a-methanopyrido[2',3':5,6]pyrano[2,3-d]azepine;
3-[1-(2,4-dimethoxy-phenyl)-meth-(E)-ylidene]-3,4,5,6-tetrahydro-[2,3']bipyridinyl; and
3-[1-(2-methoxy-4-hydroxyphenyl)-meth-(E)-ylidene]-3,4,5,6-tetrahydro-[2,3']bipyridinyl;
or pharmaceutically acceptable salts thereof.

Nicotinic Acetylcholine Subtype α4β2 Receptor Positive Allosteric Modulator

Positive allosteric modulators are compounds that potentiate receptor responses to acetylcholine without themselves triggering receptor activation or desensitization, or either, of the receptor.

One manner for characterizing α4β2 positive allosteric modulator activity is by characterization in human HEK cells expressing the human nicotinic acetylcholine receptor subtype α4β2, particularly by use of Fluorescent Image Plate Reader technology. Such assay has been reported and further details for carrying out the assays can be obtained in International Publication Nos. WO 2006/114400, published Nov. 2, 2006. Another method to identify and characterize allosteric modulator activity is by expressing the α4β2 subunits in *Xenopus* oocytes or cell lines, and by measuring effects on ligand-evoked current responses as previously described (Curtis L, Buisson B, Bertrand S and Bertrand, D., 2002; Molecular Pharmacology, 61: 127-135).

Steroid hormones represent a family of molecules with varying modulatory effects on nAChRs as well as other members of the LGIC superfamily. For example, positive allosteric modulation of human α4β2 nAChRs expressed either in *Xenopus* oocytes or in human embryonic kidney cells was reported with 17 β-estradiol (Curtis L, Buisson B, Bertrand S. and Bertrand D, 2002; Molecular Pharmacology, 61: 127-135). Examples of compounds reported as selective α4β2 positive allosteric modulators are oxadiazole derivatives, for example as described in WO 2006/114400.

Another suitable α4β2 positive allosteric modulator is 3,5-diphenylisoxazole, which is commercially available from Sigma Aldrich, St. Louis, Mo., USA.

Other suitable examples of α4β2 positive allosteric modulators include, but are not limited to, oxadiazole derivatives. Suitable oxadiazole derivatives can include 1,2,4-oxadiazole derivatives and 1,3,4-oxadiazole derivatives. Examples of 1,3,4-oxadiazole derivatives are described in co-pending U.S. Patent Application No. 61/000,295, filed on Apr. 12, 2007, wherein the methods of preparation disclosed are incorporated by reference herein. Such compounds have the formula (I):

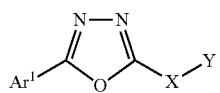

(I)

or are pharmaceutically acceptable salts and prodrugs thereof, wherein

X is a bond, O, $NR^1$, S, or $C_1$-$C_3$ alkylene;
Y represents a monocyclic aryl, cycloalkyl, heterocycle, or heteroaryl group;
$Ar^1$ represents a monocyclic aryl or a heteroaryl group; and
$R^1$ is hydrogen, alkyl, haloalkyl or arylalkyl.

X is selected from a bond, O, $NR^1$, S, or $C_1$-$C_3$ alkylene, wherein $R^1$ is selected from hydrogen, alkyl, haloalkyl, and arylalkyl. Preferably, X is a bond. Preferably, $R^1$ is hydrogen or alkyl.

Y represents a monocyclic aryl, cycloalkyl, heterocycle, or heteroaryl group, which can be substituted or unsubstituted with substituents. Examples of suitable heterocycle groups can include, but are not limited to, pyrrolidine, piperidine, and the like. Examples of suitable heteroaryl groups can include, but are not limited to, thienyl, furanyl, pyridinyl, pyrazinyl, and the like. A preferred monocyclic aryl group is substituted or unsubstituted phenyl. Suitable substituents for the monocyclic aryl, heterocycle, or heteroaryl group are, for example, alkyl, cycloalkyl, cycloalkylalkyl, halo, haloalkyl, hydroxyl, alkoxy, haloalkoxy, nitro, and cyano.

$Ar_1$ represents a monocyclic aryl, such as substituted or unsubstituted phenyl, or heteroaryl group. Examples of suitable heteroaryl groups include, but are not limited, thienyl, furanyl, pyrrolyl, pyrazolyl, thiazolyl, 1,3,4-thiadiazolyl, and pyridinyl, each of which can be unsubstituted or substituted with one, two, or three substituents selected from alkyl, cycloalkyl, cycloalkylalkyl, halo, haloalkyl, hydroxyl, alkoxy, haloalkoxy, nitro, cyano, and amino.

In one embodiment, suitable 2,5-disubstituted-1,3,4-oxadiazole derivatives can have the formula (I) wherein X is a bond; Y is aryl, cycloalkyl, heterocycle, or heteroaryl; and $Ar^1$ is monocyclic aryl or heteroaryl.

In another embodiment, suitable 2,5-disubstituted-1,3,4-oxadiazole derivatives can have the formula (I) wherein X is a bond; Y is monocyclic cycloalkyl, phenyl, thienyl, furyl, pyridinyl, pyrazinyl, pyrrolidinyl, or piperidinyl optionally substituted with one or more of the substituents selected from the group consisting of alkyl, halogen, haloalkyl, hydroxy, alkoxy, haloalkoxy, nitro and cyano; and $Ar^1$ is phenyl, thienyl, furyl, pyrrolyl, pyrazolyl, thiazolyl, 1,3,4-thiadiazolyl, pyrimidinyl, pyrazinyl, or pyridinyl optionally substituted with one or more of the substituents selectected from the group consisting of alkyl, alkylcarbonyl, alkylsulfonyl, alkythio, alrylalkyl, aryloxy, arylalkyloxy, halogen, haloalkyl, hydroxy, alkoxy, haloalkoxy, nitro, cyano, and $NZ^1Z^2$, wherein $Z^1$ and $Z^2$ are hydrogen, alkyl, alkylcarbonyl, alkoxycarbonyl, aryl, arylalkyl, and formyl.

In another embodiment, the suitable 2,5-disubstituted-1,3,4-oxadiazole derivatives can have the formula (I) wherein X is a bond; Y is pyridyl; and $Ar^1$ is phenyl, pyrimidinyl, pyrazinyl, or pyridinyl optionally substituted with one or more of the substituents selected from the group consisting of alkyl, halogen, haloalkyl, hydroxy, alkoxy, haloalkoxy, nitro, cyano, and $NZ^1Z^2$, wherein $Z^1$ and $Z^2$ are hydrogen, alkyl, alkylcarbonyl, alkoxycarbonyl, aryl, arylalkyl, and formyl.

Other suitable examples of compounds reported as α4β2 positive allosteric modulators are oxadiazole derivatives, for example as described in WO 2006/114400, published Nov. 2, 2006. Further examples of oxadiazole compounds that are suitable as α4β2 positive allosteric modulators are also provided in WO 02/100826, published Dec. 19, 2002. Yet other suitable examples of α4β2 positive allosteric modulators include, but are not limited to, compounds of the formula (II):

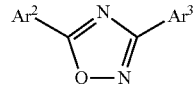

(II)

or are pharmaceutically acceptable salts thereof, wherein $Ar^2$ is monocyclic aryl or monocyclic heteroaryl, wherein the aryl or heteroaryl is substituted or unsubstituted, and, when substituted, the aryl or heteroaryl is substituted with 1, 2, 3, or 4 substituents selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_4$-$C_{10}$ heterocycle, $C_1$-$C_6$ alkyl, —($C_1$-$C_6$ alkyl)NHC(O)O—($C_1$-$C_6$ alkyl), $C_1$-$C_6$ hydroxyalkyl, $C_1$-$C_6$ alkylcarbonyl, amino, hydroxyl, haloalkyl-C(O)—, haloalkyl-$SO_2$—, alkyl-$SO_2$—, —$SO_2NH_2$, —$SO_2NH(C_1$-$C_6$ alkyl), —$SO_2N(C_1$-$C_6$ alkyl)$_2$, cyano, nitro, $C_1$-$C_6$ acylamino, $C_1$-$C_6$ alkoxy, —C(O)$NH_2$, —C(O)O—($C_1$-$C_6$ alkyl), and carboxy; and $Ar^3$ is monocyclic aryl or monocyclic heteroaryl, wherein the aryl or heteroaryl is substituted or unsubstituted, and, when substituted, the aryl or heteroaryl is substituted with a substituent selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_1$-$C_6$ alkyl, $C_1$-$C_6$ hydroxyalkyl, amino, hydroxyl, haloalkyl-$SO_2$—, cyano, nitro, $C_1$-$C_6$ acylamino, $C_1$-$C_6$ alkoxy, —N($C_1$-$C_6$ alkyl)$_2$, and carboxy.

In one embodiment, suitable 3,5-disubstituted-1,2,4-oxadiazole derivatives can have the formula (I) wherein $Ar^2$ is substituted monocyclic aryl or monocyclic heteroaryl, which can be substituted or unsubstituted, and $Ar^3$ is substituted monocyclic aryl or heteroaryl, which can be substituted or unsubstituted. When the aryl or heteroaryl group for $Ar^2$ is substituted the substituent is selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_4$-$C_{10}$ heterocycle, $C_1$-$C_6$ alkyl, —($C_1$-$C_6$ alkyl)NHC(O)O—($C_1$-$C_6$ alkyl), $C_1$-$C_6$ hydroxyalkyl, $C_1$-$C_6$ alkylcarbonyl, amino, hydroxyl, haloalkyl-C(O)—, haloalkyl-SO$_2$—, alkyl-SO$_2$—, —SO$_2$NH$_2$, —SO$_2$NH($C_1$-$C_6$ alkyl), —SO$_2$N($C_1$-$C_6$ alkyl)$_2$, cyano, nitro, $C_1$-$C_6$ acylamino, $C_1$-$C_6$ alkoxy, —C(O)NH$_2$, —C(O)O—($C_1$-$C_6$ alkyl), and carboxy. When the aryl or heteroaryl group for $Ar^3$ is substituted the substituent is selected from halo, $C_1$-$C_6$ haloalkyl, $C_6$-$C_{10}$ aryl, $C_4$-$C_7$ cycloalkyl, $C_2$-$C_6$ alkenyl, $C_2$-$C_6$ alkynyl, $C_5$-$C_{10}$ heteroaryl, $C_1$-$C_6$ alkyl, $C_1$-$C_6$ hydroxyalkyl, amino, hydroxyl, haloalkyl-SO$_2$—, cyano, nitro, $C_1$-$C_6$ acylamino, $C_1$-$C_6$ alkoxy, —N($C_1$-$C_6$ alkyl)$_2$, and carboxy. Preferred for monocyclic heteroaryl are pyridine-3-yl, pyridine-4-yl, and pyridine-2 (1H)-one.

In another embodiment, suitable 3,5-disubstituted-1,2,4-oxadiazole derivatives can have the formula (I) wherein wherein $Ar^2$ is pyridinyl, which can be substituted or unsubstituted, or substituted phenyl; and $Ar^3$ is pyridinyl, which can be substituted or unsubstituted, or substituted phenyl. The pyridinyl group, when substituted, is substituted with fluoro. The phenyl group is substituted with cyano or halo. It is preferred that the pyridinyl group for $Ar^2$ or $Ar^3$ is pyridin-3-yl. The preferred phenyl group is substitute with fluoro, sulfonamide or cyano, and preferably cyano.

Specific examples of α4β2 positive allosteric modulators are, for example, 3,5-disubstituted-1,2,4-oxadiazole derivatives, such as:
3-(3-(pyridin-3-yl)-1,2,4-oxadiazol-5-yl)benzonitrile;
3,5-di(pyridin-3-yl)-1,2,4-oxadiazole;
3-(5-(pyridin-3-yl)-1,2,4-oxadiazol-3-yl)benzonitrile;
3-(5-(6-fluoropyridin-3-yl)-1,2,4-oxadiazol-3-yl)benzonitrile;
5-(5-bromopyridin-3-yl)-3-(pyridin-3-yl)-1,2,4-oxadiazole;
3-(pyridin-3-yl)-5-(3-(trifluoromethylsulfonyl)phenyl)-1,2, 4-oxadiaole;
3-(3-(6-methylpyridin-3-yl)-1,2,4-oxadiazol-5-yl)benzonitrile;
5-(5-(pyrrol-1-yl)pyridin-3-yl)-3-(pyridin-3-yl)-1,2,4-oxadiazole;
5-(3-(pyridin-3-yl)-1,2,4-oxadiazol-5-yl)pyridin-3-ol;
5-(3,4-difluorophenyl)-3-(pyridin-3-yl)-1,2,4-oxadiazole;
5-(2,3-difluorophenyl)-3-(pyridin-3-yl)-1,2,4-oxadiazole;
5-(pyrazin-2-yl)-3-(pyridin-3-yl)-1,2,4-oxadiazole;
5-(3,5-difluorophenyl)-3-(pyridin-3-yl)-1,2,4-oxadiazole;
5-(2,3,5-trifluorophenyl)-3-(pyridin-3-yl)-1,2,4-oxadiazole;
5-(2,4,5-trifluorophenyl)-3-(pyridin-3-yl)-1,2,4-oxadiazole;
5-(2,5-difluorophenyl)-3-(pyridin-3-yl)-1,2,4-oxadiazole;
5-(4-chloro-2,5-difluorophenyl)-3-(pyridin-3-yl)-1,2,4-oxadiazole;
5-(5-methylpyrazin-2-yl)-3-(pyridin-3-yl)-1,2,4-oxadiazole;
4-(3-(pyridin-3-yl)-1,2,4-oxadiazol-5-yl)benzonitrile;
2,3,6-trifluoro-5-(3-(pyridin-3-yl)-1,2,4-oxadiazol-5-yl) phenol;
2-fluoro-5-(3-(pyridin-3-yl)-1,2,4-oxadiazol-5-yl)phenol;
2-fluoro-4-(3-(pyridin-3-yl)-1,2,4-oxadiazol-5-yl)phenol;
5-(3-chloro-4-fluorophenyl)-3-(pyridin-3-yl)-1,2,4-oxadiazole;
5-(3,4-dichlorophenyl)-3-(pyridin-3-yl)-1,2,4-oxadiazole;
2-nitro-5-(3-(pyridin-3-yl)-1,2,4-oxadiazol-5-yl)phenol;
5-(2,3,6-trifluorophenyl)-3-(pyridin-3-yl)-1,2,4-oxadiazole;
2,2,2-trifluoro-1-(4-(3-(pyridin-3-yl)-1,2,4-oxadiazol-5-yl) phenyl)ethanone;
5-(3-fluorophenyl)-3-(pyridin-3-yl)-1,2,4-oxadiaole;
5-(4-fluorophenyl)-3-(pyridin-3-yl)-1,2,4-oxadiaole;
5-(2-fluorophenyl)-3-(pyridin-3-yl)-1,2,4-oxadiaole;
3-fluoro-5-(3-(pyridin-3-yl)-1,2,4-oxadiazol-5-yl)benzonitrile;
3-(2,3-difluorophenyl)-5-(pyridin-3-yl)-1,2,4-oxadiazole;
3-(3,4-difluorophenyl)-5-(pyridin-3-yl)-1,2,4-oxadiazole;
5-(2,6-difluorophenyl)-3-(pyridin-3-yl)-1,2,4-oxadiazole;
3-(3-(pyridin-3-yl)-1,2,4-oxadiazol-5-yl)benzenesulfonamide;
5-(2,4-difluorophenyl)-3-(pyridin-3-yl)-1,2,4-oxadiazole;
5-(2,3,4-trifluorophenyl)-3-(pyridin-3-yl)-1,2,4-oxadiazole;
5-(3,4,5-trifluorophenyl)-3-(pyridin-3-yl)-1,2,4-oxadiazole;
5-(4-chloro-3-fluorophenyl)-3-(pyridin-3-yl)-1,2,4-oxadiazole;
5-(3-nitrophenyl)-3-(pyridin-3-yl)-1,2,4-oxadiazole;
5-(3-(methylsulfonyl)phenyl)-3-(pyridin-3-yl)-1,2,4-oxadiazole;
3-(2-chloropyridin-4-yl)-5-(pyridin-3-yl)-1,2,4-oxadiaole;
3-(3-(pyridin-3-yl)-1,2,4-oxadiazol-5-yl)benzamide;
4-(5-(pyridin-3-yl)-1,2,4-oxadiazol-3-yl)pyridin-2(1H)-one;
tert-butyl 3-(3-(pyridin-3-yl)-1,2,4-oxadiaol-5-yl)benzoate;
2-amino-5-(3-(pyridin-3-yl)-1,2,4-oxadiazol-5-yl)phenol;
N,N-dimethyl-4-(5-(pyridin-3-yl)-1,2,4-oxadiazol-3-yl)pyridin-2-amine;
3-(3-(pyridin-3-yl)-1,2,4-oxadiazol-5-yl)benzoic acid;
5-(3-(1H-tetrazol-5-yl)phenyl)-3-(pyridin-3-yl)-1,2,4-oxadiaole;
N,N-diethyl-3-(3-(pyridin-3-yl)-1,2,4-oxadiazol-5-yl)benzenesulfonamide;
2-fluoro-5-(3-(pyridin-3-yl)-1,2,4-oxadiazol-5-yl)benzonitrile;
3-(3-(1H-tetrazol-5-yl)phenyl)-5-(pyridin-3-yl)-1,2,4-oxadiaole;
3-(6-chloropyridin-3-yl)-5-(pyridin-3-yl)-1,2,4-oxadiaole;
5-(6-chloropyridin-3-yl)-3-(pyridin-3-yl)-1,2,4-oxadiaole;
5-(5-(pyridin-3-yl)-1,2,4-oxadiazol-3-yl)pyridin-2(1H)-one;
5-(3-(pyridin-3-yl)-1,2,4-oxadiazol-5-yl)pyridin-2(1H)-one;
N-methyl-3-(3-(pyridin-3-yl)-1,2,4-oxadiazol-5-yl)benzenesulfonamide;
3-(3-(pyridin-3-yl)-1,2,4-oxadiazol-5-yl)aniline;
(3-(3-(pyridin-3-yl)-1,2,4-oxadiazol-5-yl)phenyl)methanamine;
5-(2-chloropyridin-4-yl)-3-(pyridin-3-yl)-1,2,4-oxadiaole;
4-(3-(pyridin-3-yl)-1,2,4-oxadiazol-5-yl)pyridin-2(1H)-one;
tert-butyl 3-(3-(pyridin-3-yl)-1,2,4-oxadiazol-5-yl)benzylcarbamate;
5-(3-bromophenyl)-3-(pyridin-3-yl)-1,2,4-oxadiazole;
1-(3-(3-(pyridin-3-yl)-1,2,4-oxadiazol-5-yl)phenyl)pyrrolidin-2-one;
tert-butyl 3-(3-(pyridin-3-yl)-1,2,4-oxadiazol-5-yl)phenylcarbamate;
N,N-dimethyl-1-(3-(3-(pyridin-3-yl)-1,2,4-oxadiazol-5-yl) phenyl)methanamine;
5-(3-(piperazin-1-yl)phenyl)-3-(pyridin-3-yl)-1,2,4-oxadiazole;
1-(3-(3-(pyridin-3-yl)-1,2,4-oxadiazol-5-yl)phenyl)ethanone;
3-(6-chloropyridin-3-yl)-5-(2,3-difluorophenyl)-1,2,4-oxadiazole;
3-(6-chloropyridin-3-yl)-5-(3,4-difluorophenyl)-1,2,4-oxadiazole;
(R)-3-(pyridin-3-yl)-5-(3-(pyrrolidin-2-yl)phenyl)-1,2,4-oxadiazole;
5-(3-(1H-pyrazol-3-yl)phenyl)-3-(pyridin-3-yl)-1,2,4-oxadiazole;
1-(3-(3-(pyridin-3-yl)-1,2,4-oxadiazol-5-yl)phenyl)ethanol;

3-(3-(6-chloropyridin-3-yl)-1,2,4-oxadiazol-5-yl)benzonitrile;
3-(4-fluorophenyl)-5-(pyridin-3-yl)-1,2,4-oxadiazole;
3-(5-(6-chloropyridin-3-yl)-1,2,4-oxadiazol-3-yl)benzonitrile;
3-(5-(2-fluoropyridin-3-yl)-1,2,4-oxadiazol-3-yl)benzonitrile; and
3-fluoro-5-(5-(pyridin-3-yl)-1,2,4-oxadiazol-3-yl)benzonitrile;
or pharmaceutically acceptable salts thereof.

Other specific examples of α4β2 positive allosteric modulators are, for example, 2,5-disubstituted-1,3,4-oxadiazole derivatives, such as:
2,5-di(pyridin-3-yl)-1,3,4-oxadiazole;
2-(5-bromopyridin-3-yl)-5-(pyridin-3-yl)-1,3,4-oxadiazole;
2-(pyridin-3-yl)-5-(4-(trifluoromethyl)phenyl)-1,3,4-oxadiazole;
2-(pyridin-3-yl)-5-o-tolyl-1,3,4-oxadiazole;
2-(pyridin-3-yl)-5-m-tolyl-1,3,4-oxadiazole;
2-(pyridin-3-yl)-5-p-tolyl-1,3,4-oxadiazole;
2-(5-(pyridin-3-yl)-1,3,4-oxadiazol-2-yl)phenol;
3-(5-(pyridin-3-yl)-1,3,4-oxadiazol-2-yl)phenol;
4-(5-(pyridin-3-yl)-1,3,4-oxadiazol-2-yl)phenol;
2-(3-methoxyphenyl)-5-(pyridin-3-yl)-1,3,4-oxadiazole;
2-(4-methoxyphenyl)-5-(pyridin-3-yl)-1,3,4-oxadiazole;
2-(2-fluorophenyl)-5-(pyridin-3-yl)-1,3,4-oxadiaole;
2-(3-fluorophenyl)-5-(pyridin-3-yl)-1,3,4-oxadiaole;
2-(4-fluorophenyl)-5-(pyridin-3-yl)-1,3,4-oxadiaole;
2-(2-chlorophenyl)-5-(pyridin-3-yl)-1,3,4-oxadiazole;
2-(3-chlorophenyl)-5-(pyridin-3-yl)-1,3,4-oxadiazole;
2-(4-chlorophenyl)-5-(pyridin-3-yl)-1,3,4-oxadiazole;
2-(2-bromophenyl)-5-(pyridin-3-yl)-1,3,4-oxadiazole;
2-(3-bromophenyl)-5-(pyridin-3-yl)-1,3,4-oxadiazole;
2-(4-bromophenyl)-5-(pyridin-3-yl)-1,3,4-oxadiazole;
3-(5-(pyridin-3-yl)-1,3,4-oxadiazol-2-yl)benzonitrile;
4-(5-(pyridin-3-yl)-1,3,4-oxadiazol-2-yl)benzonitrile;
N,N-dimethyl-3-(5-(pyridin-3-yl)-1,3,4-oxadiazol-2-yl)aniline;
N,N-dimethyl-4-(5-(pyridin-3-yl)-1,3,4-oxadiazol-2-yl)aniline;
2-(pyridin-3-yl)-5-(3-(trifluoromethyl)phenyl)-1,3,4-oxadiazole;
2-(pyridin-3-yl)-5-(3-(trifluoromethoxy)phenyl)-1,3,4-oxadiazole;
2-(4-phenoxyphenyl)-5-(pyridin-3-yl)-1,3,4-oxadiazole;
2-(4-(benzyloxy)phenyl)-5-(pyridin-3-yl)-1,3,4-oxadiazole;
2-(3,4-dimethylphenyl)-5-(pyridin-3-yl)-1,3,4-oxadiaole;
2-(3,5-dimethylphenyl)-5-(pyridin-3-yl)-1,3,4-oxadiaole;
2-(2,5-dimethylphenyl)-5-(pyridin-3-yl)-1,3,4-oxadiaole;
2-(2,4-dimethylphenyl)-5-(pyridin-3-yl)-1,3,4-oxadiaole;
2-(3,4-dimethylphenyl)-5-(pyridin-3-yl)-1,3,4-oxadiazole;
2-(2,3-dimethoxyphenyl)-5-(pyridin-3-yl)-1,3,4-oxadiazole;
2-(2,4-dimethoxyphenyl)-5-(pyridin-3-yl)-1,3,4-oxadiazole;
2-(2,5-dimethoxyphenyl)-5-(pyridin-3-yl)-1,3,4-oxadiazole;
2-(2,4-dimethoxyphenyl)-5-(pyridin-3-yl)-1,3,4-oxadiazole;
2-(3,5-dimethoxyphenyl)-5-(pyridin-3-yl)-1,3,4-oxadiazole;
2-(benzo[d][1,3]dioxol-5-yl)-5-(pyridin-3-yl)-1,3,4-oxadiazole;
2-(pyridin-3-yl)-5-(3,4,5-trimethoxyphenyl)-1,3,4-oxadiazole;
2-(3,4-dichlorophenyl)-5-(pyridin-3-yl)-1,3,4-oxadiazole;
2-(2,4-dichlorophenyl)-5-(pyridin-3-yl)-1,3,4-oxadiazole;
2-(2,5-dichlorophenyl)-5-(pyridin-3-yl)-1,3,4-oxadiazole;
2-(3,4-dichlorophenyl)-5-(pyridin-3-yl)-1,3,4-oxadiazole;
5-methyl-2-(5-(pyridin-3-yl)-1,3,4-oxadiazol-2-yl)phenol;
2-methyl-5-(5-(pyridin-3-yl)-1,3,4-oxadiazol-2-yl)phenol;
2-(3-fluoro-2-methylphenyl)-5-(pyridin-3-yl)-1,3,4-oxadiazole;
2-(5-fluoro-2-methylphenyl)-5-(pyridin-3-yl)-1,3,4-oxadiazole;
2-(3-fluoro-4-methylphenyl)-5-(pyridin-3-yl)-1,3,4-oxadiazole;
2-(2,3-difluorophenyl)-5-(pyridin-3-yl)-1,3,4-oxadiazole;
2-(2,4-difluorophenyl)-5-(pyridin-3-yl)-1,3,4-oxadiazole;
2-(2,5-difluorophenyl)-5-(pyridin-3-yl)-1,3,4-oxadiazole;
2-(3,5-difluorophenyl)-5-(pyridin-3-yl)-1,3,4-oxadiazole;
1-(4-(5-(pyridin-3-yl)-1,3,4-oxadiazol-2-yl)phenyl)ethanone;
2-(4-isopropylphenyl)-5-(pyridin-3-yl)-1,3,4-oxadiazole;
2-(3-methoxy-4-methylphenyl)-5-(pyridin-3-yl)-1,3,4-oxadiazole;
2-(4-ethoxyphenyl)-5-(pyridin-3-yl)-1,3,4-oxadiazole;
2-(4-(methylthio)phenyl)-5-(pyridin-3-yl)-1,3,4-oxadiazole;
2-(3-fluoro-4-methoxyphenyl)-5-(pyridin-3-yl)-1,3,4-oxadiazole;
2-(naphthalen-1-yl)-5-(pyridin-3-yl)-1,3,4-oxadiazole;
2-(naphthalen-2-yl)-5-(pyridin-3-yl)-1,3,4-oxadiazole;
4-chloro-2-(5-(pyridin-3-yl)-1,3,4-oxadiazol-2-yl)phenol;
2-(4-tert-butylphenyl)-5-(pyridin-3-yl)-1,3,4-oxadiaole;
N-(4-(5-(pyridin-3-yl)-1,3,4-oxadiaol-2-yl)phenyl)acetamide;
2-(4-propoxyphenyl)-5-(pyridin-3-yl)-1,3,4-oxadiazole;
2-(4-isopropoxyphenyl)-5-(pyridin-3-yl)-1,3,4-oxadiazole;
2-(5-chloro-2-methoxyphenyl)-5-(pyridin-3-yl)-1,3,4-oxadiazole;
2-(4-fluoronaphthalen-1-yl)-5-(pyridin-3-yl)-1,3,4-oxadiazole;
N,N-diethyl-4-(5-(pyridin-3-yl)-1,3,4-oxadiazol-2-yl)aniline;
2-(4-butoxyphenyl)-5-(pyridin-3-yl)-1,3,4-oxadiazole;
2-(2-methoxy-4-(methylthio)phenyl)-5-(pyridin-3-yl)-1,3,4-oxadiazole;
2-(4-(methylsulfonyl)phenyl)-5-(pyridin-3-yl)-1,3,4-oxadiazole;
2-(2-chloro-5-(methylthio)phenyl)-5-(pyridin-3-yl)-1,3,4-oxadiazole;
2-(2-fluoro-5-(trifluoromethyl)phenyl)-5-(pyridin-3-yl)-1,3,4-oxadiazole;
2-(2-chloro-5-(trifluoromethyl)phenyl)-5-(pyridin-3-yl)-1,3,4-oxadiazole;
2-(2-phenethylphenyl)-5-(pyridin-3-yl)-1,3,4-oxadiazole;
2-(2-bromo-5-methoxyphenyl)-5-(pyridin-3-yl)-1,3,4-oxadiazole;
2-(5-bromo-2-chlorophenyl)-5-(pyridin-3-yl)-1,3,4-oxadiaole;
2-(2-iodophenyl)-5-(pyridin-3-yl)-1,3,4-oxadiazole;
2-(3-iodophenyl)-5-(pyridin-3-yl)-1,3,4-oxadiazole;
2-(4-iodophenyl)-5-(pyridin-3-yl)-1,3,4-oxadiazole;
2-(pyridin-3-yl)-5-(pyrimidin-5-yl)-1,3,4-oxadiazole;
2-(5-methylpyrazin-2-yl)-5-(pyridin-3-yl)-1,3,4-oxadiazole;
2-(2-chloro-6-methylpyridin-3-yl)-5-(pyridin-3-yl)-1,3,4-oxadiaole;
2-(2-methyl-6-(trifluoromethyl)pyridin-3-yl)-5-(pyridin-3-yl)-1,3,4-oxadiaole;
2-(2-(ethylthio)pyridin-3-yl)-5-(pyridin-3-yl)-1,3,4-oxadiazole;
2-(2,6-dimethoxypyridin-3-yl)-5-(pyridin-3-yl)-1,3,4-oxadiazole;
2-(2-(methylthio)pyridin-3-yl)-5-(pyridin-3-yl)-1,3,4-oxadiazole;
5-chloro-3-(5-(pyridin-3-yl)-1,3,4-oxadiazol-2-yl)pyridin-2-ol;

2-(2,6-dichloro-5-fluoropyridin-3-yl)-5-(pyridin-3-yl)-1,3,4-oxadiazole;
2-(2,5-dichloropyridin-3-yl)-5-(pyridin-3-yl)-1,3,4-oxadiazole;
2-(6-chloropyridin-3-yl)-5-(pyridin-3-yl)-1,3,4-oxadiaole;
2-(2,6-dichloropyridin-3-yl)-5-(pyridin-3-yl)-1,3,4-oxadiazole;
2-(2-chloropyridin-3-yl)-5-(pyridin-3-yl)-1,3,4-oxadiazole; and
2-(pyridin-3-yl)-5-(quinolin-3-yl)-1,3,4-oxadiazole;
or pharmaceutically acceptable salts thereof.

Compound names are assigned by using Struct=Name naming algorithm, which is part of the CHEMDRAW® ULTRA v. 9.0.7 software suite.

Definition of Terms

As used throughout this specification and the appended claims, the designation $C_x$-$C_y$, wherein x and y are integers from 1 to 10 refer to a range of carbon atoms in the hydrocarbon portion of the group which it modifies, for example, the designation "$C_1$-$C_6$ haloalkyl" refers to at least one halogen appended to the parent molecular moiety through an alkyl group having from 1 to 6 carbon atoms. The following terms have the following meanings:

The term "acyl hydrazide", as used herein, means a —C(O)NHNH$_2$ group.

The term "alkenyl", as used herein, means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkoxy", as used herein, means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy", as used herein, means an alkoxy group, as defined herein, appended to the parent molecular moiety through another alkoxy group, as defined herein. Representative examples of alkoxyalkoxy include, but are not limited to, tert-butoxymethoxy, 2-ethoxyethoxy, 2-methoxyethoxy, and methoxymethoxy.

The term "alkoxyalkoxyalkyl", as used herein, means an alkoxyalkoxy group, as defined herein, appended to the parent molecular moiety through an alkyl group, as defined herein. Representative examples of alkoxyalkoxyalkyl include, but are not limited to, tert-butoxymethoxymethyl, ethoxymethoxymethyl, (2-methoxyethoxy)methyl, and 2-(2-methoxyethoxy)ethyl.

The term "alkoxyalkyl", as used herein, means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl", as used herein, means an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl", as used herein, means an alkoxycarbonyl group, as defined herein, appended to the parent molecular moiety through an alkyl group, as defined herein. Representative examples of alkoxycarbonylalkyl include, but are not limited to, 3-methoxycarbonylpropyl, 4-ethoxycarbonylbutyl, and 2-tert-butoxycarbonylethyl.

The term "alkoxysulfonyl", as used herein, means an alkoxy group, as defined herein, appended to the parent molecular moiety through a sulfonyl group, as defined herein. Representative examples of alkoxysulfonyl include, but are not limited to, methoxysulfonyl, ethoxysulfonyl and propoxysulfonyl.

The term "alkyl", as used herein, means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl", as used herein, means an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylcarbonylalkyl", as used herein, means an alkylcarbonyl group, as defined herein, appended to the parent molecular moiety through an alkyl group, as defined herein. Representative examples of alkylcarbonylalkyl include, but are not limited to, 2-oxopropyl, 3,3-dimethyl-2-oxopropyl, 3-oxobutyl, and 3-oxopentyl.

The term "alkylcarbonyloxy", as used herein, means an alkylcarbonyl group, as defined herein, appended to the parent molecular moiety through an oxygen atom. Representative examples of alkylcarbonyloxy include, but are not limited to, acetyloxy, ethylcarbonyloxy, and tert-butylcarbonyloxy.

The term "alkylcarbonyloxyalkyl", as used herein, means an alkylcarbonyloxy group, as defined herein, appended to the parent molecular moiety through an alkyl group.

The term "alkylene", as used herein, means a divalent group derived from a straight or branched chain hydrocarbon of from 1 to 10 carbon atoms. Representative examples of alkylene include, but are not limited to, —CH$_2$—, —CH(CH$_3$)—, —C(CH$_3$)$_2$—, —CH$_2$CH$_2$—, —CH$_2$CH$_2$CH$_2$—, —CH$_2$CH$_2$CH$_2$CH$_2$—, and —CH$_2$CH(CH$_3$)CH$_2$—.

The term "alkylsulfinyl", as used herein, means an alkyl group, as defined herein, appended to the parent molecular moiety through a sulfinyl group, as defined herein. Representative examples of alkylsulfinyl include, but are not limited to, methylsulfinyl and ethylsulfinyl.

The term "alkylsulfinylalkyl", as used herein, means an alkylsulfinyl group, as defined herein, appended to the parent molecular moiety through an alkyl group, as defined herein. Representative examples of alkylsulfinylalkyl include, but are not limited to, methylsulfinylmethyl and ethylsulfinylmethyl.

The term "alkylsulfonyl", as used herein, means an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylsulfonylalkyl", as used herein, means an alkylsulfonyl group, as defined herein, appended to the parent molecular moiety through an alkyl group, as defined herein. Representative examples of alkylsulfonylalkyl include, but are not limited to, methylsulfonylmethyl and ethylsulfonylmethyl.

The term "alkylthio", as used herein, means an alkyl group, as defined herein, appended to the parent molecular moiety through a sulfur atom. Representative examples of alkylthio include, but are not limited, methylthio, ethylthio, tert-butylthio, and hexylthio.

The term "alkylthioalkyl", as used herein, means an alkylthio group, as defined herein, appended to the parent molecular moiety through an alkyl group, as defined herein. Representative examples of alkylthioalkyl include, but are not limited, methylthiomethyl and 2-(ethylthio)ethyl.

The term "alkynyl", as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "amino", as used herein, means a —$NH_2$ group.

The term "aryl,", as used herein, means phenyl, a bicyclic aryl or a tricyclic aryl. The bicyclic aryl is naphthyl, a phenyl fused to a cycloalkyl, or a phenyl fused to a cycloalkenyl. Representative examples of the bicyclic aryl include, but are not limited to, dihydroindenyl, indenyl, naphthyl, dihydronaphthalenyl, and tetrahydronaphthalenyl. The tricyclic aryl is anthracene or phenanthrene, or a bicyclic aryl fused to a cycloalkyl, or a bicyclic aryl fused to a cycloalkenyl, or a bicyclic aryl fused to a phenyl. Representative examples of tricyclic aryl ring include, but are not limited to, azulenyl, dihydroanthracenyl, fluorenyl, and tetrahydrophenanthrenyl.

The aryl groups of this invention can be substituted with 1, 2, 3, 4 or 5 substituents independently selected from alkenyl, alkoxy, alkoxyalkoxy, alkoxyalkoxyalkyl, alkoxyalkyl, alkoxycarbonyl, alkoxycarbonylalkyl, alkyl, alkylcarbonyl, alkylcarbonylalkyl, alkylcarbonyloxy, alkylcarbonyloxyalkyl, alkylsulfinyl, alkylsulfinylalkyl, alkylsulfonyl, alkylsulfonylalkyl, alkylthio, alkylthioalkyl, alkynyl, arylalkyl, arylalkoxy, aryloxy, carboxy, carboxyalkyl, cyano, cyanoalkyl, formyl, formylalkyl, halogen, haloalkyl, haloalkoxy, hydroxy, hydroxyalkyl, mercapto, nitro, —$NZ^1Z^2$, and ($NZ^3Z^4$)carbonyl.

The term "arylalkoxy", as used herein, means an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkyl", as used herein, means an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy", as used herein, means an aryl group, as defined herein, appended to the parent molecular moiety through an oxygen atom. Representative examples of aryloxy include, but are not limited to, phenoxy, naphthyloxy, 3-bromophenoxy, 4-chlorophenoxy, 4-methylphenoxy, and 3,5-dimethoxyphenoxy.

The term "carbonyl", as used herein, means a —C(O)— group.

The term "carboxy", as used herein, means a —$CO_2H$ group.

The term "carboxyalkyl", as used herein, means a carboxy group, as defined herein, appended to the parent molecular moiety through an alkyl group, as defined herein. Representative examples of carboxyalkyl include, but are not limited to, carboxymethyl, 2-carboxyethyl, and 3-carboxypropyl.

The term "cyano", as used herein, means a —CN group.

The term "cyanoalkyl", as used herein, means a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkenyl", as used herein, means a cyclic hydrocarbon containing from 3 to 8 carbons and containing at least one carbon-carbon double bond formed by the removal of two hydrogens. Representative examples of cycloalkenyl include, but are not limited to, 2-cyclohexen-1-yl, 3-cyclohexen-1-yl, 2,4-cyclohexadien-1-yl and 3-cyclopenten-1-yl.

The term "cycloalkyl", as used herein, means a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two adjacent or non-adjacent carbon atoms of the monocyclic ring are linked by an alkylene bridge of between one and three additional carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo[3.3.1.0$^{3,7}$]nonane and tricyclo[3.3.1.1$^{3,7}$]decane (adamantane).

The cycloalkyl groups of the invention are optionally substituted with 1, 2, 3, 4 or 5 substituents selected from the group consisting of alkenyl, alkoxy, alkoxyalkoxy, alkoxyalkyl, alkoxycarbonyl, alkoxysulfonyl, alkyl, alkylcarbonyl, alkylcarbonyloxy, alkylsulfonyl, alkylthio, alkylthioalkyl, alkynyl, carboxy, cyano, formyl, haloalkoxy, haloalkyl, halogen, hydroxy, hydroxyalkyl, mercapto, oxo, —$NZ^1Z^2$, and ($NZ^3Z^4$)carbonyl.

The term "cycloalkylalkyl", as used herein, means a cycloalkyl group, as defined herein, appended to the parent molecular moiety through an alkyl group, as defined herein. Representative examples of cycloalkylalkyl include, but are not limited to, cyclopropylmethyl, 2-cyclobutylethyl, cyclopentylmethyl, cyclohexylmethyl, and 4-cycloheptylbutyl.

The term "formyl", as used herein, means a —C(O)H group.

The term "formylalkyl", as used herein, means a formyl group, as defined herein, appended to the parent molecular moiety through an alkyl group, as defined herein. Representative examples of formylalkyl include, but are not limited to, formylmethyl and 2-formylethyl.

The term "halo" or "halogen", as used herein, means —Cl, —Br, —I or —F.

The term "haloalkoxy", as used herein, means at least one halogen, as defined herein, appended to the parent molecular moiety through an alkoxy group, as defined herein. Representative examples of haloalkoxy include, but are not limited to, chloromethoxy, 2-fluoroethoxy, trifluoromethoxy, and pentafluoroethoxy.

The term "haloalkyl", as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "heteroaryl", as used herein, means a monocyclic heteroaryl or a bicyclic heteroaryl. The monocyclic heteroaryl is a 5 or 6 membered ring that contains at least one heteroatom selected from the group consisting of nitrogen, oxygen and sulfur. The 5 membered ring contains two double bonds and the 6 membered ring contains three double bonds. The 5 or 6 membered heteroaryl is connected to the parent molecular moiety through any carbon atom or any substitutable nitrogen atom contained within the heteroaryl, provided that proper valance is maintained. Representative examples of monocyclic heteroaryl include, but are not limited to, furyl, imidazolyl, isoxazolyl, isothiazolyl, oxadiazolyl, oxazolyl, pyridinyl, pyridazinyl, pyrimidinyl, pyrazinyl, pyrazolyl, pyrrolyl, tetrazolyl, thiadiazolyl, thiazolyl, thienyl, triazolyl, and triazinyl. The bicyclic heteroaryl consists of a monocyclic heteroaryl fused to a phenyl, or a monocyclic heteroaryl fused to a cycloalkyl, or a monocyclic heteroaryl fused to a cycloalkenyl, or a monocyclic heteroaryl fused to a monocyclic heteroaryl. The bicyclic heteroaryl is connected to the parent molecular moiety through any carbon atom or any substitutable nitrogen atom contained within the bicyclic heteroaryl, provided that proper valance is maintained. Representative examples of bicyclic heteroaryl include, but are not limited to, azaindolyl, benzimidazolyl, benzofuranyl, benzoxadiazolyl, benzoisoxazole, benzoisothiazole, benzooxazole, 1,3-benzothiazolyl, benzothiophenyl, cinnolinyl, furopyridine, indolyl, indazolyl, isobenzofuran, isoindolyl, isoquinolinyl, naphthyridinyl, oxazolopyridine, quinolinyl, quinoxalinyl and thienopyridinyl.

The heteroaryl groups of the invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, mercapto, nitro, $-NZ^1Z^2$ and $(NZ^3Z^4)$carbonyl. Heteroaryl groups of the invention that are substituted with a hydroxyl group may be present as tautomers. The heteroaryl groups of the invention encompass all tautomers including non-aromatic tautomers.

The term "heterocycle" or "heterocyclic", as used herein, means a monocyclic heterocycle, a bicyclic heterocycle or a tricyclic heterocycle. The monocyclic heterocycle is a 3, 4, 5, 6 or 7 membered ring containing at least one heteroatom independently selected from the group consisting of O, N, and S. The 3 or 4 membered ring contains 1 heteroatom selected from the group consisting of O, N and S. The 5 membered ring contains zero or one double bond and one, two or three heteroatoms selected from the group consisting of O, N and S. The 6 or 7 membered ring contains zero, one or two double bonds and one, two or three heteroatoms selected from the group consisting of O, N and S. The monocyclic heterocycle is connected to the parent molecular moiety through any carbon atom or any nitrogen atom contained within the monocyclic heterocycle. Representative examples of monocyclic heterocycle include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, piperazinyl, piperidinyl, pyranyl, pyrazolinyl, pyrazolidinyl, pyrrolinyl, pyrrolidinyl, tetrahydrofuranyl, tetrahydrothienyl, thiadiazolinyl, thiadiazolidinyl, thiazolinyl, thiazolidinyl, thiomorpholinyl, 1,1-dioxidothiomorpholinyl(thiomorpholine sulfone), thiopyranyl, and trithianyl. The bicyclic heterocycle is a 5 or 6 membered monocyclic heterocycle fused to a phenyl group, or a 5 or 6 membered monocyclic heterocycle fused to a cycloalkyl, or a 5 or 6 membered monocyclic heterocycle fused to a cycloalkenyl, or a 5 or 6 membered monocyclic heterocycle fused to a monocyclic heterocycle. The bicyclic heterocycle is connected to the parent molecular moiety through any carbon atom or any nitrogen atom contained within the bicyclic heterocycle. Representative examples of bicyclic heterocycle include, but are not limited to, 1,3-benzodioxolyl, 1,3-benzodithiolyl, 2,3-dihydro-1,4-benzodioxinyl, benzodioxolyl, 2,3-dihydro-1-benzofuranyl, 2,3-dihydro-1-benzothienyl, chromenyl and 1,2,3,4-tetrahydroquinolinyl. The tricyclic heterocycle is a bicyclic heterocycle fused to a phenyl, or a bicyclic heterocycle fused to a cycloalkyl, or a bicyclic heterocycle fused to a cycloalkenyl, or a bicyclic heterocycle fused to a monocyclic heterocycle. The tricyclic heterocycle is connected to the parent molecular moiety through any carbon atom or any nitrogen atom contained within the tricyclic heterocycle. Representative examples of tricyclic heterocycle include, but are not limited to, 2,3,4,4a,9,9a-hexahydro-1H-carbazolyl, 5a,6,7,8,9,9a-hexahydrodibenzo[b,d]furanyl, and 5a,6,7,8,9,9a-hexahydrodibenzo[b,d]thienyl.

The heterocycles of this invention are optionally substituted with 1, 2, 3 or 4 substituents independently selected from the group consisting of alkenyl, alkoxy, alkoxyalkoxy, alkoxyalkyl, alkoxycarbonyl, alkoxycarbonylalkyl, alkoxysulfonyl, alkyl, alkylcarbonyl, alkylcarbonylalkyl, alkylcarbonyloxy, alkylthio, alkylthioalkyl, alkynyl, carboxy, carboxyalkyl, cyano, cyanoalkyl, formyl, haloalkoxy, haloalkyl, halogen, hydroxy, hydroxyalkyl, nitro, mercapto, oxo, $-NZ^1Z^2$ and $(NZ^3Z^4)$carbonyl.

The term "hydroxy", as used herein, means an —OH group.

The term "hydroxyalkyl", as used herein, means at least one hydroxy group, as defined herein, is appended to the parent molecular moiety through an alkyl group, as defined herein. Representative examples of hydroxyalkyl include, but are not limited to, hydroxymethyl, 2-hydroxyethyl, 3-hydroxypropyl, 2,3-dihydroxypentyl, and 2-ethyl-4-hydroxyheptyl.

The term "hydroxy-protecting group" or "O-protecting group" means a substituent which protects hydroxyl groups against undesirable reactions during synthetic procedures. Examples of hydroxy-protecting groups include, but are not limited to, substituted methyl ethers, for example, methoxymethyl, benzyloxymethyl, 2-methoxyethoxymethyl, 2-(trimethylsilyl)-ethoxymethyl, benzyl, and triphenylmethyl; tetrahydropyranyl ethers; substituted ethyl ethers, for example, 2,2,2-trichloroethyl and t-butyl; silyl ethers, for example, trimethylsilyl, t-butyldimethylsilyl and t-butyldiphenylsilyl; cyclic acetals and ketals, for example, methylene acetal, acetonide and benzylidene acetal; cyclic ortho esters, for example, methoxymethylene; cyclic carbonates; and cyclic boronates. Commonly used hydroxy-protecting groups are disclosed in T. W. Greene and P. G. M. Wuts, Protective Groups in Organic Synthesis, 3rd edition, John Wiley & Sons, New York (1999).

The term "lower alkenyl", as used herein, is a subset of alkenyl, as defined herein, and means an alkenyl group containing from 2 to 4 carbon atoms. Examples of lower alkenyl are ethenyl, propenyl, and butenyl.

The term "lower alkoxy", as used herein, is a subset of alkoxy, as defined herein, and means a lower alkyl group, as defined herein, appended to the parent molecular moiety through an oxygen atom, as defined herein. Representative examples of lower alkoxy include, but are not limited to, methoxy, ethoxy, propoxy, 2-propoxy, butoxy, and tert-butoxy.

The term "lower alkyl", as used herein, is a subset of alkyl, as defined herein, and means a straight or branched chain hydrocarbon group containing from 1 to 4 carbon atoms.

Examples of lower alkyl are methyl, ethyl, n-propyl, isopropyl, n-butyl, iso-butyl, sec-butyl, and tert-butyl.

The term "lower haloalkoxy", as used herein, is a subset of haloalkoxy, as defined herein, and means a straight or branched chain haloalkoxy group containing from 1 to 4 carbon atoms. Representative examples of lower haloalkoxy include, but are not limited to, trifluoromethoxy, trichloromethoxy, dichloromethoxy, fluoromethoxy, and pentafluoroethoxy.

The term "lower haloalkyl", as used herein, is a subset of haloalkyl, as defined herein, and means a straight or branched chain haloalkyl group containing from 1 to 4 carbon atoms. Representative examples of lower haloalkyl include, but are not limited to, trifluoromethyl, trichloromethyl, dichloromethyl, fluoromethyl, and pentafluoroethyl.

The term "methylenedioxy", as used herein, means a —OCH$_2$O— group wherein the oxygen atoms of the methylenedioxy are attached to the parent molecular moiety through two adjacent carbon atoms.

The term "nitrogen protecting group", as used herein, means those groups intended to protect an amino group against undesirable reactions during synthetic procedures. Preferred nitrogen protecting groups are acetyl, benzoyl, benzyl, benzyloxycarbonyl (Cbz), formyl, phenylsulfonyl, tert-butoxycarbonyl (Boc), tert-butylacetyl, trifluoroacetyl, and triphenylmethyl(trityl).

The term "mercapto", as used herein, means a —SH group.

The term "nitro", as used herein, means a —NO$_2$ group.

The term "NZ$^1$Z$^2$", as used herein, means two groups, Z$^1$ and Z$^2$, which are appended to the parent molecular moiety through a nitrogen atom. Z$^1$ and Z$^2$ are each independently selected from the group consisting of hydrogen, alkyl, alkylcarbonyl, alkoxycarbonyl, aryl, arylalkyl, and formyl. In certain instances within the invention, Z$^1$ and Z$^2$ taken together with the nitrogen atom to which they are attached form a heterocyclic ring. Representative examples of NZ$_1$Z$_2$ include, but are not limited to, amino, methylamino, acetylamino, acetylmethylamino, phenylamino, benzylamino, azetidinyl, pyrrolidinyl and piperidinyl.

The term "NZ$^3$Z$^4$", as used herein, means two groups, Z$^3$ and Z$^4$, which are appended to the parent molecular moiety through a nitrogen atom. Z$^3$ and Z$^4$ are each independently selected from the group consisting of hydrogen, alkyl, aryl and arylalkyl. Representative examples of NZ$^3$Z$^4$ include, but are not limited to, amino, methylamino, phenylamino and benzylamino.

The term "oxo", as used herein, means a =O moiety.

The term "sulfinyl", as used herein, means a —S(O)— group.

The term "sulfonyl", as used herein, means a —SO$_2$— group.

The term "tautomer", as used herein, means a proton shift from one atom of a compound to another atom of the same compound wherein two or more structurally distinct compounds are in equilibrium with each other.

The term "radiolabel" refers to a compound in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

Preparation of Compounds

Preparation of compounds suitable for the composition of the invention can be understood in connection with the following synthetic schemes and examples, which illustrate a means by which the compounds can be prepared. Methods for preparing suitable nicotinic acetylcholine receptor ligands and suitable nicotinic acetylcholine subtype α4β2 allosteric modulators are readily available in the literature. Suitable compounds can be prepared by conventional methods for chemical synthesis with readily available starting materials. Nicotinic acetylcholine receptor ligands and nicotinic acetylcholine subtype α4β2 allosteric modulators also may be commercially available.

Oxadiazole derivatives suitable for the composition of the invention can be prepared according to conventional methods. Some suitable methods for preparing such oxadiazole derivatives are provided in the Schemes and Examples below. However, such further illustration is intended only for reference and is not intended in any way to limit the scope of the invention.

Scheme 1

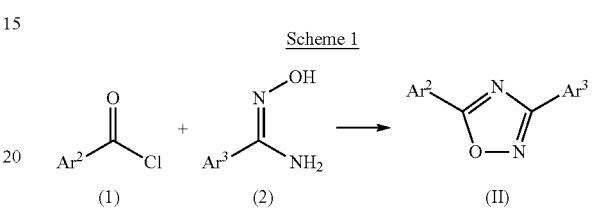

As shown in Scheme 1, compounds of formula (II), wherein Ar$^2$ and Ar$^3$, are as defined in formula (II) above, can be prepared as described in Scheme 1. Aryl or heteroaryl compounds of general formula (1), can be treated with formula (2) with heat in a solvent including, but not limited to pyridine, to provide of general formula (II).

Scheme 2

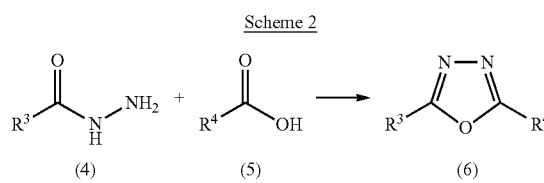

As shown in Scheme 2, compounds of formula (4) can be reacted with compounds of formula (5) in POCl$_3$ at temperatures from 40-100° C. over 1-24 hours to provide compounds of formula (6); wherein R$^3$ is Ar$^1$ and R$^4$ is Y, or R$^3$ is Y and R$^4$ is Ar$^1$. Alternatively, compounds of formula (4) can be reacted with compounds of formula (5) in the presence of triphenylphosphine, which may optionally be polymer bound, and trichloroacetonitrile in acetonitrile. The mixture may be heated in a microwave oven at 100-175° C. for 5-30 minutes as described by Wang, Y.; Sauer, D. R.; Djuric, S. W. Tetrahedron. Lett. 2006, 47, 105-108. Another alternative includes combining compounds of formula (4) and compounds of formula (5) in a solvent such as methylene chloride in the presence of 2-chloro-1,3-dimethylimidazolinium chloride and a base such as triethylamine at 15-35° C. for 10-120 hours as described by Isobe, T.; Ishikawa, T. J. Org. Chem. 1999, 64, 6989-6992.

Scheme 3

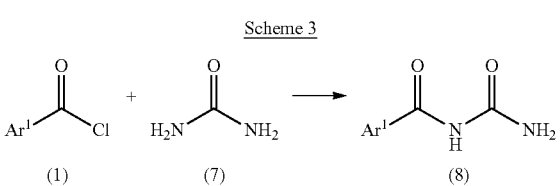

-continued

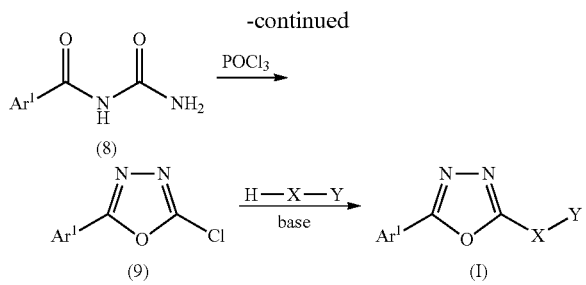

As shown in Scheme 3, compounds of formula (1) can be reacted with urea (7) in a solvent such as dichloromethane in the presence of a base such as triethylamine at 25-40° C. for 1-12 hours to provide compounds of formula (8) as described in Sobol, E.; Bialer, M.; Yagen, B. J. Med. Chem. 2004, 47, 4316-4326. Alternatively, compounds of formula (1) and (7) may be combined in pyridine at 20-110° C. for 1-24 hours to provide compounds of formula (8). Compounds of formula (8) can be treated with $POCl_3$ at 25-100° C. for 1-24 hours to provide compounds of formula (9). Compounds of formula (9) can be reacted with H—X—Y in the presence of a base such as lithium bis(trimethylsilyl)amide, sodium bis(trimethylsilyl)amide, potassium bis(trimethylsilyl)amide, potassium t-butoxide, sodium hydride, potassium carbonate, sodium carbonate, cesium or carbonate in a solvent such as tetrahydrofuran, 1-methyl-2-pyrrolidinone, dimethyl sulfoxide, or acetonitrile at temperatures from −20° C. to 150° C. over 1-48 hours to provide compounds of formula (I).

Scheme 4

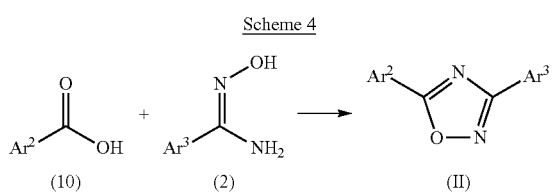

As shown in Scheme 4, compounds of formula (II), wherein $Ar^2$ and $Ar^3$, are as defined in formula (II), can be prepared as described in Scheme 4. Aryl or heteroaryl compounds of general formula (10), can be treated with compounds of formula (2) in the presence of a coupling agent such as N-(3-methylaminopropyl)-N'-ethylcarbodiimide hydrochloride and 1-hydroxybenzotriazole with heat in a solvent including, but not limited to dimethylformamide, to provide compounds of general formula (II).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Compounds and processes suitable for preparing compounds for the composition of the invention will be better understood in connection with the following Examples, which are intended as an illustration of and not a limitation upon the scope of the invention.

Preparation of 2,5-Disubstituted-1,3,4-Oxadiazole Derivatives

Suitable 2,5-disubstituted-1,3,4-oxadiazole derivatives were prepared using readily available starting materials. For example, International Publication WO 02/100826, published Dec. 19, 2002, describes the preparation of some oxadiazole derivatives. However, Compounds of formula (I) also can be prepared according to the following general methods.

Method A:

A carboxylic acid (0.5 mmol) and an acyl hydrazide (0.5 mmol) were combined in $POCl_3$ (2 mL) and stirred at 80-90° C. for 2-4 hours. The reaction mixture was then cooled down to ambient temperature and poured into ice water (10-20 g) and basified with saturated aqueous sodium carbonate to pH=8-9. The resultant precipitate was filtered, dried and purified with chromatography on silica gel to provide the corresponding 2,5-disubstituted-1,3,4-oxadiazole. The free base was then dissolved in EtOAc (5-10 mL) and treated with HCl (Aldrich, 4 M in dioxane, 2-3 eq.) at ambient temperature for 5-10 hours. The precipitate was filtered and dried to provide the corresponding 2,5-disubstituted-1,3,4-oxadiazole hydrochloric acid salt.

Method B:

A Smith Process vial (0.5-2 ml) was charged with a stir bar. To the vessel were added a carboxylic acid (0.1 mmol), nicotinic hydrazide (Aldrich, 13.7 mg, 0.1 mmol), PS-PPh$_3$ (Fluka, 2.2 mmol/g, 136 mg, 0.3 mmol) and MeCN (anhydrous, Aldrich, 2 mL), followed by $CCl_3CN$ (Aldrich, 28.8 mg, 0.20 mmol). The reaction vessel was sealed and heated to 150° C. for 15 minutes using an Emrys™ Optimizer Microwave (Personal Chemistry, www.personalchemistry.com). After cooling, the reaction vessel was uncapped and the resin was removed by filtration. The mixture was purified by preparative HPLC [Waters, column: Nova-Pak® HR C18 6 μm 60 Å Prep-Pak® (25 mm×100 mm), solvent: MeCN/water (v.1% TFA), 5/95 to 95/5, flow rate of 40 mL/min. Fractions were collected based upon UV signal threshold, and selected fractions were subsequently analyzed by flow injection analysis mass spectrometry using positive APCI ionization on a Finnigan LCQ using 70:30 MeOH:10 mM $NH_4OH$(aq) at a flow rate of 0.8 mL/min.]. Some mixtures were purified by an alternative preparative HPLC method [Waters, column: Sunfire OBD C8 5 μm (30 mm×75 mm); solvent: MeCN/10 mM aqueous ammonium acetate, 10/90 to 100/0; flow rate of 50 mL/min. Fractions were collected based upon target mass signal threshold, and selected fractions were subsequently analyzed by flow injection analysis mass spectrometry using the previously described method.].

Preparation of 3,5-Disubstituted-1,2,4-Oxadiazole Derivatives

Preparation of suitable oxadiazole derivatives are of particular interest. Many oxadiazole derivatives are suitable nicotinic acetylcholine subtype α4β2 positive allosteric modulators for the composition. Preparation of oxadiazole derivatives has been described in the literature. For example, WO 2006/114400, published Nov. 2, 2006, discloses that oxadiazole derivatives can be readily prepared. International Publication WO 02/100826, published Dec. 19, 2002, also describes the preparation of other oxadiazole derivatives.

Example 1

3-(3-(pyridin-3-yl)-1,2,4-oxadiazol-5-yl)benzonitrile

3-Pyridylamideoxime (Aldrich, 5.5 g, 40 mmol) was dissolved in 60 mL of pyridine and 3-cyanobenzoyl chloride (Aldrich, 6.6 g, 40 mmol) was added. The reaction mixture was heated to reflux for 4 hours and then cooled to room temperature. The solution was poured into water (500 mL), filtered, and the solid were collected and dried under vacuum. $^1$H NMR (300 MHz, methanol-$d_4$) δ ppm 7.87 (td, J=8.0, 0.7 Hz, 1H), 8.10 (dt, J=8.1, 1.4 Hz, 1H), 8.23 (ddd, J=8.1, 5.6, 0.8 Hz, 1H), 8.56 (ddd, J=8.0, 1.7, 1.2 Hz, 1H), 8.64 (td, J=1.7, 0.7 Hz, 1H), 9.04 (dd, J=5.4, 1.0 Hz, 1H), 9.23 (dt, J=8.1, 1.7 Hz, 1H), 9.57 (d, J=1.7 Hz, 1H); MS (+ESI) m/z 249 (M+H)$^+$.

Example 2

3,5-di(pyridin-3-yl)-1,2,4-oxadiazole

3-Pyridylamideoxime (5.5 g, 40 mmol) was dissolved in 60 mL of pyridine and nicotinoyl chloride hydrochloride (7.2 g, 40 mmol) was added. The reaction mixture was heated to reflux for 4 hours and then cooled to room temperature. The solution was poured into water (500 mL), basified, filtered, and the solid was collected and dried under vacuum. $^1$H NMR (300 MHz, DMSO-$d_6$) δ 7.75-7.65 (m, 2H), 8.49-8.45 (m, 1H), 8.60-8.57 (m, 1H), 8.84-8.82 (dd, J=1.7 Hz, 1H), 8.92-8.90 (dd, J=1.7 Hz, 1H), 9.28 (m, 1H), 9.37 (m, 1H); MS (DCl/NH$_3$) m/z 225 (M+H)$^+$.

Example 3

3-(5-(pyridin-3-yl)-1,2,4-oxadiazol-3-yl)benzonitrile

Example 3A

3-Cyano-N'-hydroxybenzimidamide

Hydroxylamine (Aldrich, 7.65 g, 100 mmol) in ethanol (100 mL) was treated with 10 N sodium hydroxide (10 mL, 100 mmol). To this solution, isophthalonitrile (Aldrich, 12.8 g, 100 mmol) in 100 mL ethanol was added. The reaction mixture was heated to reflux for 3 hours and then cooled to room temperature. The solvent was removed under vacuum and the residue was purified with flash column chromatography (5% methanol/dichloromethane) to provide the titled compound. $^1$H NMR (300 MHz, DMSO-$d_6$) δ 5.98 (bs, 2H), 7.59 (t, J=7.4 Hz, 1H), 8.06-8.0 (m, 2H), 9.89 (s, 1H) ppm; MS (DCl/NH$_3$) m/z 162 (M+H)$^+$.

Example 3B

3-(5-(pyridin-3-yl)-1,2,4-oxadiazol-3-yl)benzonitrile

3-Cyano-N'-hydroxybenzimidamide (0.322 g, 1 mmol) was dissolved in pyridine (10 mL) and nicotinoyl chloride (Aldrich, 0.141 g, 1 mmol) was added. The reaction mixture was heated to reflux for 3 hours and cooled to room temperature. The cooled reaction mixture was quenched with water (25 mL) and filtered. The solid was further purified with flash column chromatography (5% methanol/dichloromethane) to give the titled compound. $^1$H NMR (300 MHz, DMSO-$d_6$) δ 7.75-7.71 (dd, J=5.7, 4.1 Hz, 1H), 7.85 (t, J=7.8 Hz, 1H), 8.15-8.12 (d, J=7.8 Hz, 1H) 8.44-8.42 (m, 1H), 8.50 (m, 1H), 8.60-8.56 (m, 1H), 8.93-8.91 (dd, J=1.7 Hz, 1H), 9.37-9.38 (d, J=1.7 Hz, 1H) ppm; MS (DCl/NH$_3$) m/z 249 (M+H)$^+$.

Example 4

3-(5-(6-fluoropyridin-3-yl)-1,2,4-oxadiazol-3-yl) benzonitrile

Example 4A

3-Cyano-N'-hydroxybenzimidamide

Hydroxylamine (Aldrich, 7.65 g, 100 mmol) in ethanol (100 mL) was treated with 10 N NaOH (10 mL, 100 mmol). To this solution, isophthalonitrile (Aldrich, 12.8 g, 100 mmol) in 100 mL of ethanol was added. The reaction mixture was heated to reflux for 3 hours and then cooled to room temperature. The solvent was removed under vacuum and the residue was purified with flash column chromatography (5% methanol/dichloromethane) to give the titled product. $^1$H NMR (300 MHz, DMSO-$d_6$) δ 5.98 (bs, 2H), 7.59 (t, J=7.4 Hz, 1H), 8.06-8.0 (m, 2H), 9.89 (s, 1H) ppm; MS (DCl/NH$_3$) m/z 162 (M+H)$^+$.

Example 4B

3-(5-(6-fluoropyridin-3-yl)-1,2,4-oxadiazol-3-yl) benzonitrile

3-Cyano-N'-hydroxybenzimidamide (0.322 g, 1 mmol) was dissolved in pyridine 10 mL and 6-fluoronicotinoyl chloride (Frontier Scientific, 0.160 g, 1 mmol) was added. The reaction mixture was heated to reflux for 3 hours and then cooled to room temperature. The cooled reaction mixture was quenched with water (25 mL) and filtered. The solid was further purified with flash column chromatography (5% methanol/dichloromethane) to give the titled product. $^1$H NMR (300 MHz, DMSO-$d_6$) δ 7.56-7.52 (m, 1H), 7.85 (t, J=7.9 Hz, 1H), 8.15-8.12 (m, 1H), 8.43-8.41 (m, 1H), 8.49 (m, 1H), 8.8-8.74 (m, 1H), 9.11-9.0 (m, 1H) ppm; MS (DCl/NH$_3$) m/z 267 (M+H)$^+$.

Example 5

5-(5-bromopyridin-3-yl)-3-(pyridin-3-yl)-1,2,4-oxadiazole

The title compound was prepared according to the procedure of Example 1 using N'-hydroxynicotinimidamide (Aldrich) and 5-bromonicotinoyl chloride (Alfa). $^1$H NMR (300 MHz, DMSO-$d_6$) δ 8.65-8.69 (m, 1H), 8.45-8.49 (m, 1H), 8.79 (t, J=1.7 Hz, 1H), 8.84 (dd, J=1.7, 2.0 Hz, 1H), 9.07 (d, J=2 Hz, 1H), 9.28-9.29 (m, 1H), 9.34 (d, J=1.7 Hz, 1H) ppm; MS (DCl/NH$_3$) m/z 303 (M+H)$^+$.

Example 6

3-(pyridin-3-yl)-5-(3-(trifluoromethylsulfonyl)phenyl)-1,2,4-oxadiazole

Example 6A

3-(trifluoromethylsulfonyl)benzoic acid

A solution of 3-(trifluoromethylthio)benzoic acid (222 mg, 1 mmol) in dichloromethane (10 mL) was stirred with chromium(VI) oxide (Aldrich, 2.0 mmol) at ambient temperature for 12 hours. The title compound was obtained by directly loading the reaction mixture onto a silica gel column and eluting with dichloromethane/methanol (9:1). $^1$H NMR (300 MHz, DMSO-d$_6$) δ 8.8 (s, 1H), 8.28 (m, 1H), 8.05 (m, 1H), 7.9 (m, 1H) ppm; MS (DCl/NH$_3$) m/z 255 (M+H)$^+$.

Example 6B 3-(trifluoromethylsulfonyl)benzoyl chloride

A solution of the product of Example 6A (198 mg, 0.8 mmol) in dichloromethane (10 mL) was stirred with oxalyl dichloride (Aldrich, 2.0 mmol) and 1 drop of dimethylformamide at ambient temperature for 2 hours. The title compound was obtained by removing the solvent under vacuum as a yellow oil (250 mg) and the compound was used directly in the next step.

Example 6C 3-(pyridin-3-yl)-5-(3-(trifluoromethylsulfonyl)phenyl)-1,2,4-oxadiaole The title compound was prepared according to the procedure of Example 1 using N'-hydroxynicotinimidamide (Aldrich) and the compound of Example 6B. $^1$H NMR (300 MHz, DMSO-d$_6$) δ 7.73 (dd, J=4, 5.0 Hz, 1H), 7.85 (t, J=8 Hz, 1H), 8.13 (m, 1H), 8.43 (m, 1H) 8.5 (m, 1H), 8.6 (m, 1H), 8.92 (m, 1H), 9.37 (m, 1H) ppm; MS (DCl/NH$_3$) m/z 356 (M+H)$^+$.

Example 7

3-(3-(6-methylpyridin-3-yl)-1,2,4-oxadiazol-5-yl)benzonitrile

Example 7A

N'-hydroxy-6-methylnicotinimidamide

Hydroxylamine (Aldrich, 0.765 g, 10 mmol) in ethanol (10 mL) was treated with a solution 6-methylnicotinonitrile (Aldrich, 12.8 g, 100 mmol) in ethanol (10 mL). The reaction mixture was heated to reflux for 3 hours and then cooled to room temperature. The solvent was removed under vacuum and the residue was purified with flash column chromatography (5% methanol/dichloromethane) give the titled compound. $^1$H NMR (300 MHz, DMSO-d$_6$) δ 2.2 (s, 3H), 6.02 (bs, 2H), 7.59 (m, 1H), 8.06-8.0 (m, 2H), 10.2 (s, 1H) ppm; MS (DCl/NH$_3$) m/z 152 (M+H)$^+$.

Example 7B 3-(3-(6-methylpyridin-3-yl)-1,2,4-oxadiazol-5-yl)benzonitrile

The titled compound was prepared according to the procedure of Example 1 using N'-hydroxynicotinimidamide (Example 7A) and 3-cyanobenzoyl chloride (Aldrich). $^1$H NMR (300 MHz, DMSO-d$_6$) δ 2.59 (s, 3H), 7.52 (d, J=8.1 Hz, 1H), 7.39 (t, J=8.5 Hz, 1H), 8.23-8.21 (m, 1H), 8.36-8.32 (m, 1H), 8.53-8.49 (m, 1H), 8.64 (m, 1H), 9.14 (m, 1H), ppm; MS (DCl/NH$_3$) m/z 263 (M+H)$^+$.

Example 8

5-(5-(pyrrol-1-yl)pyridin-3-yl)-3-(pyridin-3-yl)-1,2,4-oxadiazole

To a solution of 5-(1H-pyrrol-1-yl)nicotinic acid (Maybridge, 188 mg, 1.00 mmol) in dimethylformamide (anhydrous, 5 mL) was added N-(3-methylaminopropyl)-N'-ethylcarbodiimide hydrochloride (EDC) (Aldrich, 192 mg, 1.00 mmol) and 1-hydroxybenzotriazole (HOBT) hydrate (Fluka, 153 mg, 1.00 mmol). The mixture was stirred at ambient temperature for 20 minutes. N'-Hydroxynicotinimidamide (137 mg, 1.0 mmol) was added and the mixture was stirred for 6-10 hours, and then warmed to 140° C. for 2-4 hours. The reaction was cooled to ambient temperature and triturated with water (10 mL). The precipitate was filtered and dried under vacuum to give the titled compound. $^1$H NMR (300 MHz, DMSO-d6) δ 6.34-6.44 (m, 2H), 7.60-7.82 (m, 3H), 8.50 (dt, J=8.1, 1.9 Hz, 1H), 8.71 (dd, J=2.5, 1.9 Hz, 1H), 8.84 (dd, J=4.6, 1.5 Hz, 1H), 9.21 (d, J=1.7 Hz, 1H), 9.26 (d, J=2.4 Hz, 1H), 9.31 (d, J=1.7 Hz, 1H) ppm; MS (DCl/NH3) m/z 290 (M+H)$^+$.

Example 9

5-(3-(pyridin-3-yl)-1,2,4-oxadiazol-5-yl)pyridin-3-ol

The title compound was prepared according to the procedure of Example 8 using N'-hydroxynicotinimidamide (Aldrich) and 5-hydroxynicotinic acid (Matrix Scientific). $^1$H NMR (300 MHz, DMSO-d$_6$) δ 7.66 (ddd, J=8.0, 4.9, 1.0 Hz, 1H), 7.86 (dd, J=2.7, 2.0 Hz, 1H), 8.31-8.55 (m, 2H), 8.83 (s, 2H), 9.26 (s, 1H) ppm; MS (DCl/NH$_3$) m/z 241 (M+H)$^+$.

Example 10

5-(3,4-difluorophenyl)-3-(pyridin-3-yl)-1,2,4-oxadiazole

The title compound was prepared according to the procedure of Example 8 using N'-hydroxynicotinimidamide (Aldrich) and 3,4-difluorobenzoic acid (Aldrich). $^1$H NMR (300 MHz, CD$_3$OD) δ 7.52-7.67 (m, 2H), 8.12 (ddd, J=8.7, 4.3, 1.5 Hz, 1H), 8.19 (ddd, J=10.8, 7.5, 2.0 Hz, 1H), 8.55 (dt, J=8.1, 1.9 Hz, 1H), 8.74 (dd, J=5.1, 1.7 Hz, 1H), 9.29 (dd, J=2.0, 0.7 Hz, 1H) ppm; MS (DCl/NH$_3$) m/z 260 (M+H)$^+$.

Example 11

5-(2,3-difluorophenyl)-3-(pyridin-3-yl)-1,2,4-oxadiazole

The title compound was prepared according to the procedure of Example 8 using N'-hydroxynicotinimidamide (Aldrich) and 2,3-difluorobenzoic acid (Aldrich). $^1$H NMR (300 MHz, CD$_3$OD) δ 7.51-7.67 (m, 2H), 8.08-8.14 (m, 1H), 8.18 (ddd, J=10.7, 7.5, 2.0 Hz, 1H), 8.55 (dt, J=8.0, 1.9 Hz, 1H), 8.74 (dd, J=5.2, 1.6 Hz, 1H), 9.29 (dd, J=2.4, 0.8 Hz, 1H) ppm; MS (DCl/NH$_3$) m/z 260 (M+H)$^+$.

Example 12

5-(pyrazin-2-yl)-3-(pyridin-3-yl)-1,2,4-oxadiazole

The titled compound was prepared according to the procedure of Example 8 using N'-hydroxynicotinimidamide (Aldrich) and pyrazine-2-carboxylic acid (Aldrich). $^1$H NMR (300 MHz, CD$_3$OD) δ 7.66 (ddd, J=8.0, 4.9, 1.0 Hz, 1H), 8.60 (dt, J=8.0, 1.9 Hz, 1H), 8.77 (dd, J=5.0, 1.8 Hz, 1H), 8.86-

8.89 (m, 1H), 8.89-8.91 (m, 1H), 9.34 (dd, J=2.4, 0.8 Hz, 1H), 9.56 (d, J=1.6 Hz, 1H) ppm; MS (DCl/NH₃) m/z 226 (M+H)⁺.

Example 13

5-(3,5-difluorophenyl)-3-(pyridin-3-yl)-1,2,4-oxadiazole

The title compound was prepared according to the procedure of Example 8 using N'-hydroxynicotinimidamide (Aldrich) and 3,5-difluorobenzoic acid (Aldrich). ¹H NMR (300 MHz, CD₃OD) δ 7.37 (tt, J=9.0, 2.3 Hz, 1H), 7.65 (ddd, J=7.9, 5.0, 1.0 Hz, 1H), 7.82-7.91 (m, 2H), 8.56 (dt, J=7.9, 2.0 Hz, 1H), 8.75 (dd, J=4.8, 1.6 Hz, 1H), 9.30 (dd, J=2.0, 0.8 Hz, 1H) ppm; MS (DCl/NH₃) m/z 260 (M+H)⁺.

Example 14

5-(2,3,5-trifluorophenyl)-3-(pyridin-3-yl)-1,2,4-oxadiazole

The title compound was prepared according to the procedure of Example 8 using N'-hydroxynicotinimidamide (Aldrich) and 2,3,5-trifluorobenzoic acid (Aldrich). ¹H NMR (300 MHz, CD₃OD) δ 7.55-7.68 (m, 2H), 7.83-7.90 (m, 1H), 8.57 (dt, J=8.1, 1.9 Hz, 1H), 8.75 (dd, J=5.1, 1.7 Hz, 1H), 9.30 (dd, J=2.2, 0.8 Hz, 1H) ppm; MS (DCl/NH₃) m/z 278 (M+H)⁺.

Example 15

5-(2,4,5-trifluorophenyl)-3-(pyridin-3-yl)-1,2,4-oxadiazole

The title compound was prepared according to the procedure of Example 8 using N'-hydroxynicotinimidamide (Aldrich) and 2,4,5-trifluorobenzoic acid (Aldrich). ¹H NMR (300 MHz, CD₃OD) δ 7.55 (td, J=10.3, 6.4 Hz, 1H), 7.64 (ddd, J=8.1, 5.0, 0.8 Hz, 1H), 8.23 (ddd, J=10.3, 8.6, 6.4 Hz, 1H), 8.56 (dt, J=8.1, 1.9 Hz, 1H), 8.75 (dd, J=5.1, 1.7 Hz, 1H), 9.29 (d, J=1.4 Hz, 1H) ppm; MS (DCl/NH₃) m/z 278 (M+H)⁺.

Example 16

5-(2,5-difluorophenyl)-3-(pyridin-3-yl)-1,2,4-oxadiazole

The title compound was prepared according to the procedure of Example 8 using N'-hydroxynicotinimidamide (Aldrich) and 2,5-difluorobenzoic acid (Aldrich). ¹H NMR (300 MHz, CD₃OD) δ 7.41-7.56 (m, 2H), 7.65 (ddd, J=7.9, 5.0, 1.0 Hz, 1H), 7.98-8.04 (m, 1H), 8.57 (dt, J=8.0, 1.9 Hz, 1H), 8.75 (dd, J=5.2, 1.6 Hz, 1H), 9.31 (dd, J=2.0, 0.8 Hz, 1H); MS (DCl/NH₃) m/z 260 (M+H)⁺.

Example 17

5-(4-chloro-2,5-difluorophenyl)-3-(pyridin-3-yl)-1,2,4-oxadiazole

The title compound was prepared according to the procedure of Example 8 using N'-hydroxynicotinimidamide (Aldrich) and 4-chloro-2,5-difluorobenzoic acid (Aldrich). ¹H NMR (300 MHz, CD₃OD) δ 7.65 (ddd, J=8.0, 4.9, 1.0 Hz, 1H), 7.73 (dd, J=9.7, 5.9 Hz, 1H), 8.18 (dd, J=8.8, 6.1 Hz, 1H), 8.57 (dt, J=8.1, 1.9 Hz, 1H), 8.75 (dd, J=4.7, 1.7 Hz, 1H), 9.30 (dd, J=2.2, 0.8 Hz, 1H) ppm; MS (DCl/NH₃) m/z 294 (M+H)⁺.

Example 18

5-(5-methylpyrazin-2-yl)-3-(pyridin-3-yl)-1,2,4-oxadiazole

The title compound was prepared according to the procedure of Example 8 using N'-hydroxynicotinimidamide (Aldrich) and 5-methylpyrazine-2-carboxylic acid (Aldrich). ¹H NMR (300 MHz, CD₃OD) δ 2.71 (s, 3H), 7.66 (ddd, J=8.0, 5.1, 0.8 Hz, 1H), 8.59 (dt, J=7.9, 1.8 Hz, 1H), 8.74-8.78 (m, 2H), 9.33 (dd, J=2.0, 0.8 Hz, 1H), 9.40 (d, J=1.2 Hz, 1H) ppm; MS (DCl/NH₃) m/z 240 (M+H)⁺.

Example 19

4-(3-(pyridin-3-yl)-1,2,4-oxadiazol-5-yl)benzonitrile

The title compound was prepared according to the procedure of Example 1 using N'-hydroxynicotinimidamide (Aldrich) and 4-cyanobenzoyl chloride (Aldrich). ¹H NMR (300 MHz, CD₃OD) δ 7.65 (ddd, J=8.0, 4.9, 1.0 Hz, 1H), 8.02 (d, J=8.8 Hz, 2H), 8.42 (d, J=8.8 Hz, 2H), 8.57 (dt, J=8.1, 1.9 Hz, 1H), 8.75 (dd, J=4.7, 1.7 Hz, 1H), 9.31 (dd, J=2.2, 0.8 Hz, 1H) ppm; MS (DCl/NH₃) m/z 249 (M+H)⁺.

Example 20

2,3,6-trifluoro-5-(3-(pyridin-3-yl)-1,2,4-oxadiazol-5-yl)phenol

The title compound was prepared according to the procedure of Example 8 using N'-hydroxynicotinimidamide (Aldrich) and 2,4,5-trifluoro-3-hydroxybenzoic acid (Aldrich). ¹H NMR (300 MHz, CD₃OD) δ 7.63-7.76 (m, 2H), 8.44 (dt, J=7.9, 2.0 Hz, 1H), 8.83 (dd, J=4.8, 1.6 Hz, 1H), 9.25 (d, J=1.6 Hz, 1H) ppm; MS (DCl/NH₃) m/z 294 (M+H)⁺.

Example 21

2-fluoro-5-(3-(pyridin-3-yl)-1,2,4-oxadiazol-5-yl)phenol

The title compound was prepared according to the procedure of Example 8 using N'-hydroxynicotinimidamide (Aldrich) and 4-fluoro-3-hydroxybenzoic acid (Aldrich). ¹H NMR (300 MHz, DMSO-d₆) δ 7.45 (dd, J=11.1, 8.7 Hz, 1H), 7.62-7.71 (m, 2H), 7.78 (dd, J=8.3, 2.0 Hz, 1H), 8.43 (dt, J=7.9, 1.8 Hz, 1H), 8.82 (dd, J=5.0, 1.8 Hz, 1H), 9.24 (d, J=2.0 Hz, 1H) ppm; MS (DCl/NH₃) m/z 258 (M+H)⁺.

Example 22

2-fluoro-4-(3-(pyridin-3-yl)-1,2,4-oxadiazol-5-yl)phenol

The title compound was prepared according to the procedure of Example 8 using N'-hydroxynicotinimidamide (Aldrich) and 3-fluoro-4-hydroxybenzoic acid (Aldrich). ¹H NMR (300 MHz, CD₃OD) δ 7.09 (t, J=8.7 Hz, 1H), 7.63 (ddd, J=7.9, 5.2, 0.8 Hz, 1H), 7.86-7.93 (m, 2H), 8.53 (dt, J=7.9, 2.0 Hz, 1H), 8.72 (dd, J=4.8, 1.6 Hz, 1H), 9.27 (dd, J=2.4, 0.8 Hz, 1H) ppm; MS (DCl/NH₃) m/z 258 (M+H)⁺.

Example 23

5-(3-chloro-4-fluorophenyl)-3-(pyridin-3-yl)-1,2,4-oxadiazole

The title compound was prepared according to the procedure of Example 8 using N'-hydroxynicotinimidamide (Aldrich) and 3-chloro-4-fluorobenzoic acid (Aldrich). $^1$H NMR (300 MHz, CD$_3$OD) δ 7.54 (t, J=8.8 Hz, 1H), 7.64 (ddd, J=8.1, 5.0, 0.8 Hz, 1H), 8.24 (ddd, J=8.6, 4.6, 2.0 Hz, 1H), 8.39 (dd, J=7.0, 2.2 Hz, 1H), 8.55 (dt, J=8.1, 1.9 Hz, 1H), 8.74 (dd, J=4.9, 1.5 Hz, 1H), 9.29 (dd, J=2.2, 0.8 Hz, 1H) ppm; MS (DCl/NH$_3$) m/z 276 (M+H)$^+$.

Example 24

5-(3,4-dichlorophenyl)-3-(pyridin-3-yl)-1,2,4-oxadiazole

The title compound was prepared according to the procedure of Example 8 using N'-hydroxynicotinimidamide (Aldrich) and 3,4-dichlorobenzoic acid (Aldrich). $^1$H NMR (300 MHz, CD$_3$OD) δ 7.64 (ddd, J=8.0, 5.1, 0.8 Hz, 1H), 7.82 (d, J=8.3 Hz, 1H), 8.14-8.19 (m, 1H), 8.40 J=2.0 Hz, 1H), 8.56 (dt, J=7.9, 2.0 Hz, 1H), 8.75 (dd, J=5.2, 1.6 Hz, 1H), 9.29 (dd, J=2.2, 1.0 Hz, 1H) ppm; MS (DCl/NH$_3$) m/z 292 (M+H)$^+$.

Example 25

2-nitro-5-(3-(pyridin-3-yl)-1,2,4-oxadiazol-5-yl)phenol

The title compound was prepared according to the procedure of Example 8 using N'-hydroxynicotinimidamide (Aldrich) and 3-hydroxy-4-nitrobenzoic acid (Maybridge). $^1$H NMR (300 MHz, DMSO-d$_6$) δ 6.51 (d, J=9.1 Hz, 1H), 6.92-7.31 (s (broad), 1H), 7.61 (ddd, J=7.9, 4.8, 0.8 Hz, 1H), 7.68 (dd, J=9.1, 2.4 Hz, 1H), 8.40 (dt, J=7.9, 2.0 Hz, 1H), 8.53 (d, J=2.4 Hz, 1H), 8.77 (dd, J=4.8, 1.6 Hz, 1H), 9.20 (d, J=1.6 Hz, 1H) ppm; MS (DCl/NH$_3$) m/z 285 (M+H)$^+$.

Example 26

5-(2,3,6-trifluorophenyl)-3-(pyridin-3-yl)-1,2,4-oxadiazole

The title compound was prepared according to the procedure of Example 8 using N'-hydroxynicotinimidamide (Aldrich) and 2,3,6-trifluorobenzoic acid (Aldrich). $^1$H NMR (300 MHz, CD$_3$OD) δ 7.26-7.35 (m, J=9.4, 9.4, 3.8, 2.0 Hz, 1H), 7.62-7.77 (m, 2H), 8.57 (dt, J=8.0, 1.9 Hz, 1H), 8.76 (dd, J=4.8, 1.6 Hz, 1H), 9.30 (dd, J=2.4, 0.8 Hz, 1H) ppm; MS (DCl/NH$_3$) m/z 278 (M+H)$^+$.

Example 27

2,2,2-trifluoro-1-(4-(3-(pyridin-3-yl)-1,2,4-oxadiazol-5-yl)phenyl)ethanone trifluoroacetate The title compound was prepared according to the procedure of Example 8 using N'-hydroxynicotinimidamide (Aldrich) and 4-(2,2,2-trifluoroacetyl)benzoic acid (Aldrich). $^1$H NMR (300 MHz, CD$_3$OD) δ 7.81 (ddd, J=7.9, 5.2, 0.8 Hz, 1H), 7.96 (d, J=8.3 Hz, 2H), 8.28 (d, J=8.7 Hz, 2H), 8.76 (dt, J=8.2, 1.8 Hz, 1H), 8.82 (dd, J=5.2, 1.6 Hz, 1H), 9.38 (d, J=1.6 Hz, 1H) ppm; MS (DCl/NH$_3$) m/z 320 (M+H)$^+$.

Example 28

5-(3-fluorophenyl)-3-(pyridin-3-yl)-1,2,4-oxadiazole

The title compound was prepared according to the procedure of Example 8 using N'-hydroxynicotinimidamide (Aldrich) and 3-fluorobenzoic acid (Aldrich). $^1$H NMR (300 MHz, CD$_3$OD) δ 7.43-7.51 (m, J=8.5, 8.5, 2.6, 1.0 Hz, 1H), 7.61-7.72 (m, 2H), 7.98 (ddd, J=9.1, 2.6, 1.4 Hz, 1H), 8.08 (ddd, J=8.0, 1.3, 1.0 Hz, 1H), 8.56 (dt, J=8.0, 1.9 Hz, 1H), 8.74 (dd, J=5.2, 1.6 Hz, 1H), 9.30 (dd, J=2.0, 0.8 Hz, 1H) ppm; MS (DCl/NH$_3$) m/z 242 (M+H)$^+$.

Example 29

5-(4-fluorophenyl)-3-(pyridin-3-yl)-1,2,4-oxadiazole

The title compound was prepared according to the procedure of Example 8 using N'-hydroxynicotinimidamide (Aldrich) and 4-fluorobenzoic acid (Aldrich). $^1$H NMR (300 MHz, CD$_3$OD) δ 7.39 (t, J=8.9 Hz, 2H), 7.64 (ddd, J=7.9, 4.8, 0.8 Hz, 1H), 8.27-8.35 (m, 2H), 8.55 (ddd, J=8.1, 2.0, 1.8 Hz, 1H), 8.74 (dd, J=5.0, 1.8 Hz, 1H), 9.29 (dd, J=2.2, 1.0 Hz, 1H) ppm; MS (DCl/NH$_3$) m/z 242 (M+H)$^+$.

Example 30

5-(2-fluorophenyl)-3-(pyridin-3-yl)-1,2,4-oxadiazole

The title compound was prepared according to the procedure of Example 8 using N'-hydroxynicotinimidamide (Aldrich) and 2-fluorobenzoic acid (Aldrich). $^1$H NMR (300 MHz, CD$_3$OD) δ 7.38-7.49 (m, 2H), 7.64 (ddd, J=8.0, 4.9, 1.0 Hz, 1H), 7.70-7.79 (m, 1H), 8.28 (td, J=7.5, 1.9 Hz, 1H), 8.57 (dt, J=8.1, 1.9 Hz, 1H), 8.74 (dd, J=4.7, 1.7 Hz, 1H), 9.31 (dd, J=2.2, 0.8 Hz, 1H) ppm; MS (DCl/NH$_3$) m/z 242 (M+H)$^+$.

Example 31

3-fluoro-5-(3-(pyridin-3-yl)-1,2,4-oxadiazol-5-yl)benzonitrile

The title compound was prepared according to the procedure of Example 8 using N'-hydroxynicotinimidamide (Aldrich) and 3-cyano-5-fluorobenzoic acid (Aldrich). $^1$H NMR (300 MHz, CD$_3$OD) δ 7.65 (ddd, J=8.0, 5.1, 0.8 Hz, 1H), 7.95 (ddd, J=8.1, 2.6, 1.6 Hz, 1H), 8.32 (ddd, J=8.7, 2.6, 1.4 Hz, 1H), 8.46 (t, J=1.4 Hz, 1H), 8.58 (ddd, J=8.1, 2.0, 1.8 Hz, 1H), 8.76 (dd, J=5.2, 1.6 Hz, 1H), 9.31 (dd, J=2.0, 0.8 Hz, 1H) ppm; MS (DCl/NH$_3$) m/z 267 (M+H)$^+$.

Example 32

3-(2,3-difluorophenyl)-5-(pyridin-3-yl)-1,2,4-oxadiazole hydrochloric acid

Example 32A 3-(2,3-difluorophenyl)-5-(pyridin-3-yl)-1,2,4-oxadiazole

The title compound was prepared according to the procedure of Example 1 using 2,3-difluoro-N'-hydroxybenzimidamide (Tyger Scientific) and nicotinoyl chloride hydrochloride (Aldrich). $^1$H NMR (300 MHz, DMSO-d$_6$) δ 7.42-7.61 (m, 1H), 7.67-7.85 (m, 2H), 7.91-8.04 (m, 1H), 8.57 (dt, J=8.1, 1.9 Hz, 1H), 8.92 (dd, J=4.8, 1.6 Hz, 1H), 9.36 (dd, J=2.4, 0.8 Hz, 1H) ppm; MS (DCl/NH$_3$) m/z 260 (M+H)$^+$.

Example 32B 3-(2,3-difluorophenyl)-5-(pyridin-3-yl)-1,2,4-oxadiazole hydrochloric acid A solution of the product of Example 32A (320 mg, 1.23 mmol) in ethyl acetate (5 mL) was stirred with hydrochloric acid (Aldrich, 4 M in dioxane, 0.5 mL, 2.0 mmol) at ambient temperature for 4 hours. The titled compound was collected by filtration and dried under vacuum. $^1$H NMR (300 MHz, MeOH-d$_4$) δ 7.35-7.46 (m, 1H), 7.49-7.63 (m, 1H), 7.93-8.07 (m, 1H), 8.24 (dd, J=8.1, 5.8 Hz, 1H), 9.10 (dd, J=5.8, 1.4 Hz, 1H), 9.23 (dt, J=8.0, 1.8 Hz, 1H), 9.66 (d, J=2.0 Hz, 1H) ppm; MS (DCl/NH$_3$) m/z 260 (M+H)$^+$.

Example 33

3-(3,4-difluorophenyl)-5-(pyridin-3-yl)-1,2,4-oxadiazole hydrochloric acid

Example 33A 3-(3,4-difluorophenyl)-5-(pyridin-3-yl)-1,2,4-oxadiazole

The title compound was prepared according to the procedure of Example 1 using 3,4-difluoro-N'-hydroxybenzimidamide (Tyger Scientific) and nicotinoyl chloride hydrochloride (Aldrich). $^1$H NMR (300 MHz, DMSO-d$_6$) δ 7.74 (dd, J=7.5, 4.4 Hz, 1H), 8.60 (dt, J=7.8, 2.1 Hz, 1H), 8.93 (dd, J=4.8, 1.6 Hz, 1H), 9.38 (dd, J=2.2, 1.0 Hz, 1H), 9.44-9.48 (m, 3H) ppm; MS (DCl/NH$_3$) m/z 260 (M+H)$^+$.

Example 33B 3-(3,4-difluorophenyl)-5-(pyridin-3-yl)-1,2,4-oxadiazole hydrochloric acid A solution of the product of Example 32A (280 mg, 1.08 mmol) in ethyl acetate (5 mL) was stirred with hydrochloric acid (Aldrich, 4 M in dioxane, 0.5 mL, 2.0 mmol) at ambient temperature for 4 hours. The title compound was collected by filtration and dried under vacuum. $^1$H NMR (300 MHz, MeOH-d$_4$) δ 7.52 (td, J=10.5, 8.3 Hz, 1H), 8.00-8.17 (m, 2H), 8.26 (ddd, J=8.1, 5.8, 0.7 Hz, 1H), 9.08-9.14 (m, 1H), 9.22-9.30 (m, 1H), 9.66 (d, J=2.0 Hz, 1H) ppm; MS (DCl/NH$_3$) m/z 260 (M+H)$^+$.

Example 34

5-(2,6-difluorophenyl)-3-(pyridin-3-yl)-1,2,4-oxadiazole

The title compound was prepared according to the procedure of Example 8 using N'-hydroxynicotinimidamide (Aldrich) and 2,6-difluorobenzoic acid (Aldrich). $^1$H NMR (300 MHz, CD$_3$OD) δ 7.29 (t, J=8.6 Hz, 2H), 7.65 (ddd, J=8.0, 4.9, 1.0 Hz, 1H), 7.77 (tt, J=8.6, 6.1 Hz, 1H), 8.57 (ddd, J=8.3, 1.9, 1.7 Hz, 1H), 8.75 (dd, J=4.7, 1.7 Hz, 1H), 9.30 (dd, J=2.2, 0.8 Hz, 1H) ppm; MS (DCl/NH$_3$) m/z 260 (M+H)$^+$.

Example 35

3-(3-(pyridin-3-yl)-1,2,4-oxadiazol-5-yl)benzenesulfonamide

The title compound was prepared according to the procedure of Example 8 using N'-hydroxynicotinimidamide (Aldrich) and 3-sulfamoylbenzoic acid (Oakwood). $^1$H NMR (300 MHz, CD$_3$OD) δ 7.65 (ddd, J=8.0, 4.9, 1.0 Hz, 1H), 7.83 (t, J=7.9 Hz, 1H), 8.21 (dt, J=7.9, 1.8, 1.0 Hz, 1H), 8.45 (dt, J=7.9, 1.4 Hz, 1H), 8.58 (dt, J=8.0, 1.9 Hz, 1H), 8.73-8.77 (m, 2H), 9.31 (dd, J=2.2, 1.0 Hz, 1H) ppm; MS (DCl/NH$_3$) m/z 303 (M+H)$^+$.

Example 36

5-(2,4-difluorophenyl)-3-(pyridin-3-yl)-1,2,4-oxadiazole

The title compound was prepared according to the procedure of Example 8 using N'-hydroxynicotinimidamide (Aldrich) and 2,4-difluorobenzoic acid (Aldrich). $^1$H NMR (300 MHz, CD$_3$OD) δ 7.23-7.36 (m, 2H), 7.64 (ddd, J=8.1, 5.0, 0.8 Hz, 1H), 8.35 (td, J=8.5, 6.4 Hz, 1H), 8.56 (dt, J=7.8, 1.9 Hz, 1H), 8.74 (dd, J=5.1, 1.7 Hz, 1H), 9.30 (dd, J=2.2, 0.8 Hz, 1H) ppm; MS (DCl/NH$_3$) m/z 260 (M+H)$^+$.

Example 37

5-(2,3,4-trifluorophenyl)-3-(pyridin-3-yl)-1,2,4-oxadiazole

The title compound was prepared according to the procedure of Example 8 using N'-hydroxynicotinimidamide (Aldrich) and 2,3,4-trifluorobenzoic acid (Aldrich). $^1$H NMR (300 MHz, CD$_3$OD) δ 7.37-7.48 (m, J=9.3, 9.3, 7.1, 2.4 Hz, 1H), 7.64 (ddd, J=7.9, 5.0, 1.0 Hz, 1H), 8.08-8.18 (m, 1H), 8.56 (dt, J=8.0, 1.9 Hz, 1H), 8.75 (dd, J=5.0, 1.8 Hz, 1H), 9.30 (dd, J=2.0, 0.8 Hz, 1H) ppm; MS (DCl/NH$_3$) m/z 278 (M+H)$^+$.

Example 38

5-(3,4,5-trifluorophenyl)-3-(pyridin-3-yl)-1,2,4-oxadiazole

The title compound was prepared according to the procedure of Example 8 using N'-hydroxynicotinimidamide (Aldrich) and 3,4,5-trifluorobenzoic acid (Aldrich). $^1$H NMR (300 MHz, CD$_3$OD) δ 7.64 (ddd, J=8.0, 4.9, 1.0 Hz, 1H), 8.01-8.13 (m, 2H), 8.56 (ddd, J=8.1, 1.8, 1.6 Hz, 1H), 8.75 (dd, J=4.8, 1.6 Hz, 1H), 9.29 (dd, J=2.0, 0.8 Hz, 1H) ppm; MS (DCl/NH$_3$) m/z 278 (M+H)$^+$.

Example 39

5-(4-chloro-3-fluorophenyl)-3-(pyridin-3-yl)-1,2,4-oxadiazole

The title compound was prepared according to the procedure of Example 8 using N'-hydroxynicotinimidamide (Aldrich) and 4-chloro-3-fluorobenzoic acid (Aldrich). $^1$H NMR (300 MHz, CD$_3$OD) δ 7.64 (ddd, J=7.9, 5.0, 1.0 Hz, 1H), 7.78 (dd, J=8.3, 7.5 Hz, 1H), 8.07 (ddd, J=8.3, 2.0, 0.8 Hz, 1H), 8.12 (dd, J=9.5, 2.0 Hz, 1H), 8.55 (dt, J=7.9, 2.0 Hz, 1H), 8.74 (dd, J=5.0, 1.8 Hz, 1H), 9.28-9.30 (m, 1H) ppm; MS (DCl/NH$_3$) m/z 276 (M+H)$^+$.

Example 40

5-(3-nitrophenyl)-3-(pyridin-3-yl)-1,2,4-oxadiazole

The title compound was prepared according to the procedure of Example 8 using N'-hydroxynicotinimidamide (Aldrich) and 3-nitrobenzoyl chloride (Aldrich). $^1$H NMR (300 MHz, CDCl$_3$) δ 7.44-7.55 (m, 1H), 7.82 (t, J=8.3 Hz, 1H), 8.43-8.60 (m, 3H), 8.80 (dd, J=4.7, 1.7 Hz, 1H), 9.07-9.13 (m, 1H), 9.42 (d, J=2.0 Hz, 1H) ppm; MS (DCI/NH$_3$) m/z 269 (M+H)$^+$.

Example 41

5-(3-(methylsulfonyl)phenyl)-3-(pyridin-3-yl)-1,2,4-oxadiazole

The title compound was prepared according to the procedure of Example 8 using N'-hydroxynicotinimidamide (Aldrich) and 3-(methylsulfonyl)benzoic acid (Aldrich). $^1$H NMR (300 MHz, CD$_3$OD) δ 3.24 (s, 3H), 7.65 (ddd, J=8.0, 4.9, 1.0 Hz, 1H), 7.89-7.96 (m, 1H), 8.28 (ddd, J=8.0, 1.9, 1.0 Hz, 1H), 8.55-8.61 (m, 2H), 8.75 (dd, J=5.1, 1.7 Hz, 1H), 8.78 (t, J=1.5 Hz, 1H), 9.32 (dd, J=2.2, 0.8 Hz, 1H) ppm; MS (DCI/NH$_3$) m/z 302 (M+H)$^+$.

Example 42

3-(2-chloropyridin-4-yl)-5-(pyridin-3-yl)-1,2,4-oxadiazole

Example 42A 2-chloro-N'-hydroxyisonicotinimidamide

A solution of 2-chloroisonicotinonitrile (Aldrich, 0.73 g, 5.27 mmol), and hydroxylamine (Aldrich, 50 wt %, 0.348 g, 5.27 mmol) in methanol (10 mL) was heated to reflux and stirred for 1 hour. The volatiles were removed under reduced pressure to give the title compound. $^1$H NMR (300 MHz, DMSO-d$_6$) δ 6.09 (s, 2H), 7.67 (dd, J=5.4, 1.4 Hz, 1H), 7.73 (d, J=2.0 Hz, 1H), 8.40 (d, J=5.2 Hz, 1H), 10.22 (s, 1H) ppm; MS (DCI/NH$_3$) m/z 172 (M+H)$^+$, 174 (M+H)$^+$.

Example 42B 3-(2-chloropyridin-4-yl)-5-(pyridin-3-yl)-1,2,4-oxadiazole

The title compound was prepared according to the procedure of Example 1 using the product of Example 42A and nicotinoyl chloride hydrochloride (Aldrich). $^1$H NMR (300 MHz, DMSO-d$_6$) δ 7.73 (ddd, J=8.0, 4.9, 1.0 Hz, 1H), 8.04-8.13 (m, 2H), 8.59 (dt, J=7.9, 2.0 Hz, 1H), 8.71 (d, J=5.2 Hz, 1H), 8.92 (dd, J=5.0, 1.8 Hz, 1H), 9.38 (dd, J=2.2, 1.0 Hz, 1H) ppm; MS (DCI/NH$_3$) m/z 259 (M+H)$^+$, 261 (M+H)$^+$.

Example 43

3-(3-(pyridin-3-yl)-1,2,4-oxadiazol-5-yl)benzamide

A solution of the product of Example 1 (248 mg, 1 mmol) in THF (10 ml) was stirred with potassium trimethylsilanolate (257 mg, 2.000 mmol) at 65° C. for 10 hours. It was then quenched with water (20 mL) and stirred at ambient temperature for 2 hours. The precipitate was filtered and dried under vacuum to give the title compound. $^1$H NMR (300 MHz, DMSO-d$_6$) δ 7.67 (ddd, J=7.9, 4.8, 0.8 Hz, 1H), 7.78 (t, J=7.7 Hz, 1H), 8.23 (dt, J=8.1, 1.4, 1.2 Hz, 1H), 8.30 [s (broad, 2H], 8.36 (dt, J=8.1, 1.3 Hz, 1H), 8.48 (dt, J=7.9, 2.0 Hz, 1H), 8.68-8.73 (m, 1H), 8.83 (dd, J=4.8, 1.6 Hz, 1H), 9.28 (dd, J=2.2, 1.0 Hz, 1H) ppm; MS (DCI/NH$_3$) m/z 267 (M+H)$^+$.

Example 44

4-(5-(pyridin-3-yl)-1,2,4-oxadiazol-3-yl)pyridin-2(1H)-one hydrochloric acid

A solution of the product of Example 42 (100 mg, 0.39 mmol) in concentrated hydrochloric acid (Aldrich, 36.5%, 3.0 mL) was heated in an Emry™ Creator microwave to 150° C. at 300 watts for 60 minutes. It was then concentrated. The residue was stirred in ethanol/ethyl acetate (v. 1/1, 5 mL) at ambient temperature for 1 hour. The title compound was collected by filtration and dried. $^1$H NMR (300 MHz, DMSO-d$_6$) δ 6.75 (dd, J=6.7, 1.6 Hz, 1H), 7.04 (d, J=1.6 Hz, 1H), 7.61 (d, J=5.9 Hz, 1H), 7.67-7.81 (m, 1H), 8.56 (dt, J=8.0, 1.9 Hz, 1H), 8.91 (dd, J=5.0, 1.8 Hz, 1H), 9.31-9.40 (m, 1H) ppm; MS (DCI/NH$_3$) m/z 241 (M+H)$^+$.

Example 45 tert-butyl 3-(3-(pyridin-3-yl)-1,2,4-oxadiazol-5-yl)benzoate

N'-Hydroxynicotinimidamide (274 mg, 2.00 mmol) was coupled with 3-(tert-butoxycarbonyl)benzoic acid (Aldrich) according to the procedure described in Example 8. $^1$H NMR (300 MHz, CD$_3$OD) δ 1.65 (s, 9H), 7.65 (ddd, J=7.9, 4.8, 0.8 Hz, 1H), 7.71-7.77 (m, 1H), 8.26 (ddd, J=7.7, 1.8, 1.6 Hz, 1H), 8.42-8.46 (m, 1H), 8.57 (dt, J=7.9, 2.0 Hz, 1H), 8.73-8.78 (m, 2H), 9.31 (dd, J=2.2, 1.0 Hz, 1H) ppm; MS (DCI/NH$_3$) m/z 324 (M+H)$^+$.

Example 46

2-amino-5-(3-(pyridin-3-yl)-1,2,4-oxadiazol-5-yl)phenol

A solution of the product of Example 25 (284 mg, 1 mmol) in tetrahydrofuran (10 mL) was stirred with Raney®-nickel (Aldrich, 100 mg) under hydrogen at ambient temperature for 2 hours. The catalyst was then removed by filtration and the organic solution concentrated to give the title compound. $^1$H NMR (300 MHz, DMSO-d$_6$) δ 5.67 (s, 2H), 6.74 (d, J=8.1 Hz, 1H), 7.41-7.50 (m, 2H), 7.62 (dd, J=8.3, 4.6 Hz, 1H), 8.39 (dt, J=8.2, 1.9, 1.7 Hz, 1H), 8.78 (dd, J=4.7, 1.7 Hz, 1H), 9.20 (d, J=1.7 Hz, 1H), 9.74 (s (broad), 1H) ppm; MS (DCI/NH$_3$) m/z 255 (M+H)$^+$.

Example 47

N,N-dimethyl-4-(5-(pyridin-3-yl)-1,2,4-oxadiazol-3-yl)pyridin-2-amine

A solution of the product of Example 42 (100 mg, 0.39 mmol) in dimethylformamide (2.0 mL) and ammonium hydroxide (0.5 mL) was sealed and heated to 150° C. in an Emry™ Creator microwave to 150° C. at 300 watts for 60 minutes. It was then concentrated. The residue was stirred in water (5 mL) at ambient temperature for 1 hour. The title compound was collected by filtration and dried. $^1$H NMR (300 MHz, DMSO-d$_6$) δ 3.12 (s, 6H), 7.18 (dd, J=5.2, 1.2 Hz, 1H), 7.21 (t, J=1.2 Hz, 1H), 7.66-7.78 (m, 1H), 8.31 (dd, J=4.8, 0.8 Hz, 1H), 8.57 (ddd, J=8.3, 2.0, 1.6 Hz, 1H), 8.91 (dd, J=5.0, 1.8 Hz, 1H), 9.35 (d, J=2.4 Hz, 1H) ppm; MS (DCI/NH$_3$) m/z 268 (M+H)$^+$.

Example 48

3-(3-(pyridin-3-yl)-1,2,4-oxadiazol-5-yl)benzoic acid

A solution of the product of Example 45 (180 mg, 0.56 mmol) in methylene chloride (5 mL) was stirred with trifluoroacetic acid (1 mL) at room temperature for 4 hours. It was then concentrated and the residue was stirred in water (15 mL) for 1 hour. The precipitate was collected by filtration and dried to give the title compound. $^1$H NMR (300 MHz, DMSO-$d_6$) δ 7.66 (ddd, J=7.9, 4.8, 0.8 Hz, 1H), 7.83 (t, J=7.5 Hz, 1H), 8.28 (ddd, J=8.0, 1.5, 1.2 Hz, 1H), 8.42-8.51 (m, 2H), 8.70 (t, J=1.6 Hz, 1H), 8.83 (dd, J=5.0, 1.8 Hz, 1H), 9.28 (dd, J=2.2, 1.0 Hz, 1H) ppm; MS (DCl/NH$_3$) m/z 268 (M+H)$^+$.

Example 49

5-(3-(1H-tetrazol-5-yl)phenyl)-3-(pyridin-3-yl)-1,2,4-oxadiazole hydrochloric acid A solution of the product of Example 1 (248 mg, 1.0 mmol) in toluene (anhydrous, 10 mL) was stirred with azidotributylstannane (Aldrich, 498 mg, 1.50 mmol) at 110° C. for 15 hours. It was then cooled to ambient temperature and stirred with 5 mL of sodium hydroxide (1 N) at ambient temperature for 1 hour. The organic solution was separated, the aqueous mixture was acidified to pH=2-3 with hydrochloric acid (10 wt. %) and stirred for 2 hours. The precipitate was collected by filtration and dried to give the title product. $^1$H NMR (300 MHz, DMSO-$d_6$) δ 7.70-7.76 (m, 1H), 7.86-7.98 (m, 1H), 8.23 (ddd, J=7.8, 1.7, 1.0 Hz, 0.2H), 8.38-8.46 (m, 1.6H), 8.49-8.53 (m, 0.2H), 8.56 (ddd, J=8.1, 1.9 Hz, 0.8H), 8.65 (ddd, J=1.7, 0.7 Hz, 0.2H), 8.83-8.92 (m, 2H), 9.30 (dd, J=2.2, 0.8 Hz, 0.2H), 9.33 (dd, J=2.2, 0.8 Hz, 0.8H) ppm; MS (DCl/NH$_3$) m/z 292 (M+H)$^+$.

Example 50

N,N-diethyl-3-(3-(pyridin-3-yl)-1,2,4-oxadiazol-5-yl)benzenesulfonamide

Example 50A

3-(N,N-diethylsulfamoyl)benzoic acid

Diethylamine (Aldrich, 2.5 mL, 24 mmol) was added to a solution of 3-(chlorosulfonyl)benzoic acid (Aldrich, 2.0 g, 9.1 mmol) in anhydrous dichloromethane (20 mL) at 0° C. The mixture was then stirred at 0° C. for 2 hours. The volatiles were removed under reduced pressure. The residue was treated with aqueous potassium hydrogensulfate (1 M, 10 mL) and then extracted with ethyl acetate (3×50 mL). The combined extracts were dried over magnesium sulfate filtered and then concentrated to give the title compound. $^1$H NMR (300 MHz, CD$_3$OD) δ 1.13 (t, J=7.1 Hz, 6H), 3.22-3.30 (m, 4H), 7.69 (t, J=7.8 Hz, 1H), 8.03 (ddd, J=7.9, 1.9, 1.4 Hz, 1H), 8.25 (dt, J=7.8, 1.4 Hz, 1H), 8.40 (t, J=1.7 Hz, 1H) ppm; MS (DCl/NH$_3$) m/z 275 (M+NH$_4$)$^+$.

Example 50B

N,N-Diethyl-3-(3-(pyridin-3-yl)-1,2,4-oxadiazol-5-yl)benzenesulfonamide

The title compound was prepared according to the procedure of Example 8 using N'-hydroxynicotinimidamide (Aldrich) and the product of Example 50A. $^1$H NMR (300 MHz, CD$_3$OD) δ 1.17 (t, J=7.1 Hz, 6H), 3.29-3.37 (m, 4H), 7.65 (ddd, J=8.1, 5.0, 0.8 Hz, 1H), 7.86 (t, J=7.6 Hz, 1H), 8.14 (ddd, J=7.9, 1.8, 1.2 Hz, 1H), 8.48 (dt, J=7.9, 1.5 Hz, 1H), 8.58 (dt, J=8.1, 1.9 Hz, 1H), 8.62 (t, J=1.5 Hz, 1H), 8.75 (dd, J=5.1, 1.7 Hz, 1H), 9.31 (dd, J=2.2, 0.8 Hz, 1H) ppm; MS (DCl/NH$_3$) m/z 359 (M+H)$^+$.

Example 51

2-fluoro-5-(3-(pyridin-3-yl)-1,2,4-oxadiazol-5-yl)benzonitrile

The title compound was prepared according to the procedure of Example 8 using N'-hydroxynicotinimidamide (Aldrich) and 3-cyano-4-fluorobenzoic acid (Aldrich). $^1$H NMR (300 MHz, CD$_3$OD) δ ppm 7.62-7.71 (m, 2H), 8.54-8.63 (m, 2H), 8.69 (dd, J=5.9, 2.2 Hz, 1H), 8.75 (dd, J=4.9, 1.5 Hz, 1H), 9.30 (dd, J=2.0, 1.0 Hz, 1H); MS (DCl/NH$_3$) m/z 267 (M+H)$^+$.

Example 52

3-(3-(1H-tetrazol-5-yl)phenyl)-5-(pyridin-3-yl)-1,2,4-oxadiazole hydrochloric acid The title compound was prepared according to the procedure of Example 49 using the product of Example 3 and azidotributylstannane (Aldrich). $^1$H NMR (300 MHz, DMSO-$d_6$) δ 7.74 (dd, J=7.3, 5.4 Hz, 1H), 7.87 (t, J=7.7 Hz, 1H), 8.25-8.43 (m, 2H), 8.53-8.70 (m, 1H), 8.75-8.85 (m, 1H), 8.88-9.00 (m, 1H), 9.32-9.58 (m, 1H) ppm; MS (DCl/NH$_3$) m/z 292 (M+H)$^+$.

Example 53

3-(6-chloropyridin-3-yl)-5-(pyridin-3-yl)-1,2,4-oxadiazole

Example 53A

6-Chloro-N'-hydroxynicotinimidamide

A solution of 2-chloroisonicotinonitrile (Aldrich, 5.0 g, 36.1 mmol) and hydroxylamine (Aldrich, 50% wt, 2.38 g, 36.0 mmol) in methanol (100 ml) was heated to reflux and stirred for 1 hour. The volatiles were removed under reduced pressure to give the title compound. $^1$H NMR (300 MHz, DMSO-$d_6$) δ 6.03 (s, 2H), 7.54 (d, J=8.7 Hz, 1H), 8.07 (dd, J=8.3, 2.4 Hz, 1H), 8.67 (d, J=2.8 Hz, 1H), 9.94 (s, 1H) ppm; MS (DCl/NH$_3$) m/z 172 (M+H)$^+$, 189 (M+H)$^+$.

Example 53B

3-(6-chloropyridin-3-yl)-5-(pyridin-3-yl)-1,2,4-oxadiaole

The title compound was prepared according to the procedure of Example 1 using the product of Example 53A and nicotinoyl chloride hydrochloride (Aldrich). $^1$H NMR (300 MHz, MeOH-$d_4$) δ 7.62-7.75 (m, 2H), 8.53 (dd, J=8.1, 2.4 Hz, 1H), 8.60-8.67 (m, 1H), 8.85 (dd, J=5.1, 1.7 Hz, 1H), 9.14

(dd, J=2.4, 0.7 Hz, 1H), 9.39 (dd, J=2.2, 0.8 Hz, 1H) ppm; MS (DCl/NH$_3$) m/z 259 (M+H)$^+$, 261 (M+H)$^+$.

Example 54

5-(6-chloropyridin-3-yl)-3-(pyridin-3-yl)-1,2,4-oxadiaole

The title compound was prepared according to the procedure of Example 1 using N'-hydroxynicotinimidamide (Tyger) and 6-chloronicotinoyl chloride (Aldrich). $^1$H NMR (300 MHz, CDCl$_3$) δ 7.48 (dd, J=7.6, 5.3 Hz, 1H), 7.57 (d, J=8.5 Hz, 1H), 8.40-8.48 (m, 2H), 8.80 (dd, J=4.7, 1.7 Hz, 1H), 9.24 (d, J=2.4 Hz, 1H), 9.40 (d, J=2.4 Hz, 1H) ppm; MS (DCl/NH$_3$) m/z 259 (M+H)$^+$, 261 (M+H)$^+$.

Example 55

5-(5-(pyridin-3-yl)-1,2,4-oxadiazol-3-yl)pyridin-2(1H)-one

A solution of the product of Example 53B (0.10 g, 0.39 mmol) in concentrated hydrochloric acid (1.0 mL) was heated in a microwave to 150° C. at 300 watts for 60 minutes. It was then concentrated under reduced pressure and the residue was purified by chromatography [silica gel, CHCl$_3$/methanol (with 10% v/v ammonium hydroxide), v. 90/10] to provide the title compound. $^1$H NMR (300 MHz, DMSO-d$_6$) δ 6.28-6.73 (m, 1H), 7.64-7.74 (m, 1H), 7.98 (dd, J=9.5, 2.7 Hz, 1H), 8.14 (d, J=2.4 Hz, 1H), 8.49-8.56 (m, 1H), 8.89 (dd, J=4.7, 1.7 Hz, 1H), 9.32 (d, J=1.4 Hz, 1H), 12.17 (s, 1H) ppm; MS (DCl/NH$_3$) m/z 241 (M+H)$^+$, 258 (M+NH$_4$)$^+$.

Example 56

5-(3-(pyridin-3-yl)-1,2,4-oxadiazol-5-yl)pyridin-2(1H)-one

The title compound was prepared according to the procedure of Example 55 using the product of Example 54. $^1$H NMR (300 MHz, DMSO-d$_6$) δ 6.55 (d, J=9.2 Hz, 1H), 7.63 (dd, J=7.6, 5.3 Hz, 1H), 8.05 (dd, J=9.8, 2.7 Hz, 1H), 8.31-8.47 (m, 2H), 8.80 (d, J=3.4 Hz, 1H), 9.22 (s, 1H), 12.41 (s, 1H) ppm; MS (DCl/NH$_3$) m/z 241 (M+H)$^+$, 258 (M+NH$_4$)$^+$.

Example 57

N-methyl-3-(3-(pyridin-3-yl)-1,2,4-oxadiazol-5-yl)benzenesulfonamide

Example 57A 3-(N-methylsulfamoyl)benzoic acid

The title compound was prepared according to the procedure of Example 50A using 3-(chlorosulfonyl)benzoic acid (Aldrich) and methylamine (Aldrich). $^1$H NMR (300 MHz, CD$_3$OD) δ 2.54 (s, 3H), 7.70 (t, J=7.8 Hz, 1H), 8.02-8.07 (m, 1H), 8.23-8.28 (m, 1H), 8.45 (t, J=1.9 Hz, 1H) ppm; MS (DCl/NH$_3$) m/z 233 (M+NH$_4$)$^+$.

Example 57B

N-methyl-3-(3-(pyridin-3-yl)-1,2,4-oxadiazol-5-yl)benzenesulfonamide

The title compound was prepared according to the procedure of Example 8 using N'-hydroxynicotinimidamide (Aldrich) and the product of Example 57A. $^1$H NMR (300 MHz, CD$_3$OD) δ 2.60 (s, 3H), 7.65 (ddd, J=8.1, 5.0, 0.8 Hz, 1H), 7.87 (t, J=8.1 Hz, 1H), 8.15 (ddd, J=8.0, 1.9, 1.0 Hz, 1H), 8.48 (ddd, J=7.8, 1.7, 1.0 Hz, 1H), 8.58 (dt, J=8.1, 1.9 Hz, 1H), 8.67 (t, J=1.5 Hz, 1H), 8.75 (dd, J=4.7, 1.7 Hz, 1H), 9.31 (dd, J=2.2, 0.8 Hz, 1H) ppm; MS (DCl/NH$_3$) m/z 317 (M+H)$^+$.

Example 58

3-(3-(pyridin-3-yl)-1,2,4-oxadiazol-5-yl)aniline dihydrochloride

Example 58A 3-(3-(pyridin-3-yl)-1,2,4-oxadiazol-5-yl)aniline

The title compound was prepared according to the procedure of Example 46 using the product of Example 40. $^1$H NMR (300 MHz, DMSO-d$_6$) δ ppm 5.60 (s, 2H), 6.84-6.93 (m, 1H), 7.24-7.33 (m, 2H), 7.41 (d, J=1.7 Hz, 1H), 7.60-7.67 (m, 1H), 8.38-8.45 (m, 1H), 8.81 (dd, J=5.1, 1.7 Hz, 1H), 9.23 (d, J=2.4 Hz, 1) ppm; MS (DCl/NH$_3$) m/z 239 (M+H)$^+$, 256 (M+NH$_4$)$^+$.

Example 58B 3-(3-(pyridin-3-yl)-1,2,4-oxadiazol-5-yl)aniline dihydrochloride A solution of the product of Example 58A (60 mg, 0.25 mmol) in ethyl acetate (2 mL) was stirred with hydrochloric acid (Aldrich, 4 M in dioxane, 0.14 mL, 0.55 mmol) at ambient temperature for 4 hours. The title compound was collected by filtration and dried under vacuum. $^1$H NMR (300 MHz, DMSO-d$_6$) δ 7.44 (d, J=7.9 Hz, 1H), 7.62 (t, J=7.9 Hz, 1H), 7.80 (dd, J=7.9, 5.2 Hz, 1H), 7.85-7.96 (m, 2H), 8.60 (d, J=7.9 Hz, 1H), 8.90 (d, J=4.8 Hz, 1H), 9.31 (s, 1H) ppm; MS (DCl/NH$_3$) m/z 239 (M+H)$^+$, 256 (M+NH$_4$)$^+$.

Example 59

3-(3-(pyridin-3-yl)-1,2,4-oxadiazol-5-yl)phenyl)methanamine bis(hydrochloric acid A solution of the product of Example 62 (120 mg, 0.34 mmol) in ethyl acetate (5 mL) was stirred with hydrochloric acid (Aldrich, 4 M in dioxane, 0.5 mL, 2.0 mmol) at ambient temperature for 4 hours. The precipitate was collected by filtration and dried under vacuum to give the title compound. $^1$H NMR (300 MHz, DMSO-d$_6$) δ 4.21 (q, J=5.9 Hz, 2H), 7.65-7.79 (m, 2H), 7.86 (dt, J=8.0, 1.3 Hz, 1H), 8.24 (dt, J=7.7, 1.4 Hz, 1H), 8.35-8.45 (m, 3H), 8.48 (dt, J=8.1, 1.9 Hz, 1H), 8.85 (dd, J=4.9, 1.2 Hz, 1H), 9.28 (d, J=1.4 Hz, 1H) ppm; MS (DCl/NH$_3$) m/z 253 (M+H)$^+$.

Example 60

5-(2-chloropyridin-4-yl)-3-(pyridin-3-yl)-1,2,4-oxadiazole

The title compound was prepared according to the procedure of Example 1 using N'-hydroxynicotinimidamide (Aldrich) and 2-chloroisonicotinoyl chloride (Maybridge). $^1$H NMR (300 MHz, DMSO-d$_6$) δ 7.68 (ddd, J=7.9, 4.8, 0.8 Hz, 1H), 8.16 (dd, J=5.1, 1.4 Hz, 1H), 8.23 (dd, J=1.5, 0.8 Hz, 1H), 8.42-8.54 (m, 1H), 8.77 (dd, J=5.1, 0.7 Hz, 1H), 8.84

(dd, J=4.7, 1.7 Hz, 1H), 9.28 (dd, J=2.2, 0.8 Hz, 1H) ppm; MS (DCl/NH$_3$) m/z 259 (M+H)$^+$, 261 (M+H)$^+$.

Example 61

4-(3-(pyridin-3-yl)-1,2,4-oxadiazol-5-yl)pyridin-2(1H)-one hydrochloric acid

The title compound was prepared according to the procedure of Example 44 using the product of Example 60. $^1$H NMR (300 MHz, DMSO-d$_6$) δ 6.81 (dd, J=6.6, 1.9 Hz, 1H), 7.09-7.14 (m, 1H), 7.67-7.76 (m, 2H), 8.51 (dt, J=8.0, 1.9, 1.7 Hz, 1H), 8.86 (dd, J=4.9, 1.5 Hz, 1H), 9.28 (d, J=1.4 Hz, 1H) ppm; MS (DCl/NH$_3$) m/z 241 (M+H)$^+$.

Example 62 tert-butyl 3-(3-(pyridin-3-yl)-12,4-oxadiazol-5-yl)benzylcarbamate

The title compound was prepared according to the procedure of Example 8 using N'-hydroxynicotinimidamide (Aldrich) and 3-((tert-butoxycarbonylamino)methyl)benzoic acid (Fluka). $^1$H NMR (300 MHz, DMSO-d$_6$) δ 1.42 (s, 9H), 4.27 (d, J=6.1 Hz, 2H), 7.51-7.72 (m, 4H), 8.01-8.17 (m, 2H), 8.45 (dt, J=8.1, 1.9 Hz, 1H), 8.82 (dd, J=5.1, 1.7 Hz, 1H), 9.26 (dd, J=2.2, 0.8 Hz, 1H) ppm; MS (DCl/NH$_3$) m/z 353 (M+H)$^+$.

Example 63

5-(3-bromophenyl)-3-(pyridin-3-yl)-1,2,4-oxadiazole

The title compound was prepared according to the procedure of Example 1 using N'-hydroxynicotinimidamide (Aldrich) and 3-bromobenzoyl chloride (Aldrich). $^1$H NMR (300 MHz, DMSO-d$_6$) δ 7.60-7.71 (m, 2H), 7.98 (ddd, J=8.1, 2.0, 1.0 Hz, 1H), 8.22 (ddd, J=7.4, 1.6, 1.3 Hz, 1H), 8.35 (t, J=1.8 Hz, 1H), 8.46 (dt, J=7.9, 2.0 Hz, 1H), 8.83 (dd, J=4.8, 1.6 Hz, 1H), 9.27 (dd, J=2.4, 0.8 Hz, 1H) ppm; MS (DCl/NH$_3$) m/z 302 (M+H)$^+$, 304 (M+H)$^+$.

Example 64

1-(3-(3-(pyridin-3-yl)-1,2,4-oxadiaol-5-yl)phenyl)pyrrolidin-2-one

A solution of the product of Example 63 (200 mg, 0.66 mmol) and pyrrolidin-2-one (Aldrich, 85 mg, 0.99 mmol) in toluene (anhydrous 10 mL) was degassed and purged with nitrogen three times, cesium carbonate (Aldrich, 324 mg, 0.993 mmol) and tris(dibenzylideneacetone)dipalladium(0) (Aldrich, 12.1 mg, 0.013 mmol), 4,5-bis(diphenylphosphino)-9,9-dimethylxanthene (Aldrich, 23.0 mg, 0.040 mmol, xantphos) were added, degassed and purged with nitrogen three times. The mixture was then heated to 100° C. and stirred under nitrogen for 15 hours. It was then cooled to ambient temperature and diluted with ethyl acetate (50 mL), washed with brine (2×5 mL), concentrated, purified with chromatography (v. ethyl acetate/hexane=1/1, R$_f$=0.1) to give the title compound. $^1$H NMR (300 MHz, DMSO-d$_6$) δ 2.04-2.19 (m, 2H), 2.57 (t, J=7.9 Hz, 2H), 3.95 (t, J=6.9 Hz, 2H), 7.60-7.75 (m, 2H), 7.84-8.10 (m, 2H), 8.46 (dt, J=7.9, 2.0 Hz, 1H), 8.64 (t, J=2.0Hz, 1H), 8.82 (dd, J=5.0, 1.8 Hz, 1H), 9.26 (dd, J=2.2, 0.8 Hz, 1H) ppm; MS (DCl/NH$_3$) m/z 307 (M+H)$^+$.

Example 65 tert-butyl 3-(3-(pyridin-3-yl)-1,2,4-oxadiazol-5-yl)phenylcarbamate

The title compound was prepared according to the procedure of Example 8 using N'-hydroxynicotinimidamide (Aldrich) and 3-(tert-butoxycarbonylamino)benzoic acid (Aldrich). $^1$H NMR (300 MHz, CDCl$_3$) δ 1.56 (s, 9H), 6.71 (s, 1H), 7.39-7.58 (m, 2H), 7.68 (d, J=7.9 Hz, 1H), 7.89 (d, J=9.1 Hz, 1H), 8.24 (s, 1H), 8.45 (d, J=7.9 Hz, 1H), 8.77 (d, J=4.8 Hz, 1H), 9.40 (s, 1H) ppm; MS (DCl/NH$_3$) m/z 339 (M+H)$^+$, 356 (M+NH$_4$)$^+$.

Example 66

N,N-dimethyl-1-(3-(3-(pyridin-3-yl)-1,2,4-oxadiazol-5-yl)phenyl)methanamine, bishydrochloric acid salt The free base of the title compound was prepared according to the procedure of Example 8 using N'-hydroxynicotinimidamide (Aldrich) and 3-((dimethylamino)methyl)benzoic acid (Aldrich). A solution of this free base in ethyl acetate (5 mL) was treated with hydrochloric acid (Aldrich, 0.5 mL, 4M in dioxane) at ambient temperature for 2 hours. The title compound was collected by filtration and dried under vacuum. $^1$H NMR (300 MHz, CD$_3$OD) δ 2.93 (s, 6H), 4.51 (s, 2H), 7.82 (t, J=7.8 Hz, 1H), 7.90 (dt, J=7.8, 1.5 Hz, 1H), 8.23 (dd, J=8.0, 5.9 Hz, 1H), 8.42 (dt, J=7.7, 1.4 Hz, 1H), 8.49 (t, J=1.5 Hz, 1H), 9.04 (d, J=5.1 Hz, 1H), 9.21 (dt, J=8.1, 1.7 Hz, 1H), 9.56 (s, 1H) ppm; MS (DCl/NH$_3$) m/z 281 (M+H)$^+$.

Example 67

5-(3-(piperazin-1-yl)phenyl)-3-(pyridin-3-yl)-1,2,4-oxadiazole bis(hydrochloric acid)

Example 67A tert-butyl 4-(3-(3-(pyridin-3-yl)-1,2,4-oxadiazol-5-yl)phenyl)piperazine-1-carboxylate A solution of the product of Example 63 (200 mg, 0.66 mmol) and tert-butyl piperazine-1-carboxylate (Aldrich, 123 mg, 0.66 mmol) in toluene (anhydrous, 10 mL) was degassed and purged with nitrogen three times, sodium t-butoxide (Aldrich, 64 mg, 0.66 mmol) and tris(dibenzylideneacetone)dipalladium(0) (Aldrich, 12.1 mg, 0.013 mmol), 4,5-bis(diphenylphosphino)-9,9-dimethylxanthene (Aldrich, 23.0 mg, 0.040 mmol, xantphos) were added, degassed and purged with nitrogen three times. The mixture was then heated to 100° C. and stirred under nitrogen for 15 hours. It was then cooled to ambient temperature and diluted with ethyl acetate (50 mL), washed with brine (2×5 mL), concentrated, purified with chromatography (v. ethyl acetate/hexane=1/1, R$_f$=0.6) to give the title compound. $^1$H NMR (300 MHz, MeOH-d$_4$) δ 1.49 (s, 9H), 3.25-3.30 (m, 4H), 3.56-3.71 (m, 4H), 7.31 (ddd, J=8.4, 2.6, 0.8 Hz, 1H), 7.49 (t, J=8.0 Hz, 1H), 7.64 (ddd, J=8.0, 4.9, 0.7 Hz, 1H), 7.70 (dt, J=8.0, 1.1 Hz, 1H), 7.79 (dd, J=2.4, 1.7 Hz, 1H), 8.56 (dt, J=7.9, 2.0 Hz, 1H), 8.74 (dd, J=4.9, 1.5 Hz, 1H), 9.29 (dd, J=2.2, 0.8 Hz, 1H) ppm; MS (DCl/NH$_3$) m/z 408 (M+H)$^+$.

Example 67B 5-(3-(piperazin-1-yl)phenyl)-3-(pyridin-3-yl)-1,2,4-oxadiazole bis(hydrochloric acid)

The title compound was prepared according to the procedure of Example 59 using the product of Example 67A. $^1$H NMR (300 MHz, MeOH-$d_4$) δ 3.40-3.48 (m, 4H), 3.54-3.62 (m, 4H), 7.42 (ddd, J=8.3, 2.8, 0.8 Hz, 1H), 7.58 (t, J=8.1 Hz, 1H), 7.78-7.94 (m, 2H), 8.24-8.39 (m, 1H), 9.08 (d, J=5.9 Hz, 1H), 9.32 (dt, J=8.3, 1.8 Hz, 1H), 9.59 (d, J=1.6 Hz, 1H) ppm; MS (DCl/NH$_3$) m/z 308 (M+H)$^+$.

Example 68

1-(3-(3-(pyridin-3-yl)-1,2,4-oxadiazol-5-yl)phenyl)ethanone

The title compound was prepared according to the procedure of Example 8 using N'-hydroxynicotinimidamide (Aldrich) and 3-acetylbenzoic acid (Aldrich). $^1$H NMR (300 MHz, CD$_3$OD) δ 2.72 (s, 3H), 7.66 (ddd, J=8.0, 4.9, 1.0 Hz, 1H), 7.80 (t, J=8.1 Hz, 1H), 8.31 (ddd, J=8.1, 1.4, 1.2 Hz, 1H), 8.47 (ddd, J=8.1, 1.4, 1.2 Hz, 1H), 8.59 (ddd, J=8.1, 2.0, 1.8 Hz, 1H), 8.75 (dd, J=5.2, 1.6 Hz, 1H), 8.81 (t, J=1.4 Hz, 1H), 9.32 (dd, J=2.4, 0.8 Hz, 1H) ppm; MS (DCl/NH$_3$) m/z 266 (M+H)$^+$.

Example 69

3-(6-chloropyridin-3-yl)-5-(2,3-difluorophenyl)-1,2,4-oxadiazole

The title compound was prepared according to the procedure of Example 1 using the product of Example 53A and 2,3-difluorobenzoyl chloride (Aldrich). $^1$H NMR (300 MHz, DMSO-$d_6$) δ 7.41-7.59 (m, 1H), 7.76-7.93 (m, 2H), 8.05 (dd, J=7.8, 6.1 Hz, 1H), 8.48 (dd, J=8.3, 2.5 Hz, 1H), 9.08 (d, J=2.4 Hz, 1H) ppm; MS (DCl/NH$_3$) m/z 294 (M+H)$^+$, 296 (M+H)$^+$.

Example 70

3-(6-chloropyridin-3-yl)-5-(3,4-difluorophenyl)-1,2,4-oxadiazole

The title compound was prepared according to the procedure of Example 1 using the product of Example 53A and 3,4-difluorobenzoyl chloride (Aldrich). $^1$H NMR (300 MHz, DMSO-$d_6$) δ ppm 7.70-7.83 (m, 2H), 8.03-8.15 (m, 1H), 8.22-8.36 (m, 1H), 8.48 (dd, J=8.1, 2.4 Hz, 1H), 9.08 (d, J=2.4 Hz, 1H) ppm; MS (DCl/NH$_3$) m/z 294 (M+H)$^+$, 296 (M+H)$^+$.

Example 71

R)-3-(pyridin-3-yl)-5-(3-(pyrrolidin-2-yl)phenyl)-1,2,4-oxadiazole bis(hydrochloric acid

Example 71A (R)-tert-butyl 2-(3-(3-(pyridin-3-yl)-1,2,4-oxadiazol-5-yl)phenyl)pyrrolidine-1-carboxylate Under nitrogen, to a solution of tert-butyl pyrrolidine-1-carboxylate (Aldrich, 0.52 g, 3.00 mmol) and (−)-sparteine (Aldrich, 0.69 g, 3.0 mmol) in t-butyl methyl ether (Aldrich, anhydrous, 10 mL) was added sec-butyllithium (Aldrich, 1.4 M in cyclohexane, 2.2 mL, 3.1 mmol) at −78° C. After the completion of the addition, it was stirred at −78° C. for 3 hours. Zinc chloride (Aldrich, 1 M in diethyl ether, 2.0 mL, 2.0 mmol) was then added slowly and the resultant solution was stirred at −78° C. for additional 30 minutes and then warmed up to ambient temperature, stirred for another 30 minutes at room temperature before the addition of a solution of the product of the Example 63 (0.30 g, 1.0 mmol) in tetrahydrofuran (anhydrous, 5.0 mL) and bis(tri-t-butylphosphine)palladium(0) (Strem, 10.2 mg, 0.02 mmol). The mixture was stirred at ambient temperature for 15 hours and quenched with ammonium hydroxide (5 mL). The mixture was extracted with ethyl acetate (3×20 mL). The combined extracts were concentrated and purified by chromatography (v. hexanes/ethyl acetate=1/1, R$_f$=0.5) to give the title compound. $^1$H NMR (300 MHz, MeOH-$d_4$) δ 1.19 (s (broad), 6H), 1.48 (s (broad), 3H), 1.83-2.00 (m, 2H), 2.37-2.55 (m, J=8.1, 8.1 Hz, 1H), 3.57-3.72 (m, 2H), 4.90-5.14 (m, 1H), 7.47-7.73 (m, 3H), 8.00-8.25 (m, 2H), 8.56 (dt, J=8.3, 1.8 Hz, 1H), 8.74 (dd, J=5.1, 1.7 Hz, 1H), 9.29 (dd, J=2.0, 0.7 Hz, 1H) ppm; MS (DCl/NH$_3$) m/z 393 (M+H)$^+$.

Example 71B

R)-3-(Pyridin-3-yl)-5-(3-(pyrrolidin-2-yl)phenyl)-1,2,4-oxadiazole bis(hydrochloric acid The title compound was prepared according to the procedure of Example 59 using the product of Example 71A. $^1$H NMR (300 MHz, DMSO-$d_6$) δ 1.98-2.27 (m, 3H), 2.39-2.50 (m, 1H), 3.22-3.51 (m, 2H), 4.55-4.81 (m, 1H), 7.71-7.82 (m, 2H), 7.96 (d, J=7.9 Hz, 1H), 8.26 (dt, J=7.8, 1.2 Hz, 1H), 8.40 (s, 1H), 8.58 (dt, J=8.1, 1.9 Hz, 1H), 8.89 (dd, J=5.2, 1.6 Hz, 1H), 9.21-9.53 (m, J=1.6 Hz, 2H) ppm; MS (DCl/NH$_3$) m/z 293 (M+H)$^+$.

Example 72

5-(3-(1H-pyrazol-3-yl)(phenyl)-3-(pyridin-3-yl)-1,2,4-oxadiazole

The title compound was prepared according to the procedure of Example 8 using N'-hydroxynicotinimidamide (Aldrich) and 3-(1H-pyrazol-3-yl)benzoic acid (Maybridge). $^1$H NMR (300 MHz, DMSO-$d_6$) δ 6.91 (d, J=2.4 Hz, 1H), 7.62-7.69 (m, 1H), 7.72 (t, J=7.8 Hz, 1H), 7.79-7.92 (m, 1H), 7.82-7.88 (m, 1H), 8.10-8.20 (m, 3H), 8.49 (dt, J=8.2, 1.9, 1.7 Hz, 1H), 8.64 (s, 1H), 8.83 (dd, J=4.7, 1.7 Hz, 1H), 9.29 (dd, J=2.2, 0.8 Hz, 1H) ppm; MS (DCl/NH$_3$) m/z 290 (M+H)$^+$.

Example 73

1-(3-(3-(pyridin-3-yl)-1,2,4-oxadiazol-5-yl)phenyl)ethanol

A solution of the product of Example 68 (265 mg, 1.0 mmol) in ethanol (5 mL) was stirred with sodium borohydride (Aldrich, 83 mg, 2.2 mmol) at room temperature for 16 hours. The inorganic solid was filtered off with a syringe filter and the liquid mixture was purified by preparative HPLC (Gilson, column, Xbridge® 5 μm, 30×100 mm. eluting solvent, acetonitrile/water (pH=10, NH$_4$HCO$_3$—NH$_3$.H$^2$O buffer), v. 5/95 to 95/5 over 35 minutes, flow rate, 40 mL/minute, uv, 234 nm). Fractions of the desired product were collected and concentrated to give the desired product. $^1$H NMR (300 MHz, CD$_3$OD) δ 1.51 (d, J=6.7 Hz, 3H), 4.97 (q, J=6.6 Hz, 1H), 7.57-7.73 (m, 3H), 8.13 (dt, J=7.6, 1.5 Hz, 1H), 8.28 (t, J=1.8

Hz, 1H), 8.57 (dt, J=7.9, 1.8 Hz, 1H), 8.74 (dd, J=5.0, 1.8 Hz, 1H), 9.30 (dd, J=2.2, 1.0 Hz, 1H) ppm; MS (DCl/NH$_3$) m/z 268 (M+H)$^+$.

Example 74

3-(3-(6-chloropyridin-3-yl)-1,2,4-oxadiazol-5-yl) benzonitrile

The title compound was prepared according to the procedure of Example 1 using the product of Example 53A and 3-cyanobenzoyl chloride (Aldrich). $^1$H NMR (300 MHz, CDCl$_3$) δ 7.52 (d, J=7.8 Hz, 1H), 7.75 (t, J=8.0 Hz, 1H), 7.93 (d, J=7.8 Hz, 1H), 8.30-8.50 (m, 2H), 8.54 (s, 1H), 9.19 (d, J=2.4 Hz, 1H) ppm; MS (DCl/NH$_3$) m/z 283 (M+H)$^+$, 300 (M+NH4)$^+$.

Example 75

3-(4-fluorophenyl)-5-(pyridin-3-yl)-1,2,4-oxadiazole

4-Fluoro-N'-hydroxybenzimidamide (0.154 g, 1 mmol) was dissolved in pyridine (10 mL) and nicotinoyl chloride (Aldrich, 0.141 g, 1 mmol) was added. The reaction mixture was heated to reflux for 3 hours and then cooled to room temperature. The cooled reaction mixture was quenched with water (25 mL) and filtered. The solid was further purified with flash column chromatography (5% methanol/dichloromethane) to give the titled product. $^1$H NMR (300 MHz, DMSO-d$_6$) δ 7.47 (t, J=6.8 Hz, 2H), 7.74-7.70 (m, 1H), 8.20-8.15 (m, 2H), 8.58-8.54 (m, 1H), 8.91-8.89 (dd, J=1.7, 1.7 Hz, 1H), 9.35 (d, J=1.4 Hz, 1H) ppm; MS (DCl/NH$_3$) m/z 242 (M+H)$^+$.

Example 76

3-(5-(6-chloropyridin-3-yl)-1,2,4-oxadiazol-3-yl) benzonitrile

The title compound was prepared according to the procedure of Example 4B using 3-cyano-N'-hydroxybenzimidamide (Example 4A) and 6-chloronicotinoyl chloride (Aldrich). $^1$H NMR (300 MHz, DMSO-d$_6$) δ 7.87 (m, 2H), 8.17 (m, 1H), 8.4 (m, 1H), 8.43 (d, J=1.7 Hz, 1H), 8.6 (m, 1H), 9.25 (d, J=1.7 Hz, 1H) ppm; MS (DCl/NH$_3$) m/z 283 (M+H)$^+$.

Example 77

3-(5-(2-fluoropyridin-3-yl)-1,2,4-oxadiazol-3-yl) benzonitrile

The title compound was prepared according to the procedure of Example 4B using 3-cyano-N'-hydroxybenzimidamide (Example 4A) and 2-fluoronicotinoyl chloride (Aldrich). $^1$H NMR (300 MHz, DMSO-d$_6$) δ 7.87 (m, 1H), 7.95 (m, 1H), 8.17 (m, 1H), 8.17 (m, 1H), 8.43 (m, 1H), 8.6 (m, 1H), 8.8 (m, 1H) ppm; MS (DCl/NH$_3$) m/z 267 (M+H)$^+$.

Example 78

3-fluoro-5-(5-(pyridin-3-yl)-1,2,4-oxadiazol-3-yl) benzonitrile

The title compound was prepared according to the procedure of Example 4B using 3-cyano-5-fluoro-N'-hydroxybenzimidamide (Prepared from 5-fluoroisophthalonitrile using the procedure described in Example 4A) and nicotinoyl chloride (Aldrich). $^1$H NMR (300 MHz, DMSO-d$_6$) δ 7.77 (m, 1H), 8.2 (m, 2H), 8.4 (m, 1H), 8.6 (m, 1H), 8.9 (m, 1H), 9.4 (m, 1H) ppm; MS (DCl/NH$_3$) m/z 267 (M+H)$^+$.

In addition to the specific compounds, one of ordinary skill in the art would readily recognize that a variety of pharmaceutically acceptable salts, esters, and amides of a parent compound also could be incorporated into a composition, method, or article of manufacture of the present invention.

Suitable pharmaceutically acceptable basic addition salts include, but are not limited to cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

Other possible compounds include pharmaceutically acceptable amides and esters. "Pharmaceutically acceptable ester" refers to those esters, which retain, upon hydrolysis of the ester bond, the biological effectiveness and properties of the carboxylic acid and are not biologically or otherwise undesirable. For a description of pharmaceutically acceptable esters as prodrugs, see Bundgaard, E., ed., (1985) Design of Prodrugs, Elsevier Science Publishers, Amsterdam, which is hereby incorporated by reference. These esters are typically formed from the corresponding carboxylic acid and an alcohol. Generally, ester formation can be accomplished via conventional synthetic techniques. (See, e.g., March Advanced Organic Chemistry, 3rd Ed., John Wiley & Sons, New York p. 1157 (1985) and references cited therein, and Mark et al. Encyclopedia of Chemical Technology, John Wiley & Sons, New York (1980), both of which are hereby incorporated by reference. The alcohol component of the ester will generally comprise (i) a C2-C12 aliphatic alcohol that can or can not contain one or more double bonds and can or can not contain branched carbons or (ii) a C7-C12 aromatic or heteroaromatic alcohols. This invention also contemplates the use of those compositions, which are both esters as described herein, and at the same time are the pharmaceutically acceptable salts thereof.

"Pharmaceutically acceptable amide" refers to those amides, which retain, upon hydrolysis of the amide bond, the biological effectiveness and properties of the carboxylic acid and are not biologically or otherwise undesirable. For a description of pharmaceutically acceptable amides as prodrugs, see Bundgaard, H., Ed., (1985) Design of Prodrugs, Elsevier Science Publishers, Amsterdam. These amides are typically formed from the corresponding carboxylic acid and an amine. Generally, amide formation can be accomplished via conventional synthetic techniques. (See, e.g., March Advanced Organic Chemistry, 3rd Ed., John Wiley & Sons, New York, p. 1152 (1985) and Mark et al. Encyclopedia of Chemical Technology, John Wiley & Sons, New York (1980), both of which are hereby incorporated by reference. This invention also contemplates the use of those compositions, which are amides, as described herein, and at the same time are the pharmaceutically acceptable salts thereof.

It also will be readily apparent to one with skill in the art that the compounds can be generated in vivo by administration of a drug precursor which, following administration, releases the drug in vivo via a chemical or physiological process (e.g., a parent compound on being brought to the physiological pH or through enzyme action is converted to the desired drug form).

Administration

As noted above, it has been discovered that pain can be treated by concurrently administering to a patient (e.g., a mammal, such as a human) in need thereof, an α4β2 PAM and an α4β2 receptor ligand. Such combination may be especially useful in expanding the dosage range for obtaining therapeutically beneficial effects.

As used in this application, the term "concurrent administration" refers to administering the α4β2 receptor ligand to a patient, who has been prescribed (or has consumed) at least one an α4β2 PAM, at an appropriate time so that the patient's symptoms may subside. This may mean simultaneous administration of an α4β2 PAM and an α4β2 receptor ligand, or administration of the medications at different, but appropriate times. Establishing such a proper dosing schedule will be readily apparent to one skilled in the art, such as a physician treating various pain states.

The dosage range at which the α4β2 PAM and an α4β2 receptor ligand will be administered concurrently can vary widely. The specific dosage will be chosen by the patient's physician taking into account the particular compounds chosen, the severity of the patient's illness, any other medical conditions or diseases the patient is suffering from, other drugs the patient is taking and their potential to cause an interaction or adverse event, the patient's previous response to medication, and other factors. Suitable dosage ranges for the α4β2 PAM are from about 0.0001 mg/kg to 100 mg/kg of body weight. Suitable dosage ranges for the α4β2 receptor ligand are from about 0.0001 mg/kg to 100 mg/kg of body weight.

The α4β2 PAM and an α4β2 receptor ligand should be administered concurrently in amounts that are effective to treat the patient's pain, cognitive disorder, or related condition. In more general terms, one would create a combination of the present invention by choosing a dosage of an α4β2 PAM and an α4β2 receptor ligand according to the spirit of the guidelines presented above.

The invention also is carried out by administering an α4β2 PAM together with an α4β2 receptor ligand in any manner which provides effective levels of the compounds in the body at the same time. Typically, the combination will be administered orally.

However, the invention is not limited to oral administration. The invention should be construed to cover any route of administration that is appropriate for the medications involved and for the patient. For example, transdermal administration may be very desirable for patients who are forgetful or petulant about taking oral medicine. Injections may be appropriate for patients refusing their medication. One of the drugs may be administered by one route, such as oral, and the others may be administered by the transdermal, percutaneous, intravenous, intramuscular, intranasal, or intrarectal route, in particular circumstances. The route of administration may be varied in any way, limited by the physical properties of the drugs and the convenience of the patient and the caregiver.

Based on the diversity of the mechanisms underlying chronic pain (e.g. nociceptive or neuropathic, degrees of pain intensity, various etiologies etc), currently available pain medications are not efficacious in all patients or in all pain conditions. Analgesics can be broadly categorized as non-opioid analgesics (acetaminophen and non-steroidal anti-inflammatory drugs (NSAIDs)), opioid analgesics (morphine) and adjuvant analgesics or co-analgesics (antiepileptic drugs and antidepressants). In a simplified classification, non-opioid analgesics are mostly used to relieve mild to moderate nociceptive pain, adjuvant analgesics (gabapentin, pregabalin) are used to relieve neuropathic pain, and opioid analgesics are used to treat severe pain of all origins, depending on the dose prescribed.

Nicotinic acetylcholine receptor ligands act at multiple locations throughout the pain pathway to relieve pain. Nicotinic acetylcholine receptor ligands are found on primary sensory neurons (periphery) where nociceptive information is initiated, in the cell body regions of these neurons (i.e. the dorsal root ganglion or DRG), the dorsal spinal cord where the first pain synapse is located, in the brainstem cell body regions that control descending innervation, as well as in the higher brain regions that integrate and perceive sensory information such as the thalamus and the cortex. The current theory supported by evidence from multiple sources (reviewed in Decker et al., Curr Topics Med Chem, 4: 369, 2004) is that anti-nociceptive effects of nAChR ligands are mediated by activation of brain stem nuclei with descending inhibitory inputs to the spinal cord. Additional pathways may also mediate analgesic effects of nAChR agonists in persistent or neuropathic pain.

Another aspect of the invention is the potential to enhance efficacy of other medications used for treating pain when combined with an α4β2 PAM. As noted above, examples of currently used drugs include opioids, gabapentin, pregabalin, duloxetine and others. Novel mechanisms such as cannabinoids, vanilloid receptor antagonists, calcium channel blockers and sodium channel blockers are also being developed for the treatment of pain. For many of these mechanisms, it is emerging that a component of efficacy may be driven by activation of descending inhibitory inputs. For example, opioid analgesics can block pain transmission, in part by increasing descending inhibitory pathways to modulate pain transmission at the spinal level (Pasternack, G. W., Clin Neuropaharmcol. 16: 1, 1993; Lauretti, G. T., Expert Reviews in Neurotherapeutics, 6: 613-622. 2006). Since these drugs exert their effect via activating descending inhibitory inputs, and these pathways can be shared or commonly activated by α4β2 nAChR ligands, it is anticipated that co-administration of α4β2 selective PAMs can lead to enhanced efficacy of other analgesic agents by amplifying the descending inhibitory control of spinal cord activation. Thus, combination with α4β2 PAMs enables the opportunity to create analgesic medications with either a broader or superior spectrum of efficacy that would improve the treatment of chronic pain.

Other nAChR-mediated diseases or disorders also can benefit from such concurrent administration. The combination of α4β2 nAChR ligands and α4β2 selective PAMs can be used for treatment of diseases or disorders related to the cholinergic system of the central nervous system, the peripheral nervous system, diseases or disorders related to smooth muscle contraction, endocrine diseases or disorders, diseases or disorders related to neuro-degeneration, diseases or disorders related to inflammation, and withdrawal symptoms caused by the termination of abuse of chemical substances, in for example nicotine, as well as pain. In a particular embodiment, the combination is useful for conditions and disorders related to attention deficit disorder, attention deficit hyperactivity disorder (ADHD), Alzheimer's disease (AD), schizophrenia, mild cognitive impairment, age-associated memory impairment (AAMI), senile dementia, AIDS dementia, Pick's Disease, dementia associated with Lewy bodies, dementia associated with Down's syndrome, schizophrenia, smoking cessation, substance abuse, amyotrophic lateral sclerosis, Huntington's disease, diminished CNS function associated with traumatic brain injury, acute pain, post-surgical pain, chronic pain, inflammatory pain, neuropathic pain, infertility, lack of circulation, need for new blood vessel growth associated with wound healing, more particularly circulation around a vascular occlusion, need for new blood vessel growth associated with vascularization of skin grafts, ischemia, inflammation, sepsis, wound healing, and other complications associated with diabetes, among other systemic and neuroimmunomodulatory activities. The method is useful for conditions and disorders related to conditions and disorders characterized by neuropsychological and cognitive dysfunction, for example in Alzheimer's disease, bipolar disorder, schizophrenia, schizoaffective disorder, and other related disorders characterized by neuropsychological and cognitive dysfunction, in particular.

For example, one embodiment relates to a method of use for treating or preventing a condition or disorder characterized by attention or cognitive dysfunction, such as Alzhimer's disease and ADHD, among other condition and disorders. The method comprises the step of administering a therapeutically effective amount of a nicotinic acetylcholine receptor subtype α4β2 positive allosteric modulator to a subject in need thereof in combination with a drug that improves cholinergic function. Examples of such drugs are nicotinic acetylcholine receptor ligands and acetylcholinesterase inhibitors.

Another method of use relates to treating or preventing a condition or disorder characterized by neuropsychological dysfunction, for example scizhophrenia, wherein the method comprises the step of administering a therapeutically effective amount of a nicotinic acetylcholine receptor subtype α4β2 positive allosteric modulator to a subject in need thereof in combination with an antipsychotic agent.

BIOLOGICAL ACTIVITY

Example 1

α4β2 Positive Allosteric Modulator Enhances the Effects of Nicotinic Agonists

Calcium Flux Assays Using Cells Expressing nAChR Subtypes

Experimental Procedure: Human embryonic kidney (HEK) 293 cells stably expressing human α4β2 or α3β4 combinations are grown to confluency in 162 cm$^2$ tissue culture flasks in DMEM media supplemented with 10% FBS and 25 μg/ml zeocin and 200 μg/ml hygromycin B. IMR-32 neuroblastoma cells (ATCC) are grown to confluency in 162 cm$^2$ tissue culture flasks in minimum essential media supplemented with 10% FBS and 1 mM sodium pyruvate, 1% nonessential amino acids and 1% antibiotic-antimycotic. The cells are then dissociated using cell dissociation buffer and 100-150 μl per well of 3.5×10$^5$ cells/ml cell suspension (~50,000-100,000 cells/well) was plated into 96-well black plates (poly-D-lysine precoated) with clear bottom and maintained for 24-48 hrs in a tissue culture incubator at 37° C. under an atmosphere of 5% $CO_2$: 95% air. Other clonal cell lines or primary cell cultures that express endogenous α4* nicotinic receptors may also be used in this assay. Calcium flux was measured using calcium-3 assay kit (Molecular Devices, Sunnyvale, Calif.) or fluo-4 (Invitrogen). A stock solution of the dye was prepared by dissolving each vial supplied by the vendor in Hank's balanced salt solution buffer (HBSS) or 150 mM NMDG, 20 mM $CaCl_2$ containing 10 mM HEPES, The stock solution was diluted 1:20 using the same buffer before use. The growth media was removed from the cells. The cells were loaded with 100 μl of the dye per well and incubated at room temperature for up to one hour for HEK 293 clonal stable cell lines or 30 min-45 min at 37° C. for IMR-32 cells Fluorescence measurements were read simultaneously from all the wells by a Fluorometic Imaging Plate Reader (FLIPR) at an excitation wavelength of 480 nm and an emission wavelength of 520 nm. Baseline fluorescence was measured for the first 6 seconds at which 3× concentrations of modulator/test compounds were added to the cell plate at 50 μl and incubated for five minutes. The fluorescence intensity was captured every second for the first 1 minute followed by every 5 seconds for an additional 4 minutes. This procedure was followed by 50 μl of 4× concentration of agonist and readings were taken for a period of 3-5 minutes as described above. Data was normalized to maximal responses and plotted as a function of concentration. The concentration dependence of changes fluorescence responses was fitted by nonlinear regression analysis (GraphPad Prism, San Diego, Calif.) to obtain $EC_{50}$ values.

Figure 1B:
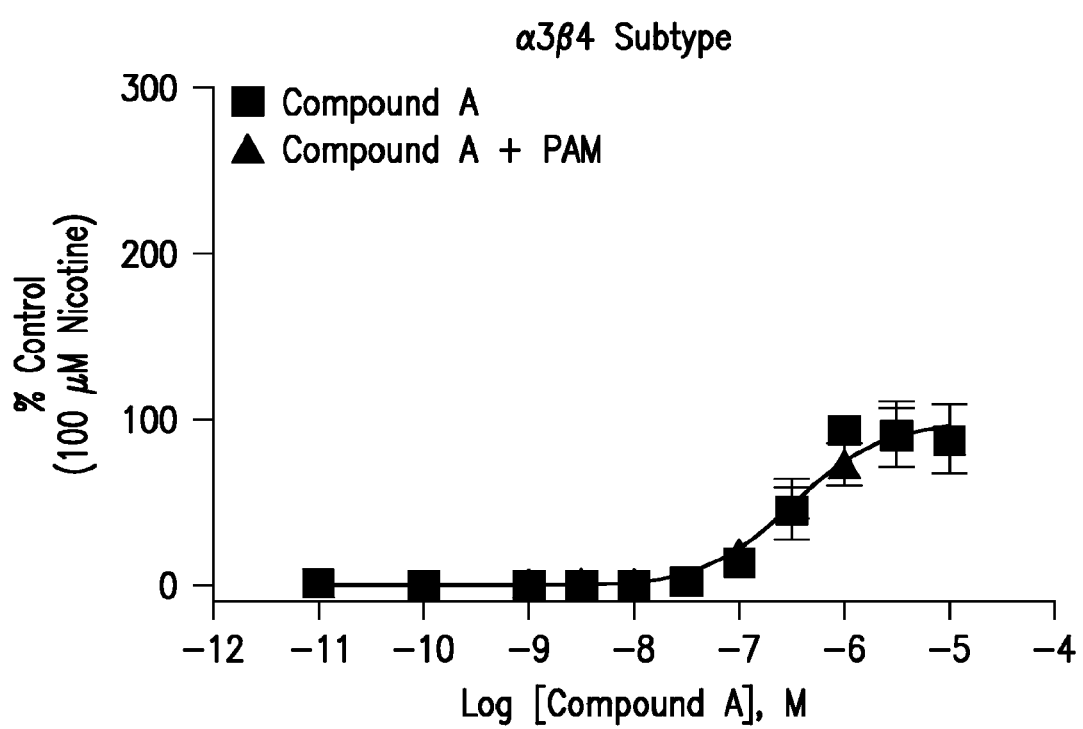
Figure 2A:
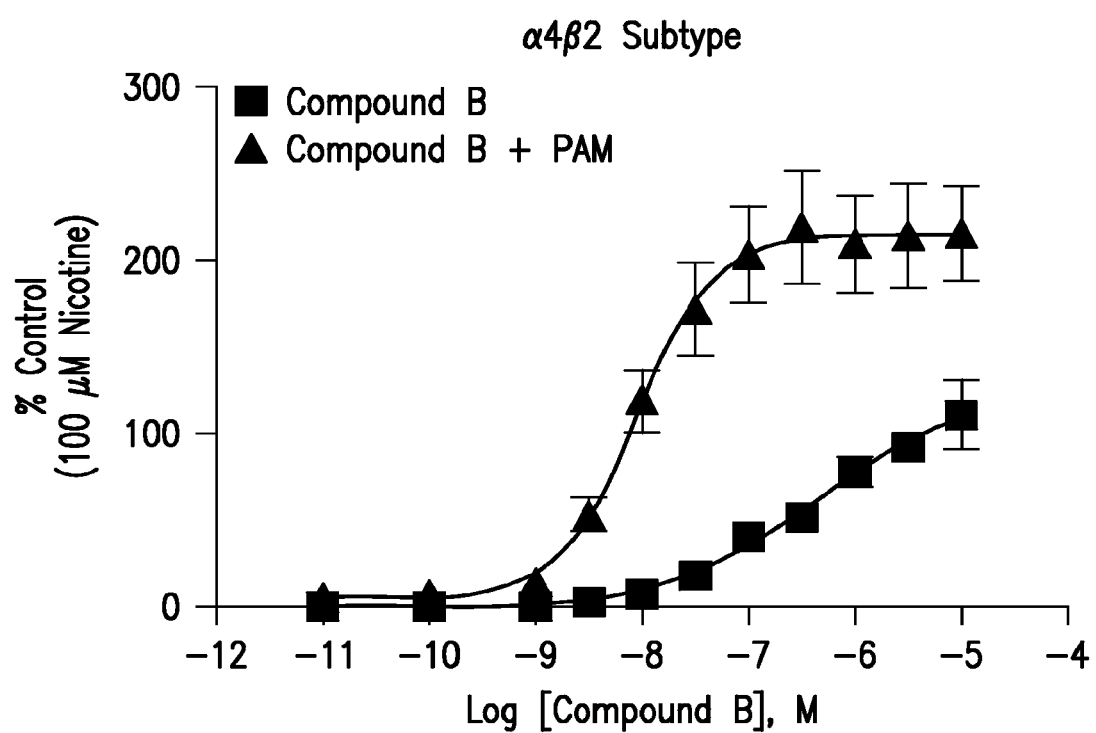
FIGS. 2A and 2B depict responses of another representative nicotinic acetylcholine receptor ligand, (3R)-1-pyridin-3-ylpyrrolidin-3-amine (Compound B), in the absence and presence of an α4β2 positive allosteric modulator, 3-(3-(pyridin-3-yl)-1,2,4-oxadiazol-5-yl)benzonitrile (PAM, Compound 1), at human α4β2 or α3β4 nicotinic receptor subtypes expressed in HEK-293 cells. Again, the data demonstrate a leftward shift in potency ($EC_{50}$ value) of the nAChR agonist at α4β2, but not α3β4 nAChRs.
Figure 2B:
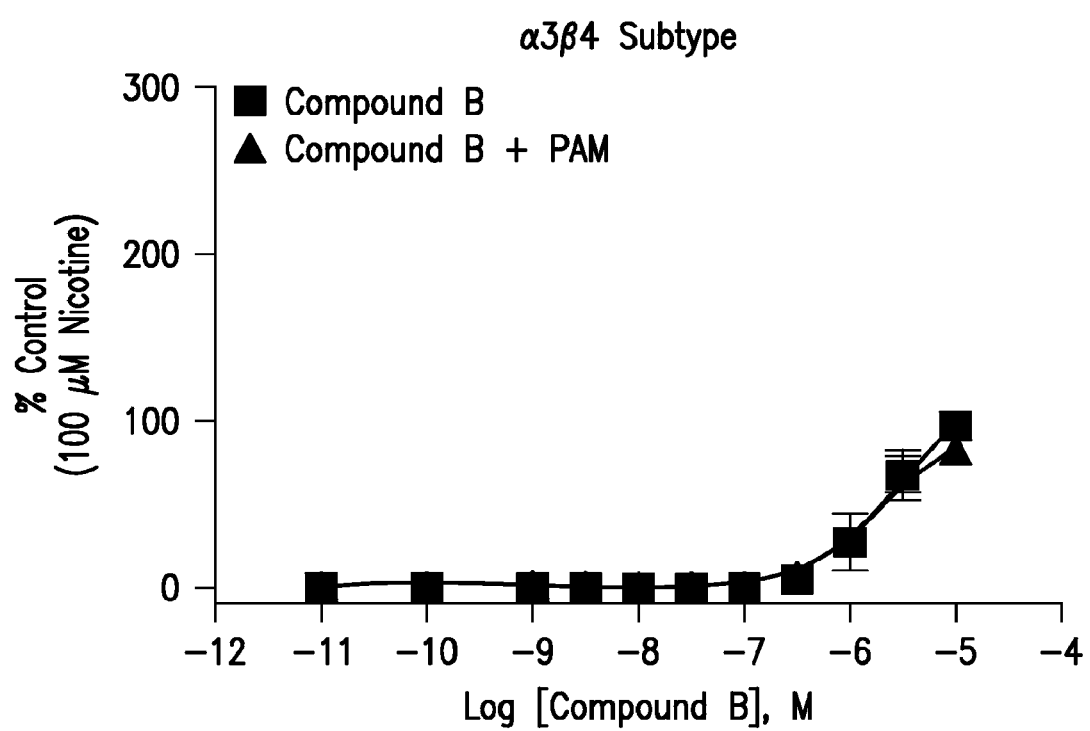

The positive allosteric modulator effects on α4β2 nAChRs exemplified by 3-(3-pyridin-3-yl-1,2,4-oxadiazol-5-yl)benzonitrile (Compound 1) and 3,5-di(pyridin-3-yl)-1,2,4-oxadiazole (Compound 2) can be identified by measuring their potentiating effect to fluorescence changes in intracellular calcium using a fluorimetric plate reader. The potentiating effect of an α4β2 modulator on α4β2 receptor can also be illustrated by concentration responses to α4β2 agonists, for example 5-[(2R)-azetidin-2-ylmethoxy]-2-chloropyridine (Compound A) and (3R)-1-pyridin-3-ylpyrrolidin-3-amine (Compound B), in presence of a fixed concentration of PAM. As shown in FIGS. 1A and 2A, in the presence of an α4β2 PAM (for example, 3-(3-(pyridin-3-yl)-1,2,4-oxadiazol-5-yl) benzonitrile (Compound 1) at 10 μM), the concentration-responses to α4β2 agonists, for example 5-[(2R)-azetidin-2-ylmethoxy]-2-chloropyridine (Compound A) and (3R)-1-pyridin-3-ylpyrrolidin-3-amine (Compound B), are shifted typically by 1-2 log units (10-100-fold) to the left resulting in more potent $EC_{50}$ values to agonists. In addition to compound A and B, other known nicotinic agonists can be left-shifted in presence of α4β2 PAM such as 3-(3-(pyridin-3-yl)-1,2,4-oxadiazol-5-yl)benzonitrile (Compound 1, FIG. 2C). When these experiments are done with cells expressing other nAChR subunits such as α3β4 (see FIGS. 1B and 2B), the PAM is unable to affect the concentration responses to the agonists. This shows that PAMs can selective enhance potency of the compound selectively at α4β2, but not other (e.g. α3β4) subtypes. This could lead to preferential effects of the agonist at the desired subtype, viz., α4β2, without effects at other nicotinic receptor subtypes and thus enhancing in vivo selectivity of the agonist.

Table 1 lists the results for the compounds of the present invention. The activity (allosteric effects—potentiation of fluorescence responses) ranges are defined as follows; "a" denotes as activity range from 200-400%, "b" denotes an activity range from 150-200%, "c" denotes an activity range from 120-150% and "d" denotes an activity range 90-120%.

TABLE 1

Examples of Selected α4β2 positive allosteric modulators

| Example No. | Structure | Activity |
|---|---|---|
| 1 | [pyridin-3-yl-1,2,4-oxadiazol-benzonitrile structure] | a |

TABLE 1-continued

Examples of Selected α4β2 positive allosteric modulators

| Example No. | Structure | Activity |
|---|---|---|
| 2 | 3-pyridyl-1,2,4-oxadiazole-3-pyridyl | a |
| 3 | (3-cyanophenyl)-1,2,4-oxadiazole-3-pyridyl | a |
| 4 | (3-cyanophenyl)-1,2,4-oxadiazole-(6-fluoropyridin-3-yl) | b |
| 5 | 3-pyridyl-1,2,4-oxadiazole-(5-bromopyridin-3-yl) | c |
| 7 | (6-methylpyridin-3-yl)-1,2,4-oxadiazole-(3-cyanophenyl) | b |
| 9 | 3-pyridyl-1,2,4-oxadiazole-(5-hydroxypyridin-3-yl) | d |
| 10 | 3-pyridyl-1,2,4-oxadiazole-(3,4-difluorophenyl) | a |
| 11 | 3-pyridyl-1,2,4-oxadiazole-(2,3-difluorophenyl) | a |
| 19 | 3-pyridyl-1,2,4-oxadiazole-(4-cyanophenyl) | b |
| 35 | 3-pyridyl-1,2,4-oxadiazole-(3-sulfamoylphenyl) | a |
| 40 | 3-pyridyl-1,2,4-oxadiazole-(3-nitrophenyl) | a |
| 41 | 3-pyridyl-1,2,4-oxadiazole-(3-methylsulfonylphenyl) | c |
| 42 | (2-chloropyridin-4-yl)-1,2,4-oxadiazole-3-pyridyl | c |
| 52 | 3-pyridyl-1,2,4-oxadiazole-(3-tetrazolylphenyl) | d |
| 55 | (6-oxo-1,6-dihydropyridin-3-yl)-1,2,4-oxadiazole-3-pyridyl | c |
| 68 | 3-pyridyl-1,2,4-oxadiazole-(3-acetylphenyl) | b |
| 76 | (3-cyanophenyl)-1,2,4-oxadiazole-(6-chloropyridin-3-yl) | b |

Figure 3A:
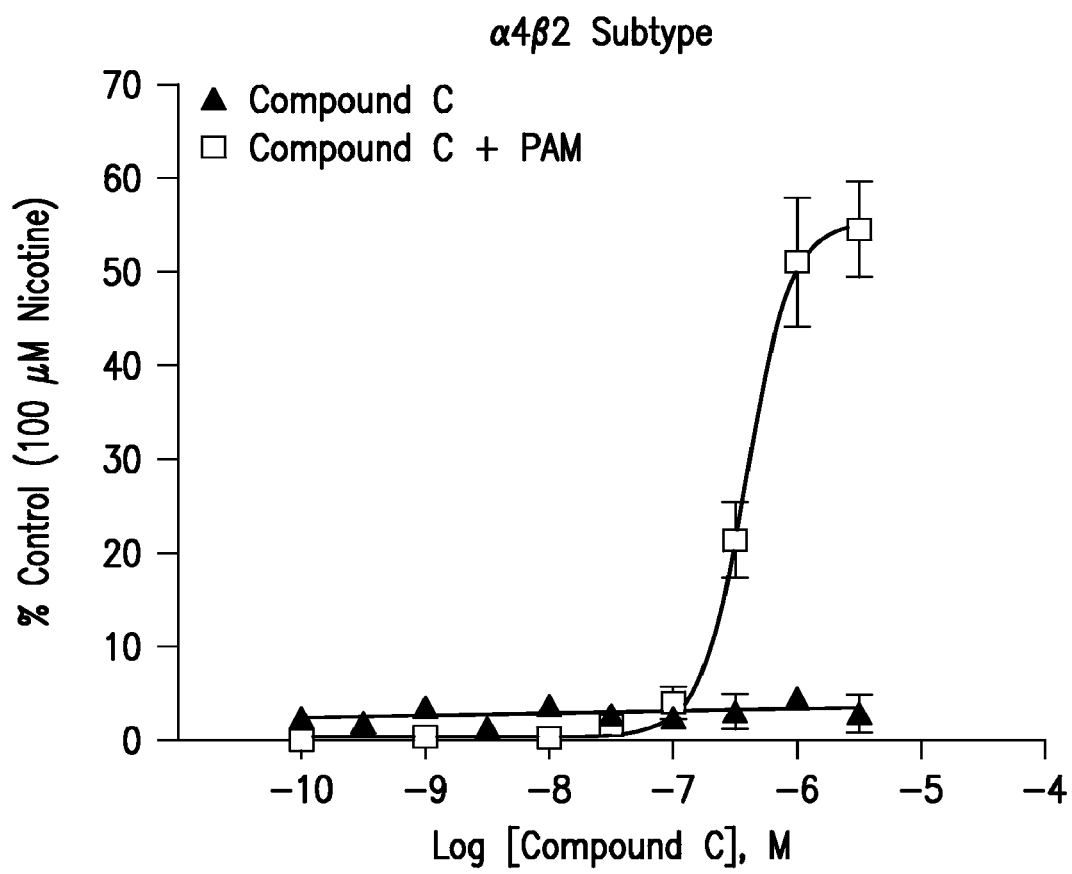
FIGS. 3A and 3B graphically represents the effect of α4β2 positive allosteric modulator in enhancing the effect of a nAChR partial agonist, such as 2-methyl-3-(2-(S)-pyrrolidinylmethoxy)pyridine (Compound C, also known as ABT-089; Reuter, L. E., Anderson, D. J., Briggs, C. A., Donnelly-Roberts et al., CNS Drug Rev., 10 (2), 167-182, 2004). Compound C alone does not evoke a calcium response, but when co-applied with the PAM, 3-(3-(pyridin-3-yl)-1,2,4-oxadiazol-5-yl)benzonitrile (Compound 1), evoked robust responses at α4β2 nAChRs (FIG. 3A), but not at α3β4 nAChRs (FIG. 3B). Compound C is a representative of other nicotinic partial agonists.
Figure 3B:
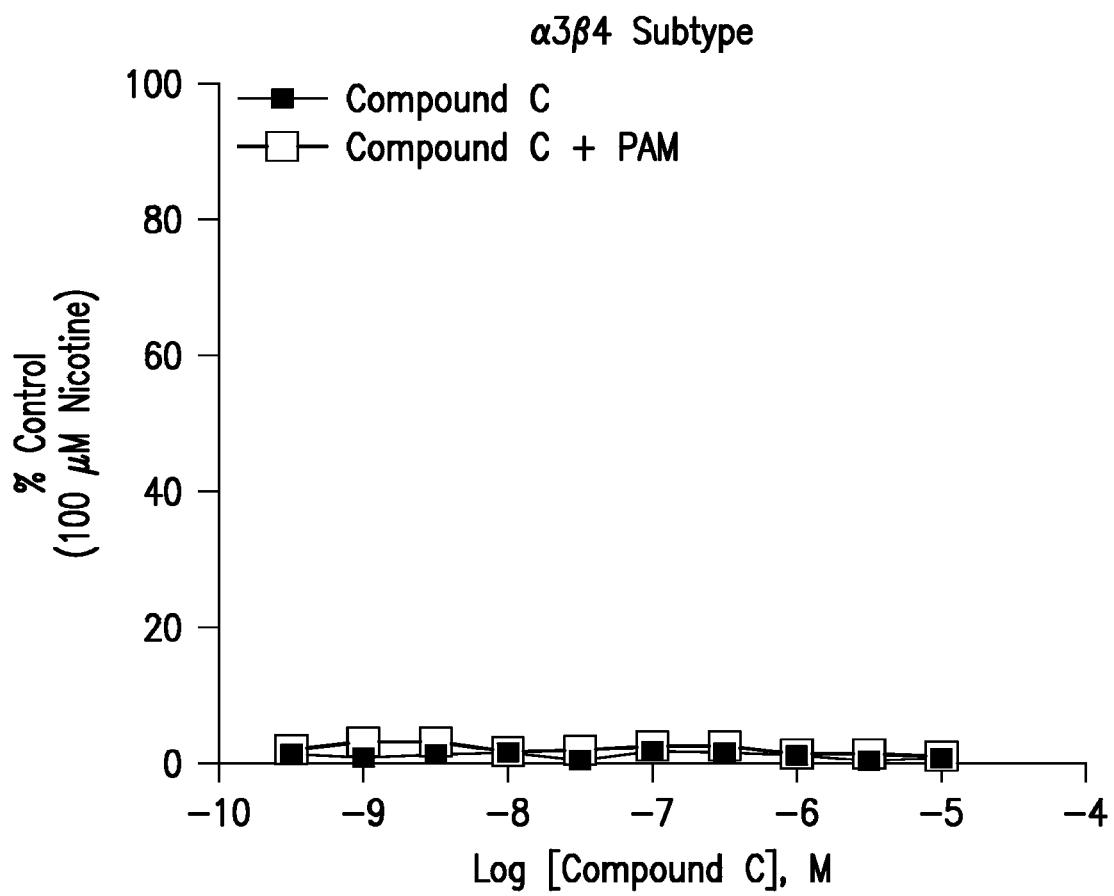
Figure 4A:
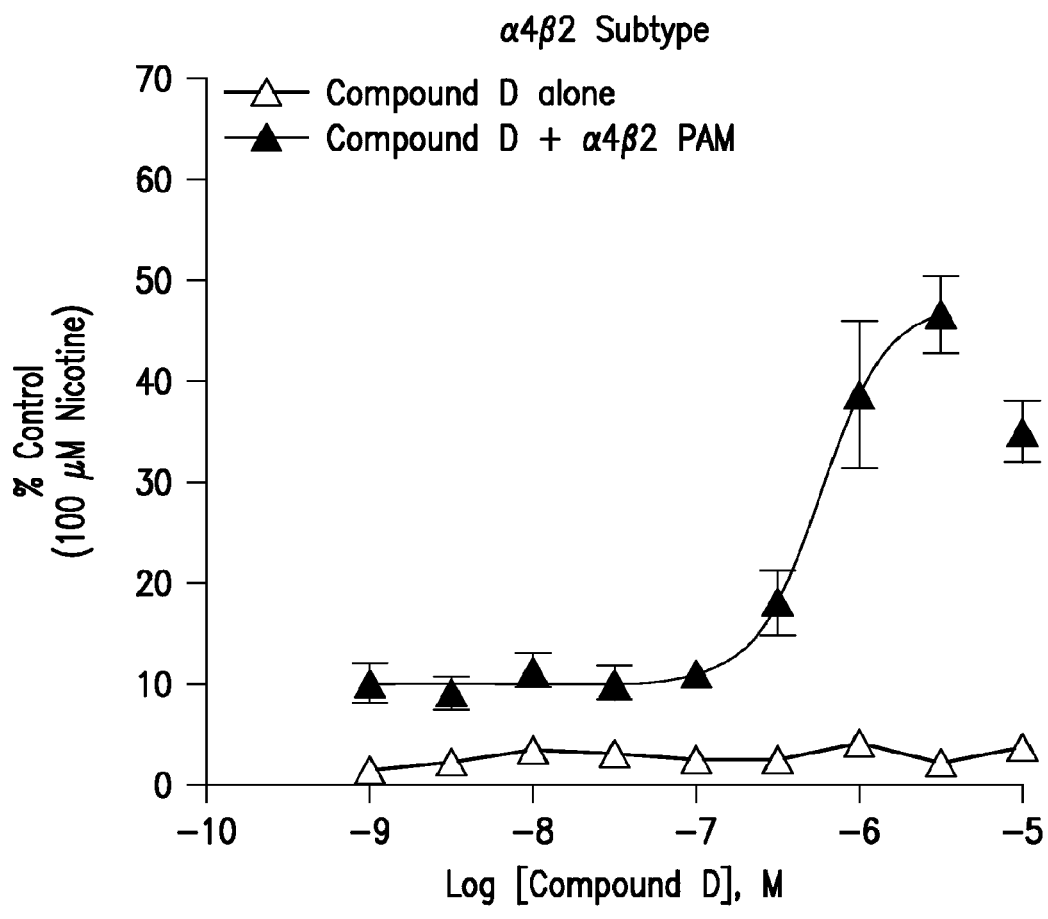
FIGS. 4A and 4B graphically represents the effect of an α4β2 positive allosteric modulator in enhancing the effect of another nAChR partial agonist (1S,5S)-3-(3,6-diaza-bicyclo[3.2.0]hept-3-yl)-quinoline (Compound D; α4β2 [$^3$H] cytisine $K_i$=6 nM)). Compound D alone does not evoke a response, but when co-applied with the PAM, 3-(3-(pyridin-3-yl)-1,2,4-oxadiazol-5-yl)benzonitrile (Compound 1), evoked robust responses at α4β2 nAChRs (FIG. 4A), but not at α3β4 nAChRs (FIG. 4B). Compound D is a representative of other nicotinic partial agonists.
Figure 4B:
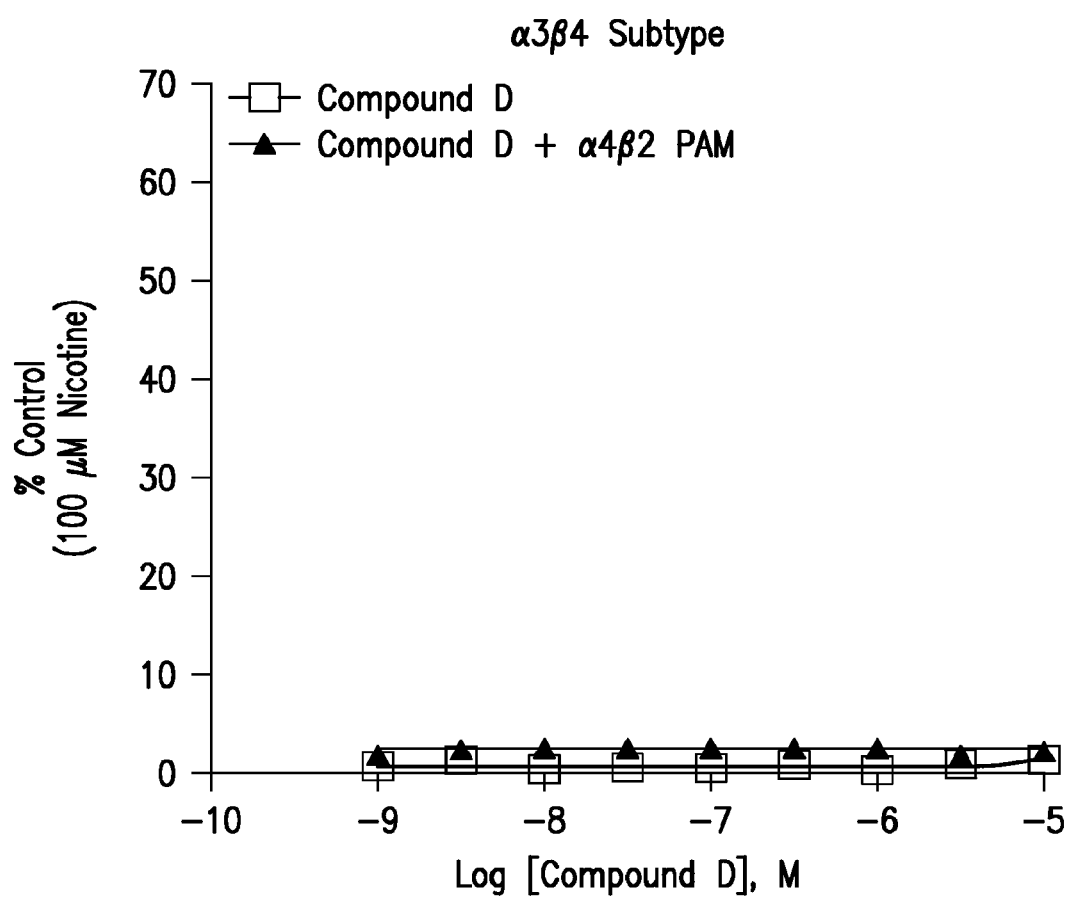

Example 2

α4β2 Positive Allosteric Modulator Enhances the Effects of Nicotinic Ligands with Very Low Intrinsic Agonist Efficacy Calcium Flux Assays: HEK-293 cells stably expressing human α4β2 or α3β4 are to confluency in 162 $cm^2$ tissue culture flasks in DMEM media supplemented with 10% FBS and 25 μg/ml zeocin and 200 μg/ml hygromycin B. IMR-32 neuroblastoma cells (ATCC) are grown to confluency in 162 $cm^2$ tissue culture flasks in minimum essential media supplemented with 10% FBS and 1 mM sodium pyruvate, 1% non-essential amino acids and 1% antibiotic-antimycotic. The cells are then dissociated using cell dissociation buffer and 100-150 µl per well of 3.5×10⁵ cells/ml cell suspension (~50,000-100,000 cells/well) was plated into 96-well black plates (poly-D-lysine precoated) with clear bottom and maintained for 24-48 hrs in a tissue culture incubator at 37° C. under an atmosphere of 5% $CO_2$: 95% air. Other clonal cell lines or dissociated primary cortical neurons that express endogenous α4* nicotinic receptors may also be used in this assay. Calcium flux was measured using calcium-3 assay kit (Molecular Devices, Sunnyvale, Calif.) or fluo-4 (Invitrogen). A stock solution of the dye was prepared by dissolving each vial supplied by the vendor in Hank's balanced salt solution buffer (HBSS) or 150 mM NMDG, 20 mM $CaCl_2$ containing 10 mM HEPES. The stock solution was diluted 1:20 using the same buffer before use. The growth media was removed from the cells. The cells were loaded with 100 µl of the dye per well and incubated at room temperature for up to one hour for HEK 293 clonal stable cell lines or 30 min-45 min at 37° C. for IMR-32 cells. Fluorescence measurements were read simultaneously from all the wells by a Fluorometic Imaging Plate Reader (FLIPR) at an excitation wavelength of 480 nm and an emission wavelength of 520 nm. Baseline fluorescence was measured for the first 6 seconds at which 3× concentrations of modulator/test compounds were added to the cell plate at 50 µl and incubated for five minutes. The fluorescence intensity was captured every second for the first 1 minute followed by every 5 seconds for an additional 4 minutes. This procedure was followed by 50 µl of 4× concentration of agonist and readings were taken for a period of 3-5 minutes as described above. Data was normalized to maximal responses and plotted as a function of concentration. The concentration dependence of changes fluorescence responses was fitted by nonlinear regression analysis (GraphPad Prism, San Diego, Calif.) to obtain $EC_{50}$ values.

α4β2 PAMs can also enhance the efficacy of partial agonists (compounds that bind, but activate α4β2 nAChRs with low intrinsic efficacy leading to otherwise barely detectable effects on calcium responses). For example, responses to 2-methyl-3-(2-(S)-pyrrolidinylmethoxy)pyridine (Compound C) in the presence and absence of PAM is shown in FIG. 3. The results show in the presence of an α4β2 PAM (for example, 3-(3-(pyridin-3-yl)-1,2,4-oxadiazol-5-yl)benzonitrile (Compound 1)), the maximum fluorescence calcium signal was substantially enhanced to application of 2-methyl-3-(2-(S)-pyrrolidinylmethoxy)pyridine at the α4β2 receptor (FIG. 3A), but again, not at the α3β4 receptor (FIG. 3B). Another example is provided by Compound D, (1S,5S)-3-(3,6-diaza-bicyclo[3.2.0]hept-3-yl)-quinoline; compound with toluene-4-sulfonic acid which also binds to α4β2 nAChR ([³H]cyt Ki=6 nM), but does not show substantial calcium responses alone; however, when co-incubated with α4β2 PAM, responses are substantially enhanced at α4β2 nAChR (FIG. 4A), but not at α3β4 nAChRs (FIG. 4B). These observations provides mechanistic support for compounds like 2-methyl-3-(2-(S)-pyrrolidinylmethoxy)pyridine and (1S,5S)-3-(3,6-Diaza-bicyclo[3.2.0]hept-3-yl)-quinoline being more effective when co-applied with the PAM. The potentiation of α4β2 effects by PAM may potential for optimizing and enhancing efficacy in indications such as ADHD, cognitive deficits, Alzhiemer's disease, and pain.

Figure 5:
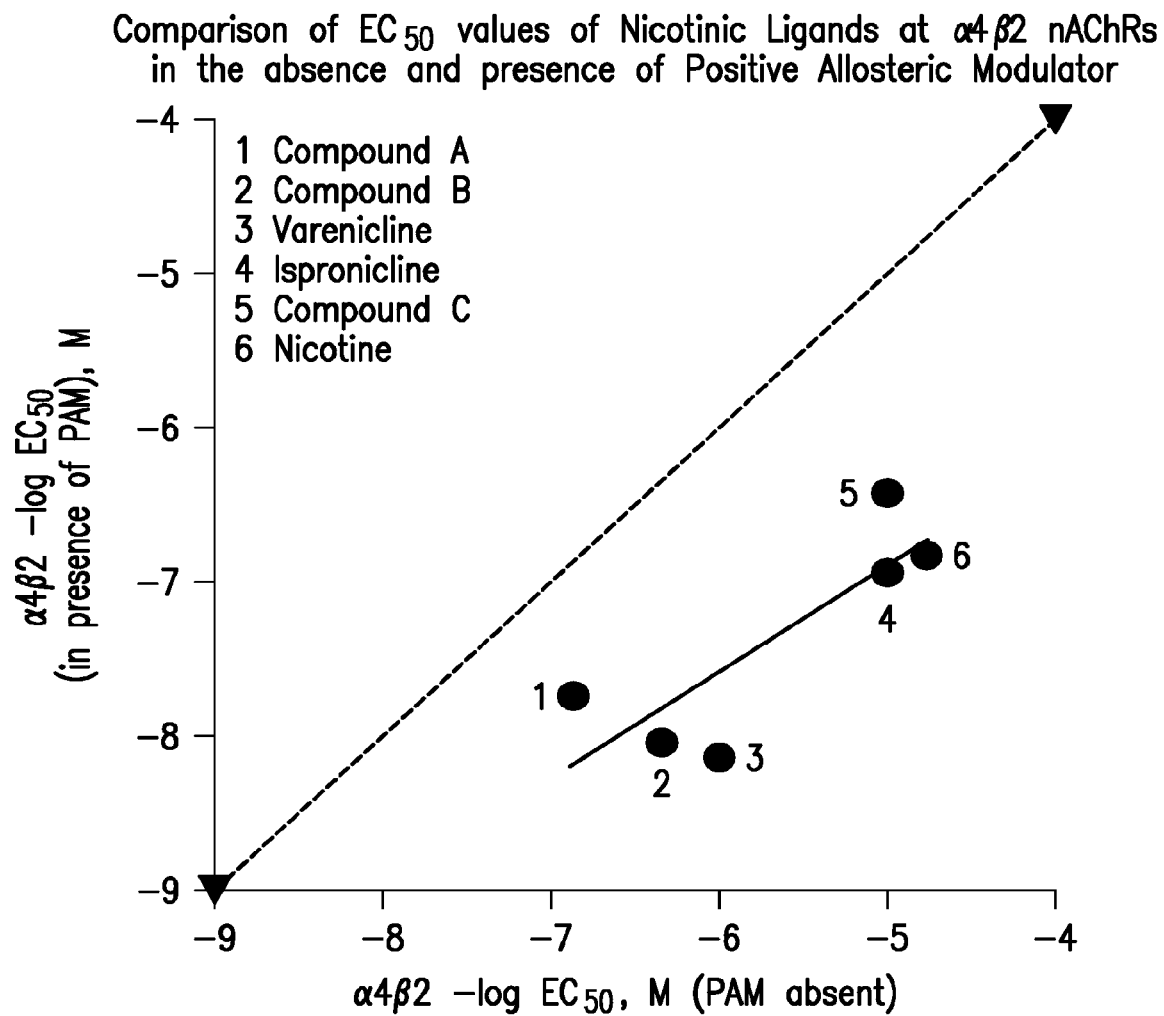
FIG. 5 shows correlation of potencies for activation of α4β2 nAChRs by various nicotinic acetycholine receptor ligands in the presence and absence of an α4β2 PAM, 3-(3-(pyridin-3-yl)-1,2,4-oxadiazol-5-yl)benzonitrile (Compound 1). In general, these nicotinic ligands are found to be more potent in activating α4β2 nAChRs in the presence of α4β2 PAM (Compound 1).

FIG. 5 shows a comparison of $EC_{50}$ values from calcium fluorescence (FLIPR) assays using α4β2 nAChRs of several nicotinic agonists including varenicline and ispronicline in the presence and absence of positive allosteric modulator. The potency ($EC_{50}$ values) of the nicotinic agonists increase in the presence of the positive allosteric modulator.

Example 3

α4β2 PAM Enhances the Efficacy of Compound A in an In Vivo Model of Neuropathic Pain To assess whether α4β2 PAM can increase antinociceptive responses of agonists in vivo, the following study was conducted. The materials and methods used to accomplish the study follow.

Animals: Male Sprague-Dawley rats (Charles River, Wilmington, Mass.) weighing 120-150 grams at time of surgery were utilized. These animals were group housed in AAALAC approved facilities at Abbott Laboratories in a temperature-regulated environment with lights on between 0700 and 2000 hours. Food and water was available ad libitum except during testing. All animal handling and experimental protocols were approved by an institutional animal care and use committee (IACUC). All experiments were performed during the light cycle.

Chemicals: 5-[(2R)-Azetidin-2-ylmethoxy]-2-chloropyridine (Compound A, 1-100 nmol/kg) and 3-(3-pyridin-3-yl)-1,2,4-oxadiazol-5-yl)benzonitrile (α4β2 PAM Compound 1, 1-35 µmol/kg, i.p.) was used. Compound A and D was prepared in saline and injected in solution in a volume of 2 ml/kg body weight 30 minutes before behavioral evaluation. Compound 1,3-(3-(pyridin-3-yl)-1,2,4-oxadiazol-5-yl)benzonitrile, was prepared in 30% hydroxybetacyclodextrin and injected in solution in a volume of 4 ml/kg body weight immediately before Compound A. For studies with Compound D, the doses tested ranged from 0.3-30 µmol/kg i.p.

Experimental Procedure: To produce neuropathic pain, tight ligation of the L5-L6 spinal nerves was performed. As previously described in detail by Kim and Chung (Kim S H and Chung J M (1992), Pain 50: 355), following sterilization procedures, a 1.5 cm incision was made dorsal to the lumbosacral plexus. The paraspinal muscles (left side) were separated from the spinous processes, the L5 and L6 spinal nerves isolated, and tightly ligated with 3-0 silk thread. Following hemostasis, the wound was sutured and coated with antibiotic ointment. The rats were allowed to recover and then placed in a cage with soft bedding for 7-14 days before behavioral testing for mechanical allodynia.

Tactile allodynia was measured using calibrated (force; g) von Frey filaments (Stoelting, Wood Dale, Ill.). Briefly, rats were placed into individual plexiglass containers and allowed to acclimate for 15-20 minutes before testing. Withdrawal threshold was determined by increasing and decreasing stimulus intensity and estimated using a Dixon non-parametric test (Chaplan et al., 1994; Chaplan S R, Bach F W, Pogrel J W, Chung J M and Yaksh T L (1994) J Neurosci Methods 53:55-63). Only rats with threshold scores ≤4.5 g were considered allodynic and utilized in further testing. A percent of maximal possible effect (% M.P.E.) of the tested compounds was calculated according to the formula: ([post-drug threshold]−[baseline threshold])/([maximum threshold]−[baseline threshold])×100%, where maximum threshold was equal to 15 g.

Statistical analysis: Analysis of the in vivo data was carried out using analysis of variance. Where appropriate, Bonferroni's Multiple Comparison Test was used for post-hoc analysis. The level of significance was set at p<0.05. Data are presented as mean±S.E.M.

Figure 6A:
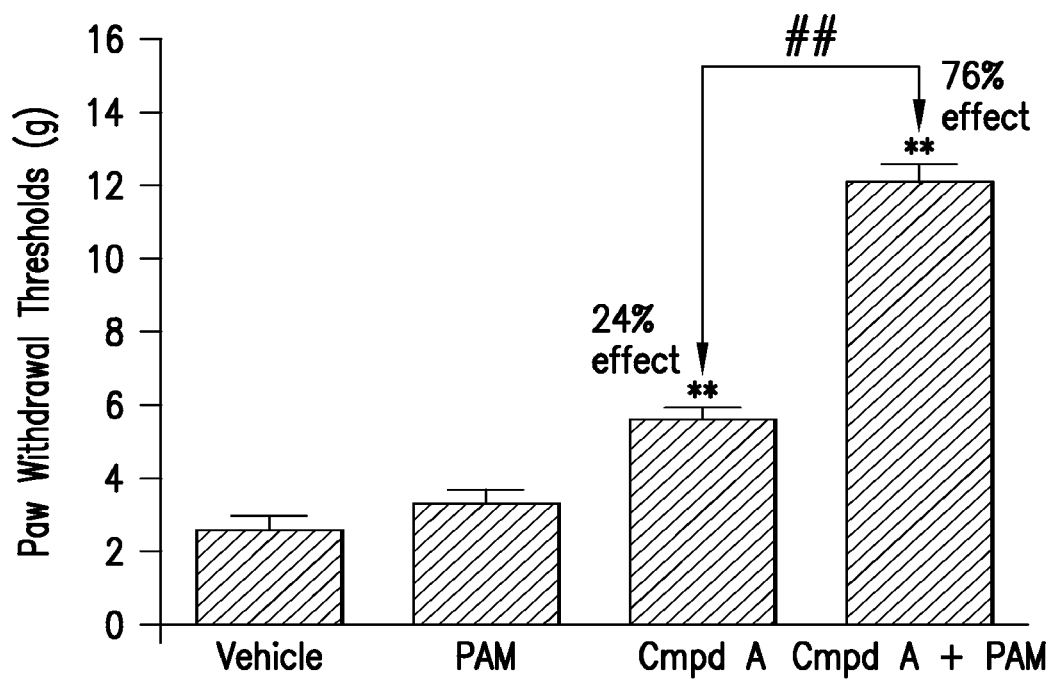
FIG. 6A graphically represents the effect of an α4β2 PAM, 3-(3-(pyridin-3-yl)-1,2,4-oxadiazol-5-yl)benzonitrile (Compound 1), on enhancing the efficacy by 5-[(2R)-azetidin-2-ylmethoxy]-2-chloropyridine (Compound A) in reversing neuropathic pain.

Results: As shown in FIG. 6A, tight ligation of L5-L6 spinal nerves induced pronounced mechanical allodynia with a decrease in mechanical paw withdrawal threshold (PWT) in the vehicle group to 2.6±0.4 g. Compound 1,3-(3-(pyridin-3-yl)-1,2,4-oxadiazol-5-yl)benzonitrile (PAM, 10 mg/kg, i.p.)

did not produce significant reversal of nerve injury induced mechanical allodynia (PWT: 3.3±0.4 g, P>0.05 vs. vehicle group). Compound A (0.03 μmol/kg, i.p.) produced weak but significant reversal of mechanical allodynia (PWT: 5.6±0.3 g, P<0.001 vs. vehicle group). When co-administered, Compound A+3-(3-(pyridin-3-yl)-1,2,4-oxadiazol-5-yl)benzonitrile (Compound 1, PAM) produced a pronounced reversal of nerve injury-induced mechanical allodynia (PWT: 12.1±0.5 g) that was significantly different from vehicle (P<0.001), but also from Compound A alone (P<0.001) and 3-(3-(pyridin-3-yl)-1,2,4-oxadiazol-5-yl)benzonitrile, Compound 1, alone (P<0.001). This study demonstrates that the co-administration of a α4β2 positive allosteric modulator to a α4β2 agonist potentiate the antiallodynic effects of the agonist. Since the efficacy of the α4β2 ligand in neuropathic pain is robustly improved in presence of a PAM, an overall improvement in therapeutic window for the treatment of pain may be envisaged utilizing a combination approach (agonist in combination with the α4β2 PAM).

Figure 6B:
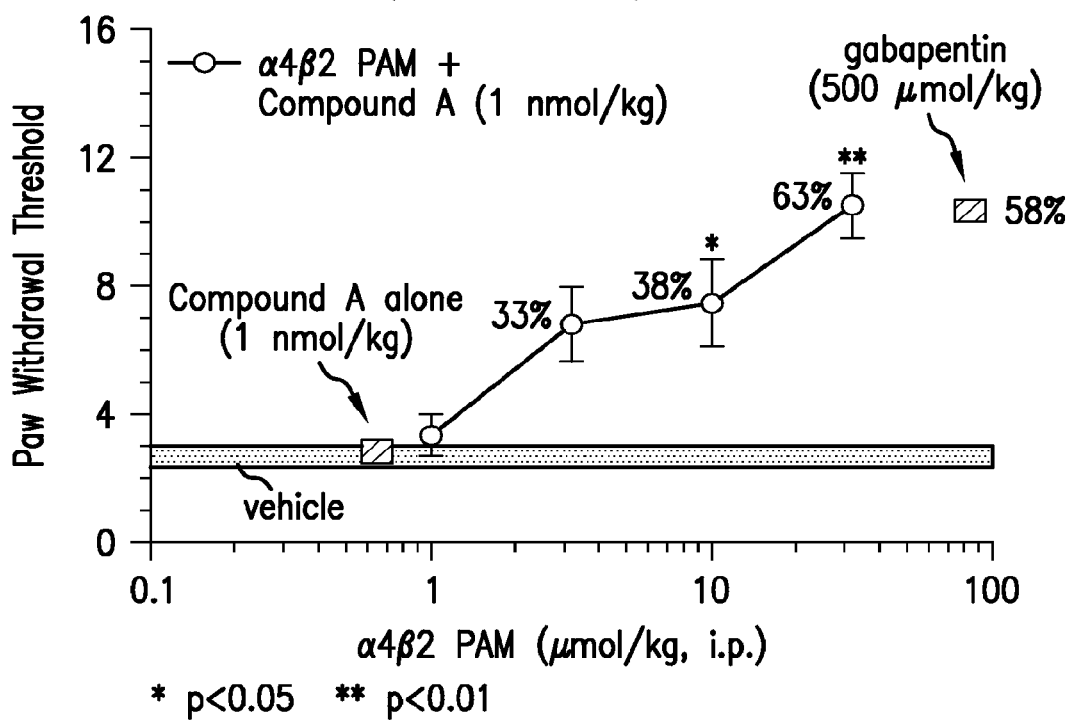
FIG. 6B graphically represents the dose dependent effect of an α4β2 PAM, 3-(3-(pyridin-3-yl)-1,2,4-oxadiazol-5-yl)benzonitrile (Compound 1), on enhancing the neuropathic pain efficacy of 5-[(2R)-azetidin-2-ylmethoxy]-2-chloropyridine (Compound A). An ineffective dose of Compound A (1 nmol/kg) demonstrates effect when combined with various doses of α4β2 PAM (Compound 1).

FIG. 6B shows that the effects of PAM (3-(3-(pyridin-3-yl)-1,2,4-oxadiazol-5-yl)benzonitrile, Compound 1) are dose-dependent. An ineffective dose of Compound A (1 nmol/kg), when combined with varying doses of PAM (3-(3-(pyridin-3-yl)-1,2,4-oxadiazol-5-yl)benzonitrile, Compound 1) results in dose-dependent increase in efficacy, approaching at least that of gabapentin, a drug clinically used for the treatment of neuropathic pain.

Figure 7A:
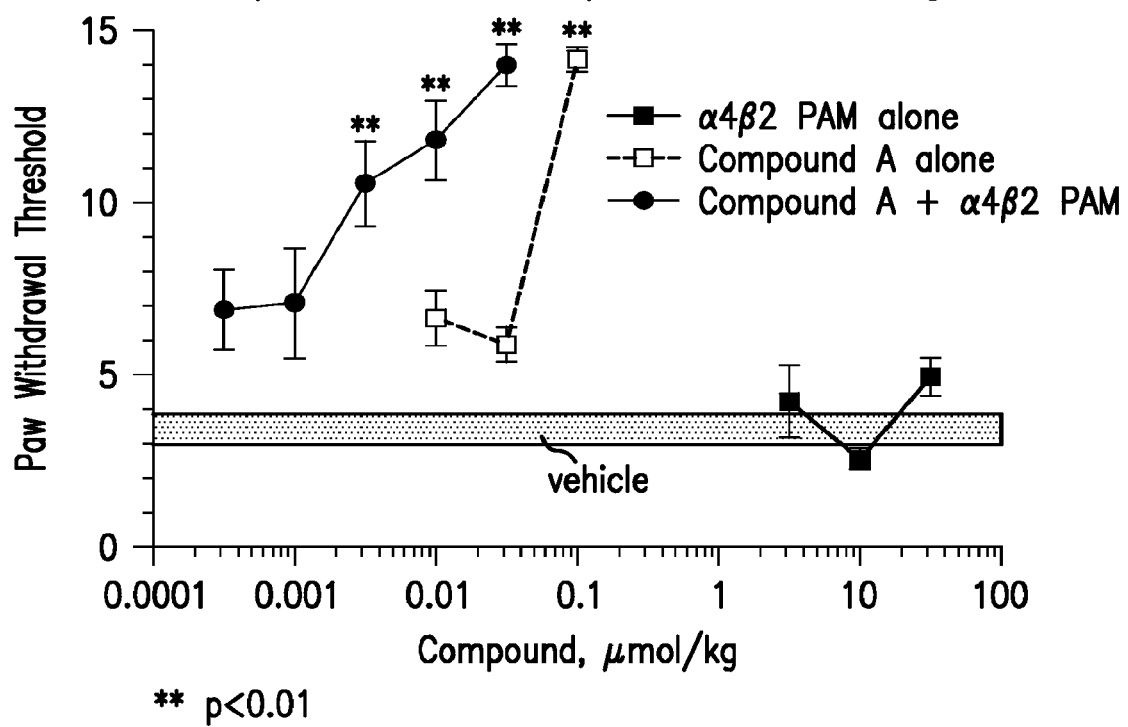
FIG. 7A shows dose-dependent effects in neuropathic pain of 5-[(2R)-azetidin-2-ylmethoxy]-2-chloropyridine (Compound A) alone, α4β2 PAM, 3-(3-(pyridin-3-yl)-1,2,4-oxadiazol-5-yl)benzonitrile (Compound 1), alone and a combination of Compound 1 (3.5 μmol/kg) with various doses of Compound A. An α4β2 PAM (Compound 1) alone is ineffective. However, in the presence of Compound 1 the dose response curve of Compound A in the Chung model of neuropathic pain shifts to the left.

FIG. 7A shows dose dependent effects in neuropathic pain of 5-[(2R)-azetidin-2-ylmethoxy]-2-chloropyridine (Compound A) alone, α4β2 PAM (3-(3-(pyridin-3-yl)-1,2,4-oxadiazol-5-yl)benzonitrile, Compound 1) alone and a combination of Compound 1 (3.5 μmol/kg) with various doses of Compound A. α4β2 PAM (Compound 1) alone is ineffective, but is capable of left-shifting the dose response curve of Compound A in the Chung model of neuropathic pain.

Example 4

Analysis of Compound Effects on Emesis in Ferrets

Fasted male ferrets (Marshall BioResources, North Rose, N.Y.) weighing between 1.0 and 1.7 kg are used to determine the emetic effects. α4β2 PAM (Compound 1) was administered first and thirty minutes later, Compound A was administered at various doses. After dosing, the animals were observed for emesis and behaviors characteristic of nausea for a period of 90 minutes. The percentage of animals that experienced emesis at a given dose was recorded.

Figure 7B:
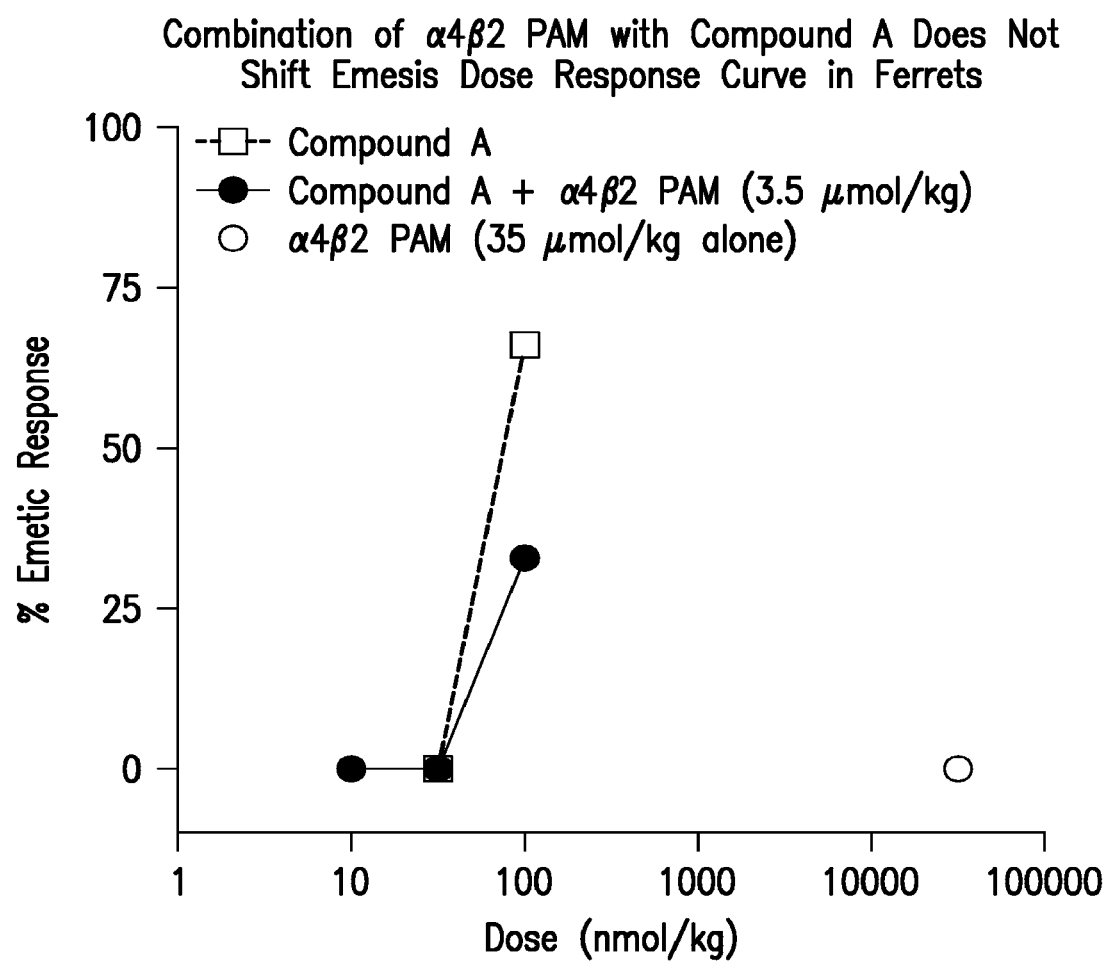
FIG. 7B shows the effects on emesis in ferrets. The effects of 5-[(2R)-azetidin-2-ylmethoxy]-2-chloropyridine (Compound A) alone, α4β2 PAM, 3-(3-(pyridin-3-yl)-1,2,4-oxadiazol-5-yl)benzonitrile (Compound 1), alone and a combination of Compound 1 (3.5 μmol/kg) with various doses of Compound A are shown. An α4β2 PAM (Compound 1) alone does not cause emesis, and does not shift the dose response curve of Compound A in the ferret model of emesis.

FIG. 7B shows effects on emesis. Shown are effects of 5-[(2R)-azetidin-2-ylmethoxy]-2-chloropyridine (Compound A) alone, α4β2 PAM (Compound 1) alone and a combination of Compound 1 (3.5 μmol/kg) with various doses of compound A. α4β2 PAM (Compound 1) alone does not cause emesis, and does not shift the dose response curve of Compound A in the ferret model of emesis.

Figure 8A:
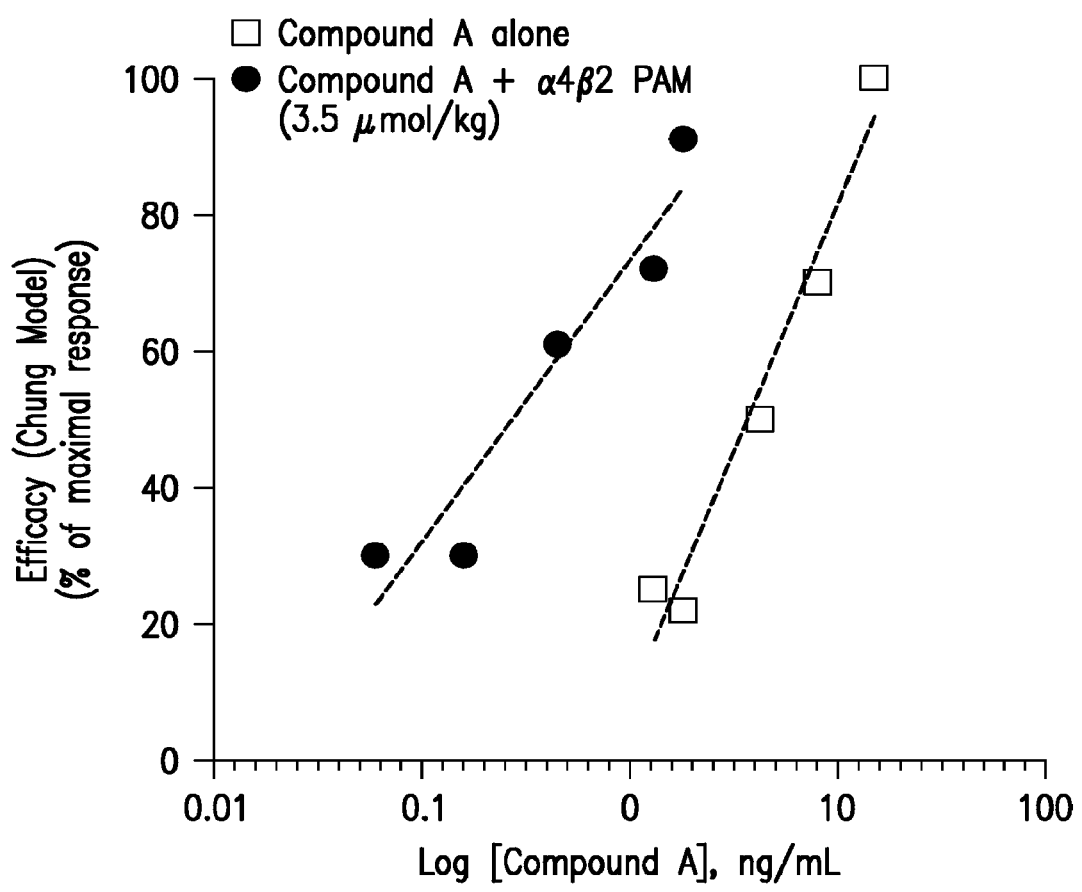
FIGS. 8A and 8B show plasma level analysis in models of neuropathic pain and emesis. The efficacy of Compound A is shifted left-ward as shown in FIG. 8A, but no shift in effects on emesis are shown in FIG. 8B. The maximal efficacy of Compound A can be realized in neuropathic pain without incidence of emesis, in presence of α4β2 PAM, 3-(3-(pyridin-3-yl)-1,2,4-oxadiazol-5-yl)benzonitrile (Compound 1). The data demonstrates that the therapeutic window of α4β2 nAChR agonists is wider in the presence of α4β2 PAM.
Figure 8B:
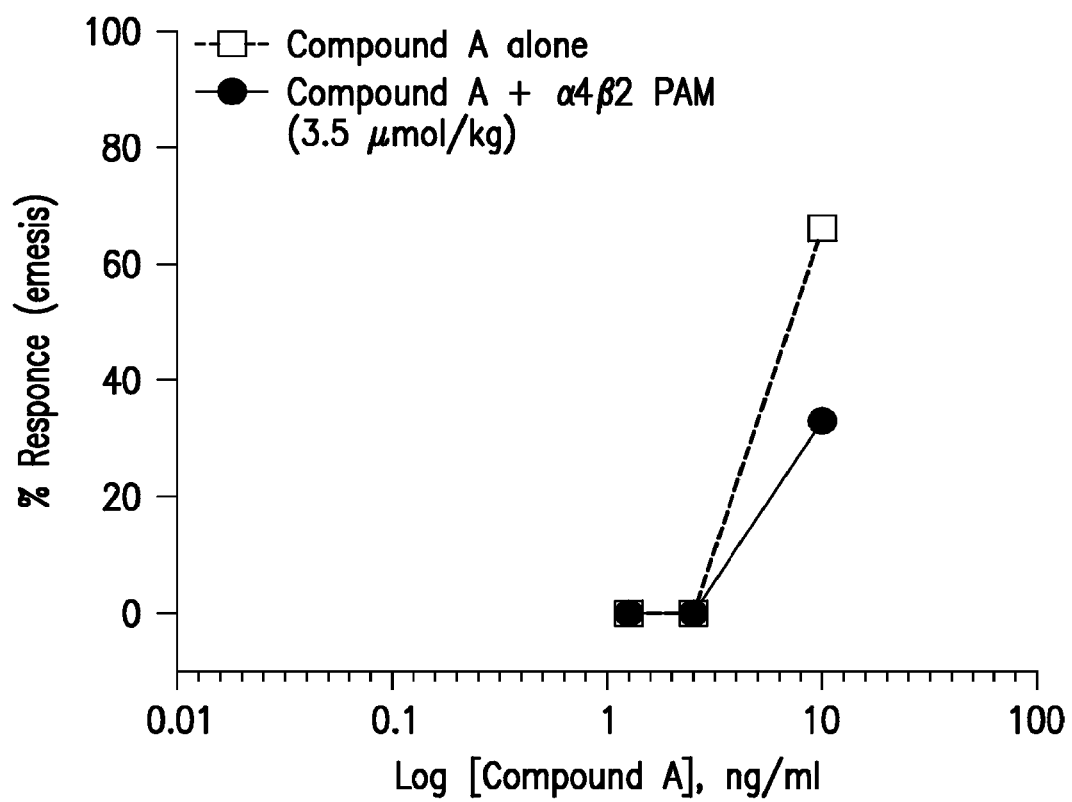
Figure 9:
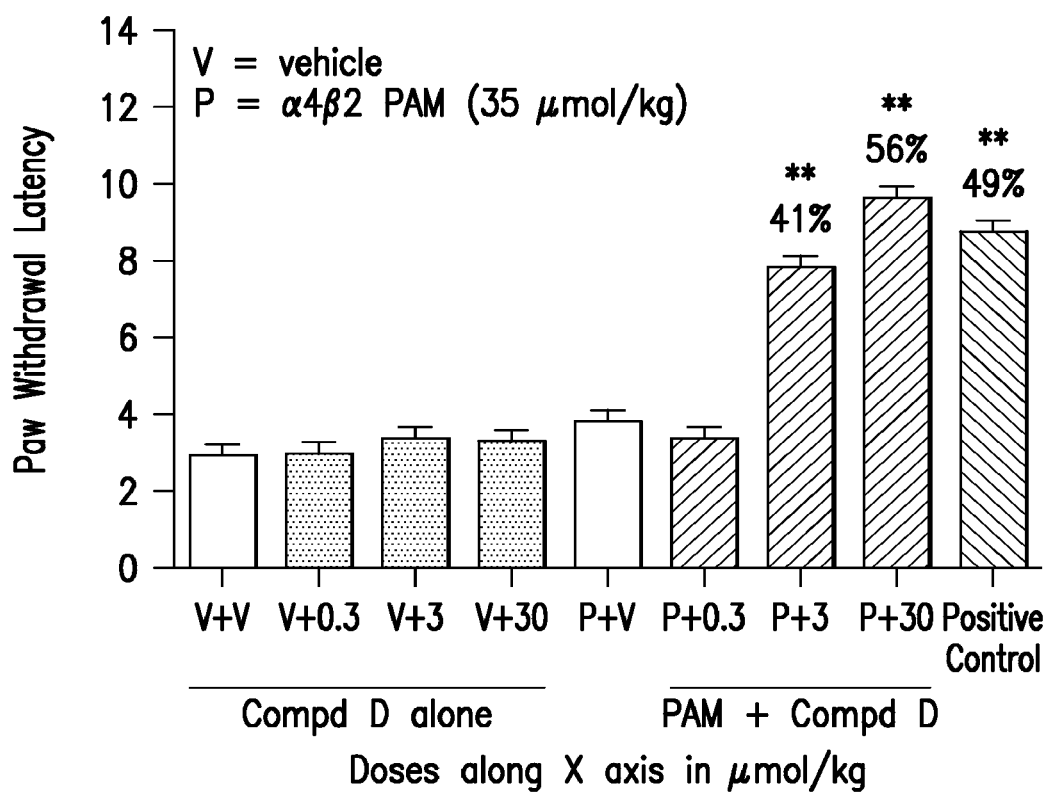
FIG. 9 shows the efficacy of a partial agonist, Compound D, in the presence and absence of α4β2 PAM, 3-(3-(pyridin-3-yl)-1,2,4-oxadiazol-5-yl)benzonitrile (Compound 1). In the example illustrated, Compound D when administered alone is ineffective in relieving pain. When co-dosed with α4β2 PAM (Compound 1), Compound D demonstrates effect, and the data demonstrate that Compound D provides significant relief of neuropathic pain in rats.

FIGS. 8A and 8B show plasma level analysis in models of neuropathic pain and emesis. Note the left ward shift in efficacy of Compound A in FIG. 8A, but no shift in effects on emesis in FIG. 8B. In other words, maximal efficacy of Compound A can be realized in neuropathic pain without incidence of emesis, in presence of α4β2 PAM (Compound 1), thus widening the therapeutic window of α4β2 nAChR agonists Example 5

α4β2 Partial Agonists Can Be Effective in Reversing Neuropathic Pain in the Presence of α4β2 Positive Allosteric Modulators To further examine effects in neuropathic pain, the effects of Compound D, another α4β2 ligand with low intrinsic efficacy (partial agonist) was examined in the Chung model. Alone, Compound D is ineffective in reversing neuropathic pain, but when combined with the PAM (Compound 1), significant efficacy can be realized. FIG. 9 shows the efficacy of partial agonist, Compound D in the presence and absence of α4β2 PAM (Compound 1). Compound D when administered alone is ineffective in relieving pain. When co-dosed with α4β2 PAM (Compound 1), Compound D is now effective, and shows significant relief of neuropathic pain in rats. As shown previously, PAM (Compound 1) alone is ineffective (P+V).

Characterization of Nicotinic Acetylcholine Receptor Ligands

In addition to the assays previously described for assessing nicotinic acetylcholine receptor positive allosteric modulators (fluorescence-based measurements, electrophysiology measurements using *Xenopus oocytes* or cell lines), the receptor interactions of positive allosteric modulators at α4β2 nAChRs also can be evaluated according to the [$^3$H]-POB binding assay, which was performed as described below.

[$^3$H]-3-(5-(Pyridin-3-yl)-1,2,4-oxadiazol-3-yl)benzonitrile ([$^3$H]-POB) Binding

Figure 10:
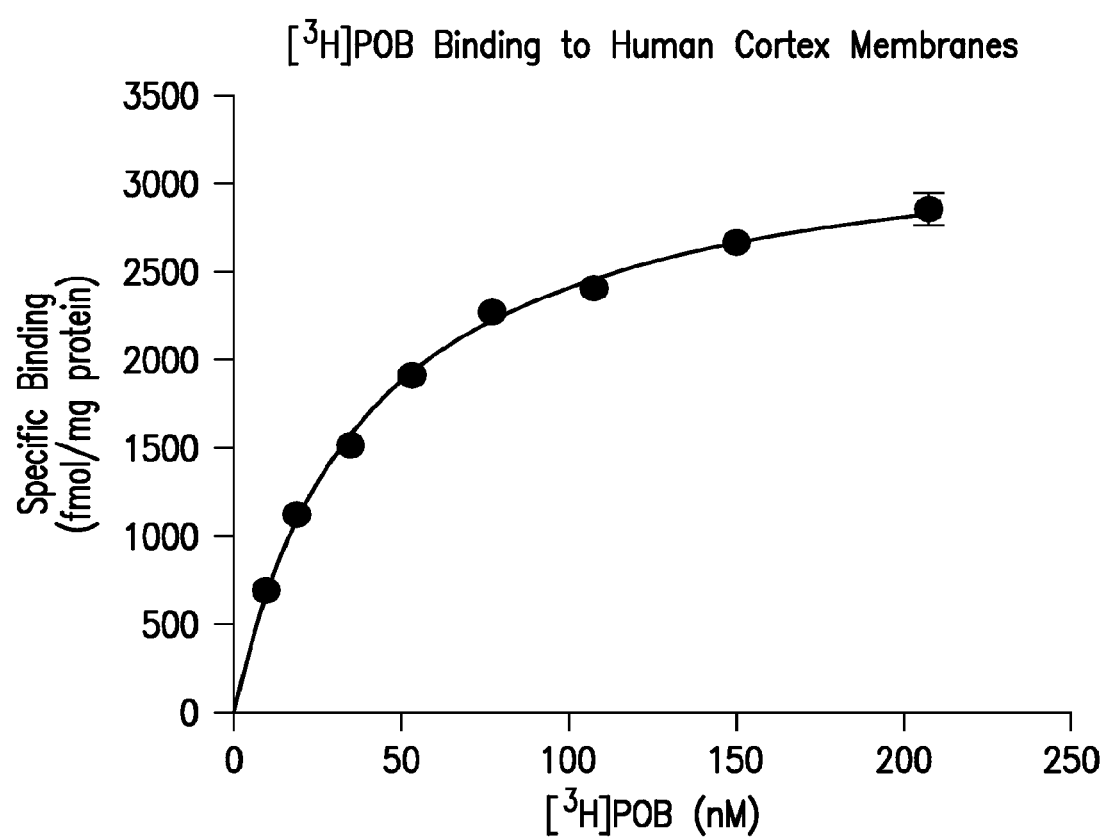
FIG. 10 is a graphical representation of specific binding to receptor sites in human brain membranes (fmoles per mg protein) as a function of the concentration of a radioligand [$^3$H]-3-(5-(pyridin-3-yl)-1,2,4-oxadiazol-3-yl)benzonitrile ([$^3$H]-POB, nM).

[$^3$H]-POB ([$^3$H]-3-(5-(pyridin-3-yl)-1,2,4-oxadiazol-3-yl)benzonitrile) binding to a α4β2 nAChR modulator site was determined using membrane enriched fractions from human cortex (ABS Inc., Wilmington, Del.). Pellets were thawed at 4° C., washed and resuspended with a Polytron at a setting of 7 in 30 volumes of BSS-Tris buffer (120 mM NaCl, 5 mM KCl, 2 mM CaCl$_2$, 2 mM MgCl$_2$, and 50 mM Tris-Cl, pH 7.4, 4° C.). For saturation binding isotherms, eight concentrations of [$^3$H]-POB (10-250 nM) in quadruplicate and homogenate containing 100-200 μg of protein were incubated in a final volume of 500 μL for 75 minutes at 4° C. Non-specific binding was determined in the presence of 30 μM unlabeled 3-(5-(pyridin-3-yl)-1,2,4-oxadiazol-3-yl)benzonitrile. Under these conditions, saturable binding of [$^3$H]-POB binding was measured in membrane enriched fractions from human frontal cortex (FIG. 10). The $K_d$ and $B_{max}$ values were 60±16 nM and 2900±500 fmol/mg protein, respectively. Membrane preparations from other species (rat, mouse, ferret) and from clonal or transfected cell lines that express α4β2 nAChRs cloned from various species may also be used in this binding assay.

For use in concentration-inhibition assays, seven log-dilution concentrations of test compounds containing 100-200 μg of protein, and 50 nM [$^3$H]-POB (16.4 Ci/mmol) were incubated in a final volume of 500 μL for 75 minutes at 4° C. in duplicate. Non-specific binding was determined in the presence of 30 μM 3-(5-(pyridin-3-yl)-1,2,4-oxadiazol-3-yl)benzonitrile. Bound radioactivity was collected on Millipore MultiScreen® harvest plates FB presoaked with 0.3% polyethyleneimine using a PerkinElmer cell harvester, washed with 2.5 mL of ice-cold buffer, and radioactivity was determined using a PerkinElmer TopCount Microplate beta counter. Dissociation constant ($K_d$) and maximum binding ($B_{max}$) values from saturation binding experiments were determined using GraphPad Prism (Graphpad Software, San Diego, Calif.). IC$_{50}$ values were determined by nonlinear regression in Microsoft® Excel or Assay Explorer. K$_i$ values were calculated from the IC$_{50}$s using the Cheng-Prusoff equation, where $K_i=IC_{50}/(1+[Ligand]/K_D])$.

[$^3$H]-POB was obtained according to the preparation procedures generally described in Example 79 shown below.

Example 79

[$^3$H]-3-(5-(pyridin-3-yl)-1,2,4-oxadiazol-3-yl)benzonitrile

Example 79A 3-(5-(5-bromopyridin-3-yl)-1,2,4-oxadiazol-3-yl)benzonitrile

The title compound was prepared according to the procedure of Example 4B using 3-cyano-N'-hydroxybenzimidamide and 5-bromonicotinoyl chloride (Alfa). $^1$H NMR (300 MHz, DMSO-d$_6$) δ 7.67 (m, 1H), 7.74 (m, 1H), 8.41 (m, 1H), 8.49 (m, 1H), 8.64 (s, 1H), 8.93 (s, 1H), 9.4 (s, 1H) ppm; MS (DCl/NH$_3$) m/z 327 (M+H)$^+$.

Example 79B

[$^3$H]-3-(5-(pyridin-3-yl)-1,2,4-oxadiazol-3-yl)benzonitrile ([$^3$H]-POB)

The compound of Example 79A was dissolved in a mixture of dichloromethane, triethylamine, and 5% palladium on carbon. The reaction solution was then saturated with tritium gas (1.2 Ci). The reaction mixture was stirred at room temperature for 3.5 hours, the catalyst was removed by filtration, ant the filtrate was concentrated to yield crude tritiated product. Further purification of the crude material by reverse-phase HPLC using a 30 minute 40% isocratic acetonitrile run (column LunaC18, 254 nm) to provide a total of 200 mCi (1 mL, MeOH).

The radiochemical purity of [$^3$H]-POB was found to be 99% and the specific activity was determined to be 16.4 Ci/mmol.

Nicotinic acetylcholine receptor ligands suitable for the invention exhibit K$_i$ values ranging about 1 nanomolar to about 10 micromolar when tested by the [$^3$H]-POB assay, many having a K$_i$ of less than 5 micromolar. Compounds that modulate the function of α4β2 nAChRs by altering the activity of the receptor or signaling are suitable for the composition. More specifically, the compounds that function as allosteric modulators enhancing the efficacy and/or potency of acetylcholine or a nicotinic agonist are desired. Multiple binding sites at α4β2 nAChRs may exist for such compounds, of which only one site may be defined by [$^3$H]POB binding.

Also contemplated is compound of formula:

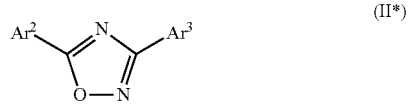

(II*)

or pharmaceutically acceptable salts thereof, wherein
Ar$^2$ is monocyclic aryl or monocyclic heteroaryl, wherein the aryl or heteroaryl is substituted or unsubstituted, and, when substituted, the aryl or heteroaryl is substituted with 1, 2, 3, or 4 substituents selected from halo, C$_1$-C$_6$ haloalkyl, C$_6$-C$_{10}$ aryl, C$_4$-C$_7$ cycloalkyl, C$_2$-C$_6$ alkenyl, C$_2$-C$_6$ alkynyl, C$_5$-C$_{10}$ heteroaryl, C$_4$-C$_{10}$ heterocycle, C$_1$-C$_6$ alkyl, —(C$_1$-C$_6$ alkyl)NHC(O)O—(C$_1$-C$_6$ alkyl), C$_1$-C$_6$ hydroxyalkyl, C$_1$-C$_6$ alkylcarbonyl, amino, hydroxyl, haloalkyl-C(O)—, haloalkyl-SO$_2$—, alkyl-SO$_2$—, —SO$_2$NH$_2$, —SO$_2$NH(C$_1$-C$_6$ alkyl), —SO$_2$N(C$_1$-C$_6$ alkyl)$_2$, cyano, nitro, C$_1$-C$_6$ acylamino, C$_1$-C$_6$ alkoxy, —C(O)NH$_2$, —C(O)O—(C$_1$-C$_6$ alkyl), and carboxy; and Ar$^3$ is monocyclic aryl or monocyclic heteroaryl, wherein the aryl or heteroaryl is substituted or unsubstituted, and, when substituted, the aryl or heteroaryl is substituted with a substituent selected from halo, C$_1$-C$_6$ haloalkyl, C$_6$-C$_{10}$ aryl, C$_4$-C$_7$ cycloalkyl, C$_2$-C$_6$ alkenyl, C$_2$-C$_6$ alkynyl, C$_5$-C$_{10}$ heteroaryl, C$_1$-C$_6$ alkyl, C$_1$-C$_6$ hydroxyalkyl, amino, hydroxyl, haloalkyl-SO$_2$—, cyano, nitro, C$_1$-C$_6$ acylamino, C$_1$-C$_6$ alkoxy, —N(C$_1$-C$_6$ alkyl)$_2$, and carboxy;

wherein at least one of the available atoms within a compound of formula (II*) is replaced with a radioisotope. A particular radiolabelled compound of formula (II*) is [$^3$H]-3-(5-(pyridin-3-yl)-1,2,4-oxadiazol-3-yl)benzonitrile. Such compounds are suitable for use in determining the binding affinity of nicotinic acetylcholine receptor subtype α4β2 positive allosteric modulators.

It is understood that the foregoing detailed description and accompanying examples are merely illustrative and are not to be taken as limitations upon the scope of the invention, which is defined solely by the appended claims and their equivalents. The compositions, methods, and articles of manufacture have been described with reference to various specific embodiments and techniques. However, various changes and modifications, including without limitation those relating to the compounds, substituents, syntheses, and/or methods of use of the invention, may be made without departing from the spirit and scope thereof. The examples described herein are intended only to illustrate and do not limit the scope of the invention as defined in the appended claims and equivalents thereof.

What is claimed is:

1. A method for treating pain in a patient, comprising:
   (i) administering an amount of nicotinic acetylcholine receptor ligand to the patient, wherein the nicotinic acetylcholine receptor ligand is 5[(2R)-azetidin-2-ylmethoxy]-2-chloropyridine; and
   (ii) administering an amount of nicotinic acetylcholine receptor subtype α4β2 positive allosteric modulator to the patient, wherein the nicotinic acetylcholine receptor subtype α4β2 positive allosteric modulator has the formula:

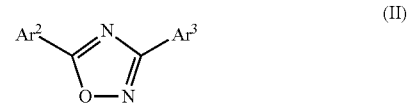

(II)

or is a pharmaceutically acceptable salt thereof, wherein
Ar$^2$ is phenyl or pyridinyl, wherein the phenyl or pyridinyl is substituted or unsubstituted, and, when substituted, the phenyl or pyridinyl is substituted with 1, 2, 3, or 4 substituents selected from halo, C$_1$-C$_6$ haloalkyl, C$_6$-C$_{10}$ aryl, C$_4$-C$_7$ cycloalkyl, C$_2$-C$_6$ alkenyl, C$_2$-C$_6$ alkynyl, C$_5$-C$_{10}$ heteroaryl, C$_4$-C$_{10}$ heterocycle, C$_1$-C$_6$ alkyl, —(C$_1$-C$_6$ alkyl)NHC(O)O—(C$_1$-C$_6$ alkyl), C$_1$-C$_6$ hydroxyalkyl, C$_1$-C$_6$ alkylcarbonyl, amino, hydroxyl, haloalkyl-C(O)—, haloalkyl-SO$_2$—, alkyl-SO$_2$—, —SO$_2$NH$_2$, —SO$_2$NH(C$_1$-C$_6$ alkyl), —SO$_2$N(C$_1$-C$_6$ alkyl)$_2$, cyano, nitro, C$_1$-C$_6$ acylamino, C$_1$-C$_6$ alkoxy, —C(O)NH$_2$, —C(O)O—(C$_1$-C$_6$ alkyl), and carboxy; and Ar$^3$ is phenyl or pyridinyl, wherein the phenyl or pyridinyl is substituted or unsubstituted, and, when substituted, the phenyl or pyridinyl is substituted with a substituent selected from halo, C$_1$-C$_6$ haloalkyl, C$_6$-C$_{10}$ aryl, C$_4$-C$_7$, cycloalkyl, C$_2$-C$_6$ alkenyl, C$_2$-C$_6$ alkynyl, C$_5$-C$_{10}$ heteroaryl, C$_1$-C$_6$ alkyl, C$_1$-C$_6$ hydroxyalkyl, amino, hydroxyl, haloalkyl-SO$_2$—, cyano, nitro, C$_1$-C$_6$ acylamino, C$_1$-C$_6$ alkoxy, —N(C$_1$-C$_6$ alkyl)$_2$, and carboxy; and wherein the amounts of (i) and (ii) together are more effective in treating pain.

2. The method of claim 1, further comprising administering a pain medication comprising a compound selected from an opioid, gabapentin, pregabalin, duloxetine, a cannabinoid ligand, a vaniolloid receptor antagonist, calcium channel blocker and a sodium channel blocker.

3. The method of claim 1, wherein Ar$^2$ is substituted pyridinyl, unsubstituted pyridinyl, or substituted phenyl; and Ar$^3$ is substituted pyridinyl, unsubstituted pyridinyl, or substituted phenyl; wherein the pyridinyl group, when substituted, is substituted with fluoro and the phenyl group is substituted with cyano, sulfonamide, or fluoro.

4. The method of claim 3, wherein Ar$^3$ is cyanophenyl and Ar$^3$ is pyridin-3-yl.

5. The method of claim 1, wherein the nicotinic acetylcholine receptor subtype α4β2 positive allosteric modulator is 3-(3-(pyridin-3-yl)-1,2,4-oxadiazol-5-yl)benzonitrile.

* * * * *